US008502680B2

(12) United States Patent
Tokhtuev et al.

(10) Patent No.: US 8,502,680 B2
(45) Date of Patent: Aug. 6, 2013

(54) HAND HYGIENE COMPLIANCE MONITORING

(75) Inventors: Eugene Tokhtuev, Duluth, MN (US); Christopher J. Owen, Duluth, MN (US); Paul S. Schilling, Duluth, MN (US); Anatoly Skirda, Duluth, MN (US); Viktor Slobodyan, Duluth, MN (US); Joseph P. Erickson, Cloquet, MN (US); Cheryl A. Littau, Apple Valley, MN (US); Christopher A. Buck, St. Paul, MN (US)

(73) Assignee: Ecolab USA Inc., St. Paul, MN (US)

( * ) Notice: Subject to any disclaimer, the term of this patent is extended or adjusted under 35 U.S.C. 154(b) by 572 days.

(21) Appl. No.: 12/787,064

(22) Filed: May 25, 2010

(65) Prior Publication Data
US 2010/0315243 A1    Dec. 16, 2010

Related U.S. Application Data

(60) Provisional application No. 61/186,676, filed on Jun. 12, 2009, provisional application No. 61/243,720, filed on Sep. 18, 2009.

(51) Int. Cl.
*G08B 23/00* (2006.01)

(52) U.S. Cl.
USPC .................................. 340/573.1; 340/539.12

(58) Field of Classification Search
None
See application file for complete search history.

(56) References Cited

U.S. PATENT DOCUMENTS
3,736,584 A    5/1973   Hackett et al.
3,761,909 A    9/1973   Schweitzer et al.
(Continued)

FOREIGN PATENT DOCUMENTS
DE    69708806 T2    8/2002
DE    69917795 T2    7/2005
(Continued)

OTHER PUBLICATIONS

SaferCorp, LLC, SaferCorp Life Advantage Solutions presents SaferHands™ Hospital Automated Hand Hygiene Monitoring System, retrieved electronically from http://www.guardianics.com/ on Dec. 15, 2010, 14 pp.

(Continued)

*Primary Examiner* — Travis Hunnings
(74) *Attorney, Agent, or Firm* — Shumaker & Sieffert, P.A.

(57) ABSTRACT

A system and associated processes monitor hand hygiene compliance. The system includes hand hygiene product dispensers positioned within areas of concern (AOC) in a facility in which hand hygiene events are to be monitored. The dispensers detect dispense events initiated at the dispenser and transmit a dispense event signal indicative that a dispense event occurred along with dispenser identification information. The system also includes a plurality of compliance badges, each worn by a different person in the facility. Each compliance badge receives dispense event signals corresponding dispenser identification information associated with dispense events initiated by the wearer of the compliance badge. The badges store dispense event records associated with each dispense event initiated by the wearer and thus keep track of all dispense events initiated by the wearer of the compliance badge. One or more data gathering stations positioned at various locations through the facility receive the dispense event information from the individual badges when they come within range. The dispense event information may then be transferred to a local or remote computer for analysis and reporting on hand hygiene events taking place within the facility.

20 Claims, 56 Drawing Sheets

(56) References Cited

U.S. PATENT DOCUMENTS

| | | |
|---|---|---|
| 3,786,467 A | 1/1974 | Cotter |
| 3,801,977 A | 4/1974 | Cotter |
| 3,866,198 A | 2/1975 | Cohen |
| 3,961,321 A | 6/1976 | Moss |
| 3,986,182 A | 10/1976 | Hackett |
| 4,076,146 A | 2/1978 | Lausberg et al. |
| 4,117,462 A | 9/1978 | Miller |
| 4,198,618 A | 4/1980 | Kleinschmidt |
| 4,209,776 A | 6/1980 | Frederick |
| 4,275,390 A | 6/1981 | Heywang et al. |
| 4,319,349 A | 3/1982 | Hackett |
| 4,360,905 A | 11/1982 | Hackett |
| 4,486,910 A | 12/1984 | Saalmann et al. |
| 4,539,846 A | 9/1985 | Grossman |
| 4,590,460 A | 5/1986 | Abbott et al. |
| 4,644,509 A | 2/1987 | Kiewit et al. |
| 4,727,522 A | 2/1988 | Steiner et al. |
| 4,729,120 A | 3/1988 | Steiner et al. |
| 4,896,144 A | 1/1990 | Bogstad |
| 4,987,402 A | 1/1991 | Nykerk |
| 4,991,146 A | 2/1991 | Ransdell et al. |
| 5,083,298 A | 1/1992 | Citterio et al. |
| 5,110,364 A | 5/1992 | Mazur et al. |
| 5,150,099 A | 9/1992 | Lienau |
| 5,153,520 A | 10/1992 | Dumbeck |
| 5,202,666 A | 4/1993 | Knippscheer |
| 5,245,317 A | 9/1993 | Chidley et al. |
| 5,263,006 A | 11/1993 | Hermesmeyer |
| 5,309,409 A | 5/1994 | Jones et al. |
| 5,370,267 A | 12/1994 | Schroeder |
| 5,390,385 A | 2/1995 | Beldham |
| 5,430,293 A | 7/1995 | Sato et al. |
| 5,463,595 A | 10/1995 | Rodhall et al. |
| 5,570,079 A | 10/1996 | Dockery |
| 5,610,589 A | 3/1997 | Evans et al. |
| 5,625,659 A | 4/1997 | Sears |
| 5,661,471 A | 8/1997 | Kotlicki |
| 5,684,458 A | 11/1997 | Calvarese |
| 5,695,091 A | 12/1997 | Winings et al. |
| 5,731,526 A | 3/1998 | Kindrick |
| 5,764,136 A | 6/1998 | Harron |
| 5,765,605 A | 6/1998 | Waymire et al. |
| 5,771,925 A | 6/1998 | Lewandowski |
| H1743 H | 8/1998 | Graves et al. |
| 5,793,653 A | 8/1998 | Segal |
| 5,812,059 A | 9/1998 | Shaw et al. |
| 5,900,067 A | 5/1999 | Jones |
| 5,913,915 A | 6/1999 | McQuinn |
| 5,917,425 A | 6/1999 | Crimmins et al. |
| 5,939,974 A | 8/1999 | Heagle et al. |
| 5,945,910 A | 8/1999 | Gorra |
| 5,952,924 A | 9/1999 | Evans et al. |
| 5,954,069 A | 9/1999 | Foster |
| 5,966,753 A * | 10/1999 | Gauthier et al. .................. 4/623 |
| 5,977,913 A | 11/1999 | Christ |
| 5,979,703 A | 11/1999 | Nystrom |
| 5,987,105 A | 11/1999 | Jenkins et al. |
| 6,012,041 A | 1/2000 | Brewer et al. |
| 6,031,461 A | 2/2000 | Lynn |
| 6,038,331 A | 3/2000 | Johnson |
| 6,065,639 A | 5/2000 | Maddox et al. |
| 6,125,482 A | 10/2000 | Foster |
| 6,130,607 A | 10/2000 | McClanahan et al. |
| 6,147,607 A | 11/2000 | Lynn |
| 6,175,308 B1 | 1/2001 | Tallman et al. |
| 6,191,693 B1 | 2/2001 | Sangsingkeow |
| 6,211,788 B1 | 4/2001 | Lynn et al. |
| 6,213,424 B1 | 4/2001 | Helfer-Grand |
| 6,236,317 B1 * | 5/2001 | Cohen et al. ............... 340/573.1 |
| 6,236,953 B1 | 5/2001 | Segal |
| 6,259,956 B1 | 7/2001 | Myers et al. |
| 6,278,372 B1 | 8/2001 | Velasco, Jr. et al. |
| 6,279,777 B1 | 8/2001 | Goodin et al. |
| 6,288,641 B1 | 9/2001 | Casais |
| 6,314,282 B1 | 11/2001 | Weber et al. |
| 6,331,964 B1 | 12/2001 | Barone |
| 6,351,223 B1 | 2/2002 | DeWeerd et al. |
| 6,360,181 B1 | 3/2002 | Gemmell et al. |
| 6,368,420 B1 | 4/2002 | Angevaare et al. |
| 6,375,038 B1 | 4/2002 | Daansen et al. |
| 6,392,546 B1 | 5/2002 | Smith |
| 6,404,837 B1 | 6/2002 | Thompson et al. |
| 6,417,773 B1 | 7/2002 | Vlahos et al. |
| 6,426,701 B1 | 7/2002 | Levy et al. |
| 6,476,385 B1 | 11/2002 | Albert |
| 6,485,979 B1 | 11/2002 | Kippenhan et al. |
| 6,523,193 B2 | 2/2003 | Saraya |
| 6,524,390 B1 | 2/2003 | Jones |
| 6,577,240 B2 | 6/2003 | Armstrong |
| 6,611,207 B1 | 8/2003 | Yuan et al. |
| 6,681,003 B2 | 1/2004 | Linder et al. |
| 6,707,873 B2 | 3/2004 | Thompson et al. |
| 6,727,818 B1 | 4/2004 | Wildman et al. |
| 6,730,024 B2 | 5/2004 | Freyre et al. |
| 6,749,148 B2 | 6/2004 | Helfer-Grand |
| 6,759,959 B2 | 7/2004 | Wildman |
| 6,778,092 B2 | 8/2004 | Braune |
| 6,781,523 B2 | 8/2004 | Matsui et al. |
| 6,792,395 B2 | 9/2004 | Roberts |
| 6,799,085 B1 | 9/2004 | Crisp, III |
| 6,882,278 B2 | 4/2005 | Winings et al. |
| 6,882,315 B2 | 4/2005 | Richley et al. |
| 6,883,563 B2 | 4/2005 | Smith |
| 6,917,290 B2 | 7/2005 | Land |
| 6,919,567 B2 | 7/2005 | Iwasawa |
| 6,956,498 B1 | 10/2005 | Gauthier et al. |
| 6,975,231 B2 | 12/2005 | Lane et al. |
| 7,015,816 B2 | 3/2006 | Wildman et al. |
| 7,023,356 B2 | 4/2006 | Burkhardt et al. |
| 7,042,361 B2 | 5/2006 | Kazdin et al. |
| 7,056,050 B2 | 6/2006 | Sacks |
| 7,067,054 B2 | 6/2006 | Fritze |
| 7,069,188 B2 | 6/2006 | Roberts |
| 7,075,412 B1 | 7/2006 | Reynolds et al. |
| 7,099,781 B1 | 8/2006 | Heidl et al. |
| 7,099,856 B2 | 8/2006 | Barangan et al. |
| 7,117,374 B2 | 10/2006 | Hill et al. |
| 7,119,688 B2 | 10/2006 | Wildman |
| 7,119,692 B2 | 10/2006 | Lieffort et al. |
| 7,142,108 B2 | 11/2006 | Diener et al. |
| 7,157,045 B2 | 1/2007 | McVey |
| 7,187,287 B2 | 3/2007 | Ryal |
| 7,191,090 B1 | 3/2007 | Cunningham |
| 7,201,005 B2 | 4/2007 | Voglewede et al. |
| 7,202,780 B2 | 4/2007 | Teller |
| 7,236,097 B1 | 6/2007 | Cunningham |
| 7,242,307 B1 | 7/2007 | LeBlond et al. |
| 7,248,933 B2 | 7/2007 | Wildman |
| 7,265,673 B2 | 9/2007 | Teller |
| 7,266,347 B2 | 9/2007 | Gross |
| 7,267,531 B2 | 9/2007 | Anderson et al. |
| 7,271,728 B2 | 9/2007 | Taylor et al. |
| 7,272,537 B2 | 9/2007 | Mogadam |
| 7,286,057 B2 | 10/2007 | Bolling |
| 7,292,914 B2 | 11/2007 | Jungmann et al. |
| 7,293,645 B2 | 11/2007 | Harper et al. |
| 7,315,245 B2 | 1/2008 | Lynn et al. |
| 7,330,108 B2 | 2/2008 | Thomas |
| 7,372,367 B2 | 5/2008 | Lane et al. |
| 7,375,640 B1 | 5/2008 | Plost |
| 7,400,264 B2 | 7/2008 | Boaz |
| 7,408,470 B2 | 8/2008 | Wildman et al. |
| 7,411,511 B2 | 8/2008 | Kennish et al. |
| 7,423,533 B1 | 9/2008 | LeBlond et al. |
| 7,425,900 B2 | 9/2008 | Lynn et al. |
| 7,440,620 B1 | 10/2008 | Aartsen |
| 7,443,305 B2 | 10/2008 | Verdiramo |
| 7,450,472 B2 | 11/2008 | Guyvarch |
| 7,457,869 B2 | 11/2008 | Kernan |
| 7,474,215 B2 | 1/2009 | Scott et al. |
| 7,477,148 B2 | 1/2009 | Lynn et al. |
| 7,482,936 B2 | 1/2009 | Bolling |
| 7,486,193 B2 | 2/2009 | Elwell |
| 7,487,538 B2 | 2/2009 | Mok |

| | | |
|---|---|---|
| 7,490,045 B1 | 2/2009 | Flores et al. |
| 7,496,479 B2 | 2/2009 | Garcia et al. |
| 7,538,680 B2 | 5/2009 | Scott et al. |
| 7,551,092 B1 | 6/2009 | Henry |
| 7,597,122 B1 | 10/2009 | Smith |
| 7,600,137 B2 | 10/2009 | Trappeniers et al. |
| 7,605,704 B2 | 10/2009 | Munro et al. |
| 7,611,030 B2 | 11/2009 | Reynolds et al. |
| 7,616,122 B2 | 11/2009 | Bolling |
| 7,718,395 B2 | 5/2010 | Carling |
| 7,780,453 B2 | 8/2010 | Carling |
| 7,785,109 B2 | 8/2010 | Carling |
| 2001/0039501 A1 | 11/2001 | Crevel et al. |
| 2001/0047214 A1 | 11/2001 | Cocking et al. |
| 2001/0053939 A1 | 12/2001 | Crevel et al. |
| 2001/0054038 A1 | 12/2001 | Crevel et al. |
| 2002/0000449 A1 | 1/2002 | Armstrong |
| 2002/0019709 A1 | 2/2002 | Segal |
| 2002/0050006 A1 | 5/2002 | Saraya |
| 2002/0103671 A1 | 8/2002 | Pederson et al. |
| 2002/0132343 A1 | 9/2002 | Lum |
| 2002/0135486 A1 | 9/2002 | Brohagen et al. |
| 2002/0145523 A1 | 10/2002 | Robaey |
| 2002/0175182 A1 | 11/2002 | Matthews et al. |
| 2002/0183979 A1 | 12/2002 | Wildman |
| 2003/0030562 A1 | 2/2003 | Lane et al. |
| 2003/0065536 A1 | 4/2003 | Hansen et al. |
| 2003/0074222 A1 | 4/2003 | Rosow et al. |
| 2003/0182180 A1 | 9/2003 | Zarrow |
| 2004/0001009 A1 | 1/2004 | Winings et al. |
| 2004/0015269 A1 | 1/2004 | Jungmann et al. |
| 2004/0028608 A1 | 2/2004 | Saul et al. |
| 2004/0049369 A1 | 3/2004 | Konicek et al. |
| 2004/0075347 A1 | 4/2004 | Biskup, Sr. et al. |
| 2004/0088076 A1 | 5/2004 | Gardner, Jr. |
| 2004/0090333 A1 | 5/2004 | Wildman et al. |
| 2004/0148196 A1 | 7/2004 | Kalies |
| 2004/0162850 A1 | 8/2004 | Sanville et al. |
| 2005/0086341 A1 | 4/2005 | Enga et al. |
| 2005/0102167 A1 | 5/2005 | Kapoor |
| 2005/0149341 A1 | 7/2005 | Eguchi et al. |
| 2005/0222889 A1 | 10/2005 | Lai et al. |
| 2006/0067545 A1 | 3/2006 | Lewis et al. |
| 2006/0067546 A1 | 3/2006 | Lewis et al. |
| 2006/0071799 A1 | 4/2006 | Verdiramo |
| 2006/0104245 A1 | 5/2006 | Narayanaswami et al. |
| 2006/0132316 A1* | 6/2006 | Wildman et al. .......... 340/573.1 |
| 2006/0139449 A1 | 6/2006 | Cheng et al. |
| 2006/0140703 A1 | 6/2006 | Sacks |
| 2006/0154642 A1 | 7/2006 | Scannell, Jr. |
| 2006/0223731 A1 | 10/2006 | Carling |
| 2006/0229821 A1 | 10/2006 | Brossette et al. |
| 2006/0272361 A1 | 12/2006 | Snodgrass |
| 2006/0273915 A1 | 12/2006 | Snodgrass |
| 2007/0008146 A1 | 1/2007 | Taylor et al. |
| 2007/0008147 A1 | 1/2007 | Bolling |
| 2007/0008149 A1 | 1/2007 | Bolling |
| 2007/0016466 A1 | 1/2007 | Taylor |
| 2007/0020212 A1 | 1/2007 | Bernal et al. |
| 2007/0029962 A1 | 2/2007 | Saeki |
| 2007/0044819 A1 | 3/2007 | Chan et al. |
| 2007/0055483 A1 | 3/2007 | Lee et al. |
| 2007/0056091 A1 | 3/2007 | Bolton et al. |
| 2007/0069884 A1 | 3/2007 | Waxman |
| 2007/0096930 A1 | 5/2007 | Cardoso |
| 2007/0182581 A1 | 8/2007 | Elwell |
| 2007/0198067 A1 | 8/2007 | Van den Heuvel et al. |
| 2007/0205861 A1 | 9/2007 | Nair et al. |
| 2007/0213877 A1 | 9/2007 | Hart et al. |
| 2007/0222599 A1 | 9/2007 | Coveley et al. |
| 2007/0229288 A1 | 10/2007 | Ogrin et al. |
| 2007/0247316 A1 | 10/2007 | Wildman et al. |
| 2007/0257803 A1 | 11/2007 | Munro et al. |
| 2007/0285277 A1 | 12/2007 | Scott et al. |
| 2007/0290865 A1 | 12/2007 | Lynn et al. |
| 2008/0001763 A1 | 1/2008 | Raja et al. |
| 2008/0019489 A1 | 1/2008 | Lynn |
| 2008/0046278 A1 | 2/2008 | Sanville et al. |
| 2008/0084315 A1 | 4/2008 | Pittz |
| 2008/0087719 A1 | 4/2008 | Sahud |
| 2008/0100441 A1* | 5/2008 | Prodanovich et al. ..... 340/572.1 |
| 2008/0103636 A1 | 5/2008 | Glenn et al. |
| 2008/0131332 A1 | 6/2008 | Nguyen et al. |
| 2008/0185540 A1 | 8/2008 | Turner et al. |
| 2008/0189142 A1 | 8/2008 | Brown et al. |
| 2008/0193631 A1 | 8/2008 | Kanamori et al. |
| 2008/0246599 A1 | 10/2008 | Hufton et al. |
| 2008/0266113 A1 | 10/2008 | Kennish et al. |
| 2008/0280380 A1 | 11/2008 | Dietz et al. |
| 2008/0303658 A1 | 12/2008 | Melker et al. |
| 2009/0002644 A1 | 1/2009 | Christensen et al. |
| 2009/0019552 A1 | 1/2009 | McLaughlin et al. |
| 2009/0051545 A1 | 2/2009 | Koblasz |
| 2009/0091458 A1 | 4/2009 | Deutsch |
| 2009/0102681 A1 | 4/2009 | Brennan, Jr. et al. |
| 2009/0112630 A1 | 4/2009 | Collins, Jr. et al. |
| 2009/0119142 A1 | 5/2009 | Yenni et al. |
| 2009/0138303 A1 | 5/2009 | Seshadri |
| 2009/0195385 A1 | 8/2009 | Huang et al. |
| 2009/0204256 A1 | 8/2009 | Wegelin |
| 2009/0219131 A1 | 9/2009 | Barnett et al. |
| 2009/0219172 A1 | 9/2009 | Wilbrod |
| 2009/0224907 A1 | 9/2009 | Sinha et al. |
| 2009/0224924 A1* | 9/2009 | Thorp ........................ 340/573.1 |
| 2009/0267776 A1* | 10/2009 | Glenn et al. ................ 340/573.1 |
| 2009/0276239 A1 | 11/2009 | Swart et al. |
| 2010/0233020 A1 | 9/2010 | Klaassen et al. |
| 2010/0274640 A1 | 10/2010 | Morey et al. |
| 2010/0315244 A1 | 12/2010 | Tokhtuev et al. |

FOREIGN PATENT DOCUMENTS

| | | |
|---|---|---|
| DE | 19882120 B4 | 10/2010 |
| EP | 0921506 A1 | 6/1999 |
| EP | 1099400 A2 | 5/2001 |
| EP | 1201172 A2 | 5/2002 |
| EP | 1390204 B1 | 12/2004 |
| EP | 1034132 B1 | 8/2005 |
| EP | 1483728 B1 | 4/2006 |
| EP | 1791077 A2 | 5/2007 |
| EP | 1872802 A1 | 1/2008 |
| EP | 1872892 A1 | 2/2008 |
| EP | 1913892 A2 | 4/2008 |
| GB | 2137749 A | 10/1984 |
| GB | 2217013 A | 10/1989 |
| GB | 2299405 A | 2/1996 |
| GB | 2324397 A | 10/1998 |
| GB | 2337327 A | 11/1999 |
| GB | 2340647 A | 2/2000 |
| GB | 2394654 A | 5/2004 |
| GB | 2417810 A | 3/2006 |
| GB | 2417811 A | 3/2006 |
| GB | 2425388 A | 10/2006 |
| GB | 2446871 A | 8/2007 |
| GB | 2437555 A | 10/2007 |
| GB | 2439306 A | 12/2007 |
| GB | 2439457 A | 12/2007 |
| JP | 10309540 A | 11/1998 |
| JP | 2002197559 A | 7/2002 |
| JP | 2003105819 A | 4/2003 |
| JP | 2003122823 A | 4/2003 |
| JP | 2005218999 A | 8/2005 |
| JP | 2006198318 A | 8/2006 |
| WO | 92/13327 | 8/1992 |
| WO | 97/31350 | 8/1997 |
| WO | 98/09261 | 3/1998 |
| WO | 98/36258 | 8/1998 |
| WO | 00/22260 | 4/2000 |
| WO | 01/33529 A1 | 5/2001 |
| WO | 02/21475 A1 | 3/2002 |
| WO | 03/079278 A1 | 9/2003 |
| WO | 03/082351 A2 | 10/2003 |
| WO | 2005/055793 A2 | 6/2005 |
| WO | 2005/055793 A3 | 6/2005 |
| WO | 2005/094711 A2 | 10/2005 |
| WO | 2006/036687 A1 | 4/2006 |
| WO | WO 2006/135922 A3 | 12/2006 |
| WO | 2007/001866 A2 | 1/2007 |
| WO | 2007/090470 A1 | 8/2007 |

| | | | |
|---|---|---|---|
| WO | 2007/129289 A1 | 11/2007 | |
| WO | 2007/133960 A2 | 11/2007 | |
| WO | 2008/088424 A1 | 7/2008 | |
| WO | 2008/133495 A1 | 11/2008 | |
| WO | 2010/101929 A2 | 9/2010 | |

OTHER PUBLICATIONS

SaferCorp, LLC, Guardian™ Automated Infection Control Systems (GAICS), Feb. 6, 2010, 4 pp.
Office Action from U.S. Appl. No. 12/432,277, dated Sep. 16, 2011, 14 pp.
Response to Office Action dated Sep. 16, 2011, from U.S. Appl. No. 12/432,277, filed Dec. 16, 2011, 14 pp.
Malik et al., "Use of Audit Tools to Evaluate the Efficacy of Cleaning Systems in Hospitals," Am. J. Infect. Control, vol. 31, No. 3, p. 181-187, May 2003.
Griffith et al., "An Evaluation of Hospital Cleaning Regimes and Standards," J. Hosp. Infect., vol. 45, pp. 19-28, 2000.
Written Opinion of international application No. PCT/IB2010/052322, dated Feb. 1, 2010, 6 pp.
Ophardt Hygiene-Technik GmbH + Co. KG, "Making the World a More Hygienic Place", 2009, 1 page.
Elliot, "Determining Three Metrics for Cleaning Satisfaction," found at http://www.facilitiesnet.com/equipmentrentaltools/article/Determining-Three-Metrics-for-Cleaning-Satisfaction--7698#, Nov. 2007, 2 pp.
Van Ryzin et al., "Measuring Street Cleanliness: A Comparison of New York City's Scorecard and Results from a Citizen Survey," Public Administration Review 68(2):295-303, Mar./Apr. 2008.
Evaluating Municipal Services: Scorecard Cleanliness Program Prospectus, New York, found at http://www.worldsweeper.com/Street/Profiles/NYCScorecard.pdf, archived Jan. 5, 2009, 20 pp.
Office Action from U.S. Appl. No. 12/766,714, dated Mar. 29, 2012, 20 pp.
Response to Office Action dated Mar. 29, 2012, from U.S. Appl. No. 12/766,714, filed Jun. 28, 2012, 8 pp.
Yoshikura, "Workflow from Clean to Dirty, HACCP and Inclusiveness Principles in Effective Implementation of Hospital Infection Control," Jpn. J. Infect. Dis. 53:124-125, 2000.
Quattrin, MD. et al., "Application of Hazard Analysis Critical Control Points to Control Surgical Site Infections in Hip and Knee Arthroplasty," Orthopedics 31, 6 pp., Feb. 2008.
Griffith, "Nosocomial infection: Are there lessons from the food industry?" The Biomedical Scientist, pp. 697-699, Aug. 2006.
Bourn, Auditor General for Wales, "The Management and Delivery of Hospital Cleaning Services in Wales," National Audit Office Wales, 39 pp., May 23, 2003.
Mallow General Hospital, "Hygiene Services Assessment Scheme, Assessment Report," 38 pp., Oct. 2007.
Dix et al., "Environmental Surface Cleaning: First Defense Against Infectious Agents," Infection Control Today Magazine, 6 pp., Dec. 1, 2005.
Sturman et al., "Cornell Hospitality Report: A New Method for Measuring Housekeeping Performance Consistency," CHR Reports, vol. 6, No. 11, Sep. 2006, 15 pp.
Office Action from U.S. Appl. No. 12/432,277, dated Apr. 15, 2011, 16 pp.
Response to Office Action dated Apr. 15, 2011, U.S. Appl. No. 12/432,277, filed Jul. 14, 12 pp.
Office Action from U.S. Appl. No. 12/787,097, dated Jun. 4, 2012, 5 pp.
Response to Office Action dated Jun. 4, 2012, from U.S. Appl. No. 12/787,097, filed Sep. 4, 2012, 8 pp.
Al-Hamad et al., "How Clean is Clean? Proposed Methods for Hospital Cleaning Assessment," Journal of Hospital Infection, vol. 70, Oct. 9, 2008, pp. 328-334.
Lewis et al., "A Modified ATP Benchmark for Evaluating the Cleaning of Some Hospital Environmental Surfaces," Journal of Hospital Infection, vol. 69, May 12, 2008, pp. 156-163.
Exner et al., "Household Cleaning and Surface Disinfection: New Insights and Strategies," Journal of Hospital Infection, vol. 56, 2008, pp. s70-s75.
Griffith et al., "The Effectiveness of Existing and Modified Cleaning Regimens in a Welsh Hospital," Journal of Hospital Infection, vol. 66, Jul. 26, 2007, pp. 352-359.
Dancer, "How do we Assess Hospital Cleaning? A Proposal for Microbiological Standards for Surface Hygiene in Hospitals" Journal of Hospital Infection, vol. 56, 2004, pp. 10-15.
Zuhlsdorf et al., "Cleaning Efficacy of Nine Different Cleaners in a Washer-Disinfector Designed for Flexible Endoscopes," Journal of Hospital Infection, vol. 52, 2002, pp. 206-211.
Office Action from U.S. Appl. No. 12/766,714, dated Sep. 17, 2012, 28 pp.
Rifhat E. Malik et al., "Use of Audit Tools to Evaluate the Efficacy of Cleaning Systems in Hospitals," Am. J. Infect. Control, vol. 31, No. 3, p. 181-187 2003.
C. J. Griffith et al., "An Evaluation of Hospital Cleaning Regimes and Standards," J. Hosp. Infect., vol. 45, p. 19-28 2000.
U.S. Appl. No. 12/787,097, by Eugene Tokhtuev, filed May 25, 2010.
Office Action from U.S. Appl. No. 13/369,056, dated Feb. 5, 2013, 16 pp.
Response to Final Office Action dated Sep. 17, 2012, from U.S. Appl. No. 12/766,714, filed Dec. 17, 2012, 10 pp.
Notice of Allowance from U.S. Appl. No. 12/787,097, dated Nov. 7, 2012, 8 pp.

* cited by examiner

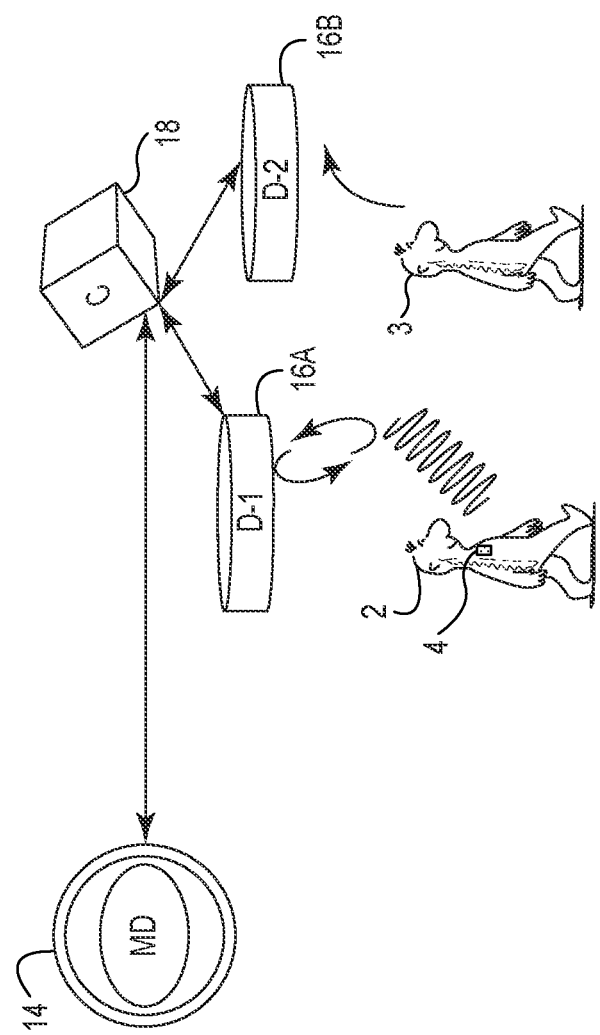

106 →

| Dispenser Location | Product Status | Product Type | Battery Status |
|---|---|---|---|
| W231 | OK | QuikCare | Low |
| W255 | Low | BactiStat | OK |
| W375 | Low | QuikCare | Low |
| E515 | Low | Endure 420 | OK |

Fig. 6C

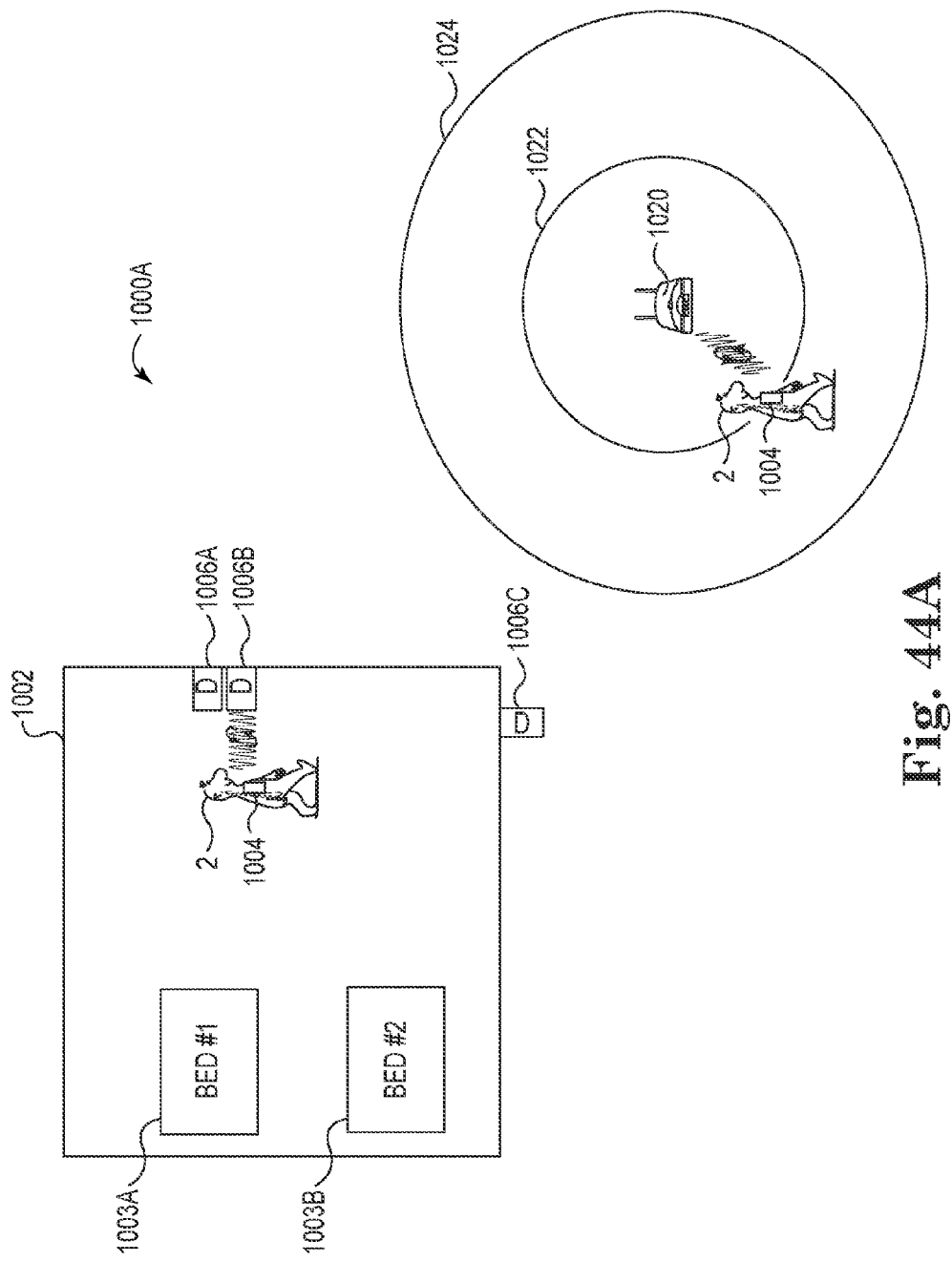

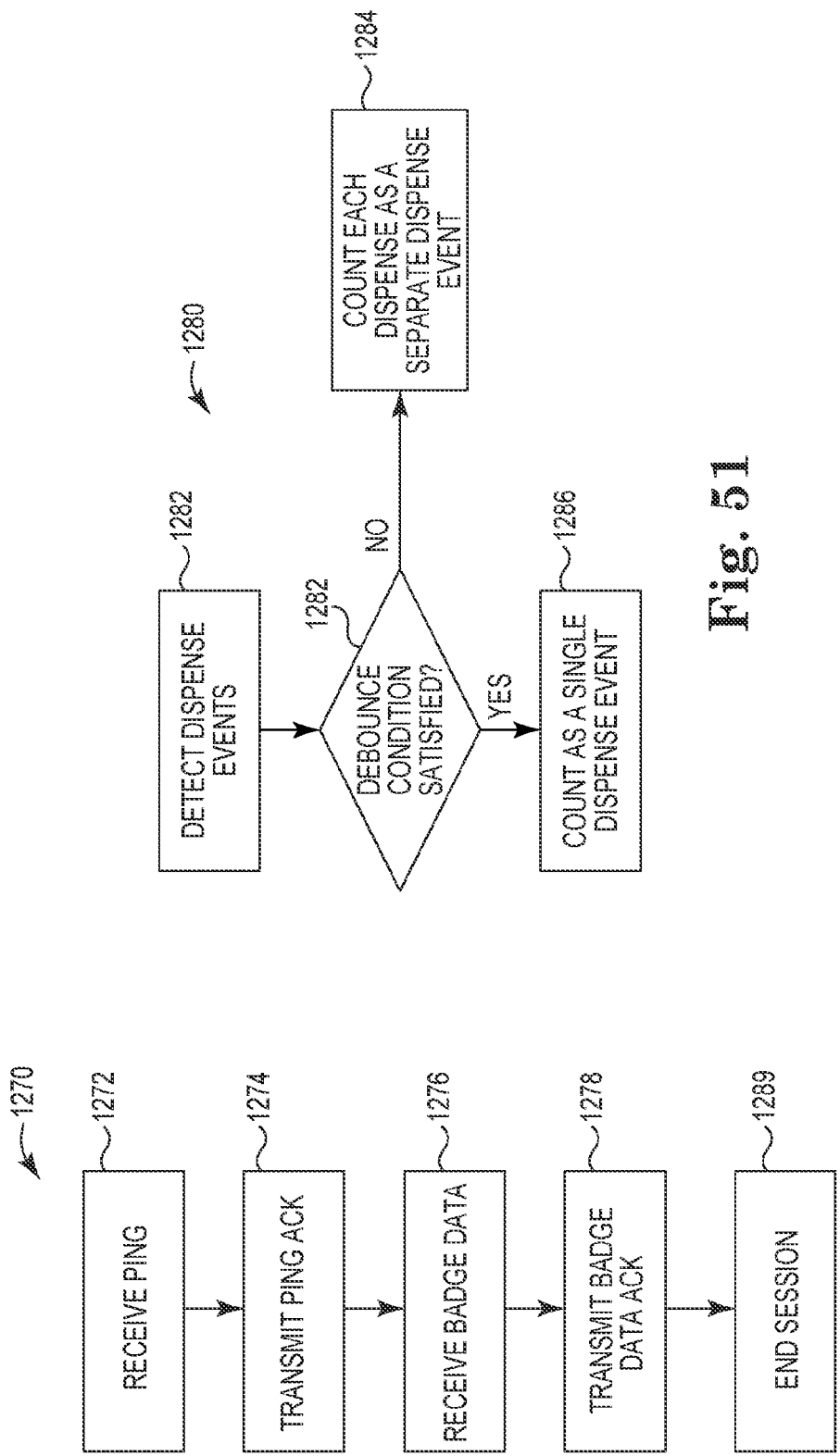

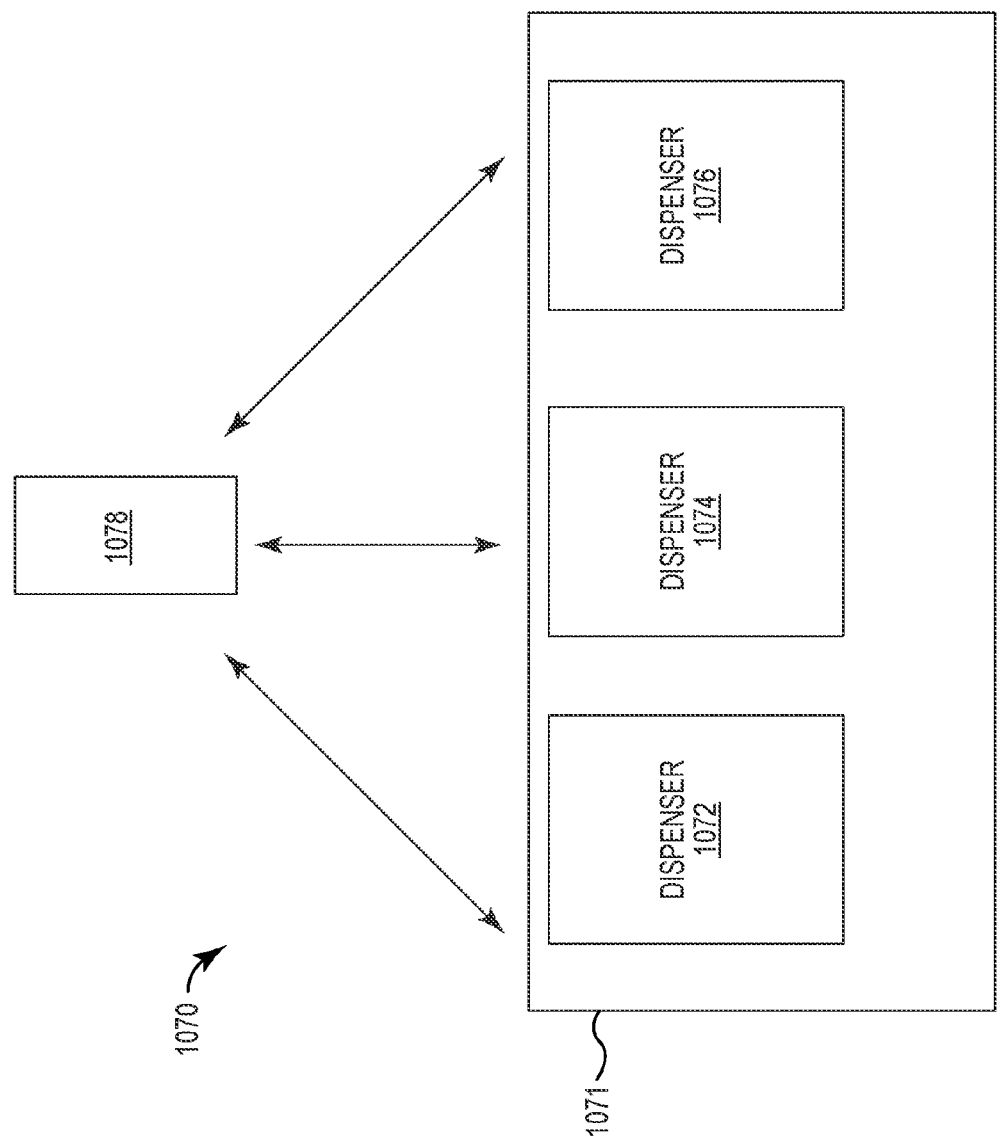

HAND HYGIENE COMPLIANCE MONITORING

CROSS REFERENCE TO RELATED APPLICATIONS

This application claims the benefit of U.S. Provisional Application No. 61/186,676, filed Jun. 12, 2009, and U.S. Provisional Application No. 61/243,720, filed Sep. 18, 2009, both of which are incorporated herein by reference in their entirety.

TECHNICAL FIELD

The disclosure relates to cleaning and sanitizing practices at a hospital or other healthcare facility.

BACKGROUND

Despite improvements in hand hygiene, stricter compliance requirements, and efforts to optimize isolation practices, hospitals and other healthcare facilities are losing the war on nosocomial or Hospital Acquired Infections (HAIs). A hospital acquired infection is an infection acquired in a hospital or other healthcare facility by a patient admitted for some reason other than that specific infection. Hospital acquired infections may include infections appearing 48 hours or more after hospital admission or within 30 days after discharge. They may also include infections due to transmission from colonized healthcare workers, or occupational exposure to infection among staff of the facility. Although the majority of hospital acquired infections are preventable, sadly their incidence has only increased.

Hospital acquired infections have become more rampant as antibiotic resistance spreads. Many factors contribute to the increased incidence of hospital acquired infections among hospital patients. For example, hospitals house large numbers of people who are sick and therefore have weakened immune systems. Medical staff move from patient to patient and see many patients a day, providing a way for pathogens to spread. Research indicates that hand hygiene practices are followed only 40% of the time by healthcare workers, even after exhaustive process improvements and training efforts. Many medical procedures, such as surgery, injections and other invasive procedures bypass the body's natural protective barriers, providing entry points for pathogens. The wide-spread use of antibiotics has contributed to the emergence of resistant strains of microorganisms in healthcare facilities and well as in the community.

Compliance with hand hygiene guidelines is considered the most effective action health care workers can take to reduce pathogen transmission in health care settings. Despite this, hand hygiene compliance remains low, and improvement efforts tend to lack sustainability.

SUMMARY

In general, the disclosure relates to systems and associated processes that monitor hand hygiene compliance. For example, the hand hygiene compliance system may monitor, analyze and report on hand hygiene compliance at a hospital or other healthcare facility.

In one example, the disclosure is direct to a system comprising one or more uniquely identified hand hygiene product dispensers, each associated with an area of concern (AOC) within a facility, that detects a dispense event and transmits a corresponding dispense event signal and dispenser identification information and one or more uniquely identified compliance badges, each of that receives the dispense event signal and the dispenser identification information and stores the dispenser identification information in a dispense event record that is associated with the detected dispense event.

In another example, the disclosure is directed to a system comprising at least one hand hygiene product dispenser, positioned within an area of concern (AOC) in a facility in which hand hygiene events are to be monitored, that senses a dispense event initiated by a wearer of a compliance badge and transmits dispenser data concerning the dispense event; and a plurality of compliance badges, each having uniquely associated badge identification information and each of which is worn by a different one of a plurality of wearers, the compliance badge comprising a receiver that receives the dispenser data and a controller that analyzes the dispenser data to monitor hand hygiene events initiated by the wearer.

In another example, the disclosure is directed to a system comprising at least one hand hygiene product dispenser, positioned within an area of concern (AOC) in a facility in which hand hygiene events are to be monitored, that senses a dispense event and transmits a dispense event signal indicative that a dispense event occurred and that transmits dispenser identification information and a compliance badge that receives the dispense event signal and the dispenser identification information associated with dispense events initiated by a wearer of the compliance badge, and stores dispense event records associated with each dispense event initiated by the wearer. The system may also include a plurality of compliance badges, each worn by a different one of a plurality of wearers. The system may also include one or more data gathering stations associated with the facility, each of which receives one or more of the dispense event records from at least one of the plurality of compliance badges; and a computing device that receives the dispense event records directly or indirectly from the one or more data gathering stations and analyzes the dispense event records to monitor hand hygiene events in the facility.

The details of one or more examples are set forth in the accompanying drawings and the description below. Other features and advantages will be apparent from the description and drawings, and from the claims.

BRIEF DESCRIPTION OF DRAWINGS

FIG. 5 is a schematic diagram illustrating the room components when a dispense event is detected.

FIGS. 6A-6C show example reports that may be generated by the reporting application.

FIG. 44A is a diagram illustrating another example hand hygiene compliance system.

FIG. 50 is a flowchart illustrating an example process by which a data gathering station may communicate with a compliance badge.

FIG. 51 is a flowchart illustrating an example process by which multiple dispense events satisfying a debounce condition may be counted as a single dispense event.

FIG. 52 is a block diagram illustrating another example hand hygiene compliance system.

DETAILED DESCRIPTION

Figure 1:
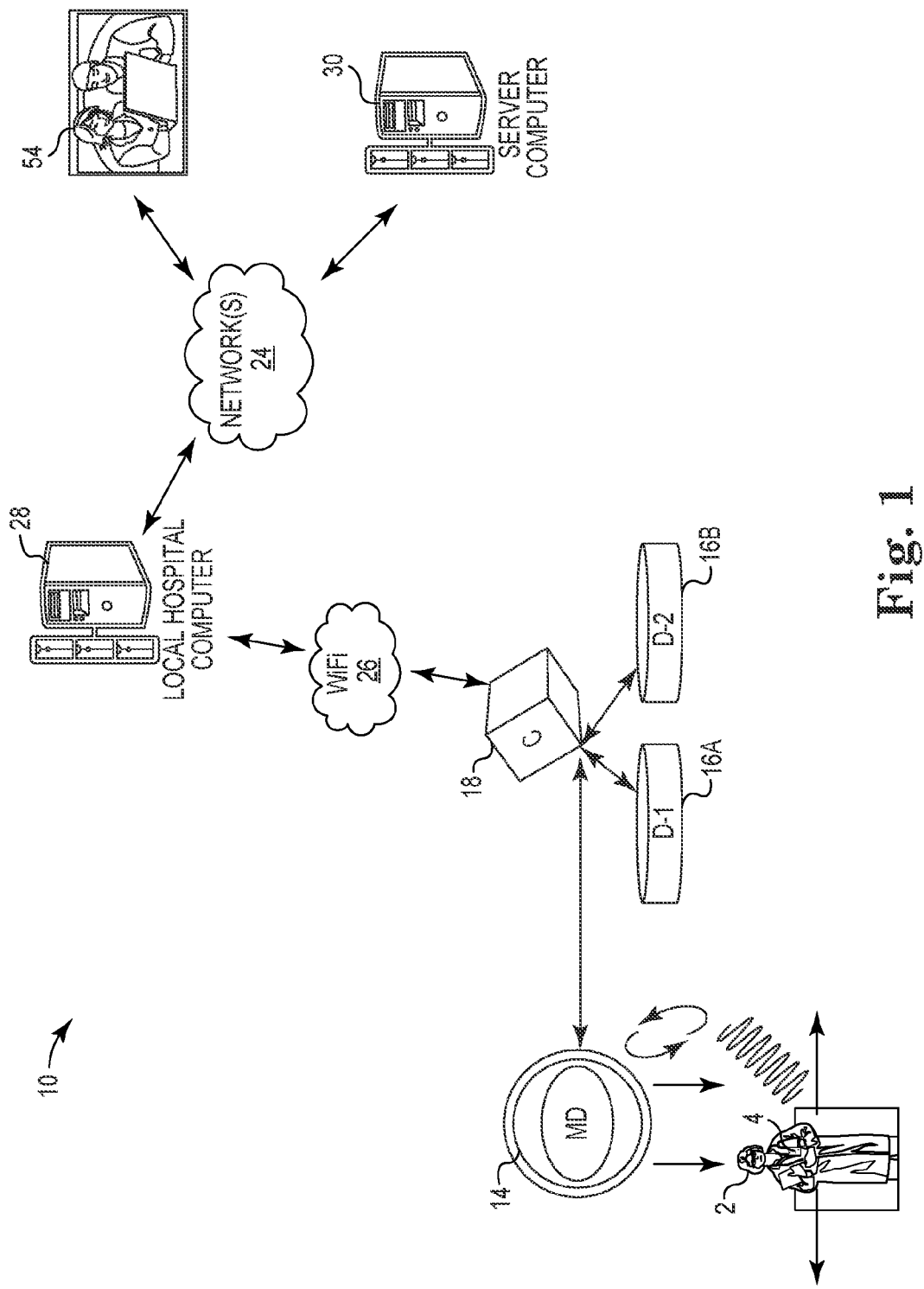
FIG. 1 is a block diagram illustrating an example hand hygiene compliance system.

In general, the disclosure relates to a system and associated processes that monitor hand hygiene compliance. For example, the hand hygiene compliance system may monitor, analyze and report on hand hygiene compliance at a hospital or other healthcare facility. FIG. 1 is a block diagram illustrating an example hand hygiene compliance system 10. FIG. 1 shows the components associated with one room or other defined space within a hospital. These room components include a motion detector module 14, one or more hand hygiene product dispensers 16 (shown here as hand hygiene product dispensers 16A and 16B, although more or fewer dispensers could be associated with each defined space), and a coordinator module 18. Also shown is a healthcare worker (HCW) 2 and an associated ID tag 4. Coordinator 18 communicates with a local hospital server 28 or other computer and with remote users 54 via one or more network(s) 24.

In general, hand hygiene compliance system 10 detects entry of persons into a patient room (or other defined area), identifying those persons and collecting data concerning their hand hygiene behavior. To that end, motion sensor 14 is physically installed near the door or entry to the defined space to detect entry of a person into that room or space (hereinafter referred to for simplicity as "room" or "patient room"). Motion sensor 14 includes an ID tag reader (not shown in FIG. 1) that is activated when entry of a person into the room is detected. ID tag 4 includes electronic circuitry (such as an RFID chip and antenna) that stores and communicates HCW identification information when interrogated by the reader. The entry information and the HCW identification information are transmitted to coordinator module 18. Alternatively, if the person entering the room is not an HCW and therefore does not have an associated id tag, the entry information and information identifying the person as a non-HCW are transmitted to coordinator module 18.

Upon receipt of the entry and identification information, coordinator module 18 may send a "wake-up" signal to dispensers 16A and 16B (and other dispensers in the room, if any). This wake-up signal may cause dispensers 16A and 16B to enter an "invitation mode", in which the dispenser activates one or more visual or audible indicators whose purpose is to remind the person entering the room of a hand hygiene opportunity. In some examples dispensers receives such wake-up signal directly from coordinator module 18. In other example the local hospital computer 28 support a hand compliance data base and sends such wake-up signal to dispensers.

Each dispenser 16 includes an activation sensor that detects when a hand hygiene product is dispensed. This is referred to as a "dispense event." For example, an activation sensor may detect when a dispenser button or bar is pushed or pulled to dispense hand hygiene product, may detect when an infrared or other touchless dispenser detects presence of a user, may detect the actual dispensing of the hand hygiene product, or may detect some other activation mechanism for dispensing hand hygiene product. Each time the activation sensor determines that dispenser 16 has dispensed hand hygiene product, the dispenser records a dispense event and looks for a HCW id tag signal containing HCW identification information from a target id tag 4 within range of the dispenser reader (or with non-HCW identification information if no ID tag data is detected).

The dispenser may use one or more of several techniques to obtain the HCW identification information from a target id tag 4, and/or to ensure that the correct HCW identification information associated with the entry event is isolated in the event that two or more tags respond. The HCW identification information associated with the dispense event, and any other relevant dispenser data regarding the dispense event, such as dispenser id, product name, time, date, etc., is transmitted to coordinator module 18.

Coordinator module 18 collects the hand hygiene data from motion sensor 14 and each of dispensers 16 in the associated room. In some examples, coordinator module 18 is AC powered and constantly turned ON and ready to receive information from the associated motion detector module 14 and dispensers 16. In this example, coordinator modules 18 for each room in the hospital may communicate with a local hospital computer 28 or other designated computer using a wireless protocol, such as a WiFi 26 or other wireless protocol. For example, coordinator module 18 may communicate the hand hygiene data to a local hospital computer 28 or other designated computer, such as one or more a designated hospital computers, a local or remote server computer, database, etc. via a wireless protocol, such as a WiFi 26 or other wired or wireless network. In other examples, coordinator module 18 may communicate directly with a server computer 30 or other computing device via any means of electronic communication.

Local computer 28 or other designated computer attempts to reconcile each entry event with a corresponding dispense event; that is, computer 28 determines whether each person that entered the room completed an associated dispense event. An entry event and a dispense event correspond when the same person initiated both the entry and the dispense event. This occurs when the same HCW identification information is associated with both the entry event and the dispense event. This may also occur when the entry event and the dispense event are associated with non-HCW identification information.

If a dispense event corresponding to an entry event is detected "compliant hand hygiene event" is recorded. If an entry event is detected and no corresponding dispense event is detected, computer 28 records a "non-compliant hand hygiene event." For example, computer 28 may determine whether a dispense event corresponding to an entry event is detected within a target time frame. The target time frame may be determined based on a reasonable amount of time for the identified person to get to one of the dispensers in the room, but not be so long as to result in a likelihood that the person associated with the entry event comes into contact with the patient without completing a dispense event. Target time frames may be in the range of 5 to 30 seconds, for example, but other time frames may be used and the disclosure is not limited in this respect.

A server computer 30 may communicate with the local computer 28 via network(s) 24 to receive the data related to hand hygiene compliance that is gathered and stored on local computer 28 at each hospital. Server computer 30 may also send commands, instructions, software updates, etc. to the hand hygiene compliance systems at each hospital via network(s) 24. Server computer 30 may receive data or otherwise communicate with the hand hygiene compliance systems at each of the hospitals 22 on a periodic basis, in real-time, upon request of server computer 30, or at any other appropriate time.

Server computer 30 includes analysis and reporting applications that analyze the hand hygiene data and generate reports regarding hand hygiene compliance. For example, server computer 30 may analyze the hand hygiene data to monitor hand hygiene compliance by individual HCW, type of HCW (e.g., nurses, doctors, environmental services (EVS), etc.), individual departments, type of department, individual hospital, type of hospital, across multiple hospitals, or by various other selected parameters. Server computer may generate a variety of reports to provide users local to each hospital 22A-22N or remote users 54 with both qualitative and quantitative data regarding hand hygiene compliance at their hospital, to compare data over time to determine whether improvement has occurred, and/or to benchmark hand hygiene compliance at multiple hospitals or other healthcare facilities.

In addition to sending entry event data and dispense event data to coordinator module 18, motion detector module 14 and dispenser module 16 may also periodically transmit status data to the coordinator module 18. For example, motion detector module 14 may transmit motion detector module status data, such as motion detector id, time, group name, battery voltage, constant and variable settings (detection range, etc.) at 0.5 second, 1 second, 2 seconds, 5 seconds or other appropriate time interval. Similarly, motion detector module 14 and/or dispenser module(s) 16 may transmit dispenser module status data, such as dispenser id, time, group name, battery voltage, constant and variable settings (detection range, hand hygiene product, number of dispenses, out-of-product status, refill status, etc.) at 0.5 second, 1 second, 2 seconds, 5 seconds or other appropriate time interval.

In addition, id tags 4 may be active, passive or semi-active tags. For example, id tags 4 may periodically generate a tag signal containing, for example, the HCW identification information, battery voltage, etc., at intervals such as 0.5 seconds, 1 second, 2 seconds, 5 seconds or other appropriate time interval. As another example, id tags 4 may continuously transmit a tag signal containing the HCW identification information. As another example, id tags 4 may be passive tags which generate a tag signal containing the HCW identification information when induced by an interrogation signal.

Figure 2:
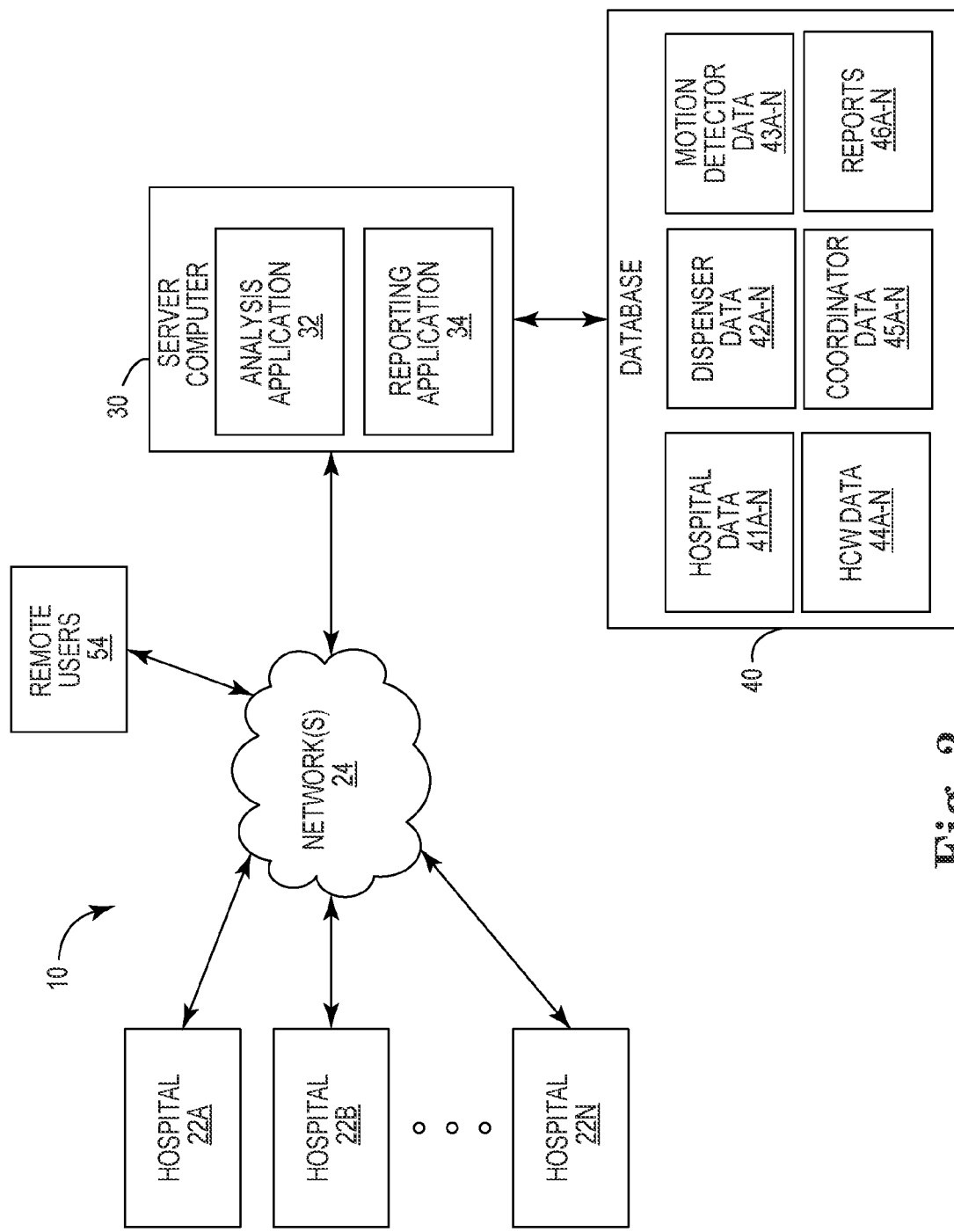
FIG. 2 is a block diagram illustrating an example communications environment within which the hand hygiene compliance system of the present disclosure may be used.

FIG. 2 is a block diagram illustrating an example communications environment within which the hand hygiene compliance system 10 of the present disclosure may be used. One or more hospitals or other healthcare facilities 22A-22N are coupled via network(s) 24 to server computer 30. Network(s) 24 may include, for example, one or more of a dial-up connection, a local area network (LAN), a wide area network (WAN), the internet, a cell phone network, satellite communication, or other means of electronic communication. The communication may be wired or wireless. Server computer 30 is coupled to a local server computer at each hospital 22A-22N via network(s) 24 to receive data related to hand hygiene compliance that is gathered and stored on local storage media at each hospital. Server computer 30 may also send commands, instructions, software updates, etc. to each hospital via network(s) 24. Server computer 30 may receive data or otherwise communicate with the hospitals on a periodic basis, in real-time, upon request of server computer 30, or at any other appropriate time.

The data received from hospitals 22A-22N, as well as other data associated with the operation of the hand hygiene compliance system, may be stored on a database 40. Database 40 may store, for example, hospital data 41A-41N associated with each of the hospitals 22A-22N, respectively; dispenser data 42A-42N associated with each of the hospitals 22A-22N, respectively; motion detector data 43A-43N associated with each of the hospitals 22A-22N, respectively; health care worker data 44A-44N associated with each of the hospitals 22A-22N, respectively; coordinator data 45A-45N associated with each of the hospitals 22A-22N, respectively; and reports 46A-46N associated with each of the hospitals 22A-22N, respectively.

Hospital data 41A-41N may include data that uniquely identifies or is associated with the respective hospital or other healthcare facility 22A-22N. As such, hospital data 41A-41N may include, for example, hospital identification information, employee information, management information, accounting information, business information, pricing information, information concerning those persons or entities authorized to access the reports generated by the hand hygiene compliance system, date and time stamps, caregiver identification, visitor identification and additional information relating to other aspects of the corporation or operation and other information specific to each individual hospital 22A-22N.

Dispenser data 42A-42N may include, for example, any information associated with operation of the hand hygiene product dispensers in the respective hospital 22A-22N. For example, dispenser data 42A-42N may include, without limitation, one or more of the following data types: dispenser id; dispenser type; dispensed product name; dispensed product type (e.g., sanitizer, soap, alcohol, etc.); dispensed product form (solid, liquid, powder, pelleted, etc.); dispensed product amounts (by volume, weight, or other measure); dispensing times, dates, and sequences; detected healthcare worker ids linked to specific dispensing events; empty dispenser indications; and other information originating at the dispenser site, whether detected by a dispenser or by an associated device.

Motion detector data 43A-43N may include, for example, information concerning the entry and exit of tagged persons from a hospital room or other defined area in the respective hospital 22A-22N. For example, motion detector data 43A-43N may include, without limitation, motion detector id; motion detector type; physical location (e.g., hospital room number, or other defined area within the hospital, such as a standalone hand washing station, procedure room, lab, common area, operating room, etc.; date of installation; maintenance records; detected person events, whether id tagged or untagged; detected healthcare worker ids; date and time stamps; and other data associated with the motion detector modules of the respective hospital 22A-22N. Healthcare worker (HCW) data 44A-44N may include, for example, information concerning employees of the respective hospital 22A-22N. For example, HCW data 44A-44N may include, without limitation, HCW name, employee id number and/or other identification information; position (physician, nurse, physician assistant, physical therapist, EVS, etc.); work schedule; and other HCW related information for the healthcare workers in the respective hospital 22A-22N.

Coordinator data 45A-45N may include, for example, all of the information collected by the coordinator modules in the respective hospital 22A-22N. For example, coordinator data 46A-46N may include, without limitation, coordinator ids; a lists of hand hygiene dispensers associated with each coordinator; lists of motion detector modules associated with each coordinator; a list of room(s) or other defined area(s) within the hospital associated with each coordinator; links to the data collected by the dispensers and motion detector modules associated with each coordinator; and other coordinator information for each coordinator in the respective hospital 22A-22N.

Server computer 30 includes an analysis application 32 that analyzes the data received from each of hospitals 22A-22N and stores the results for each hospital 22A-22N in the database 40. Analysis application 32 may analyze the hospital data 41A-41N, dispenser data 42A-42N, motion detector data 43A-43N, HCW data 44A-44N, and/or coordinator data 45A-45N either alone or in various combinations with each other to monitor hand hygiene compliance by individual HCW, type of HCW (e.g., nurses, doctors, EVS, etc.), individual departments, type of department, individual hospital, type of hospital, across multiple hospitals, or by various other selected parameters.

A reporting application 34 generates a variety of reports that present the analyzed data for use by the person(s) responsible for overseeing hand hygiene compliance at each hospital 22A-22N. Reporting application 34 may generate a variety of reports to provide users local to each hospital 22A-22N or remote users 54 with both qualitative and quantitative data regarding hand hygiene compliance at their hospital, and/or to compare data over time to determine whether improvement has occurred. Reporting application 34 may also allow users to benchmark hand hygiene compliance at multiple hospitals or other healthcare facilities.

Reports 46A-46N associated with each hospital 22A-22N, respectively, may also be stored in database 40. Examples of the reports that may be generated by reporting application 34 are described with respect to FIGS. 6A-6C. Reports 49A-49N may be accessed by users local to each hospital 22A-22N or by remote users 54 over one or more network(s) 24. One or more of the reports 49A-49N may be downloaded and stored on a local hospital computer, such as hospital server computer 23 shown in FIG. 1, user computer 54, other authorized computing device, printed out in hard copy or further communicated to others as desired.

Local hospital computer 28 (FIG. 1) or database may also store the above-described hand hygiene data (e.g., hospital data, dispenser data, motion detector data, HCW data, and/or coordinator data) associated with that hospital. Hospital computer 28, database, or other local computer(s), may also include local analysis and reporting applications such as those described above with respect to analysis and reporting applications 32 and 34. In that case, reports associated with that particular hospital may be generated and viewed locally, if desired. In another example, all analysis and reporting functions are carried out remotely at server computer 30, and reports may be viewed, downloaded or otherwise obtained remotely. In other examples, some hospitals 22 may include local storage and/or analysis and reporting functions while other hospitals 22 rely on remote storage and/or analysis and reporting. Thus, although the general case of data being stored at the local hospital computer 28 and analysis/reporting being carried out by the server computer 30 is described herein, it shall be understood that these storage, analysis and reporting functions may also be carried out locally or at some other location, and that the disclosure is not limited in this respect.

Figure 3:
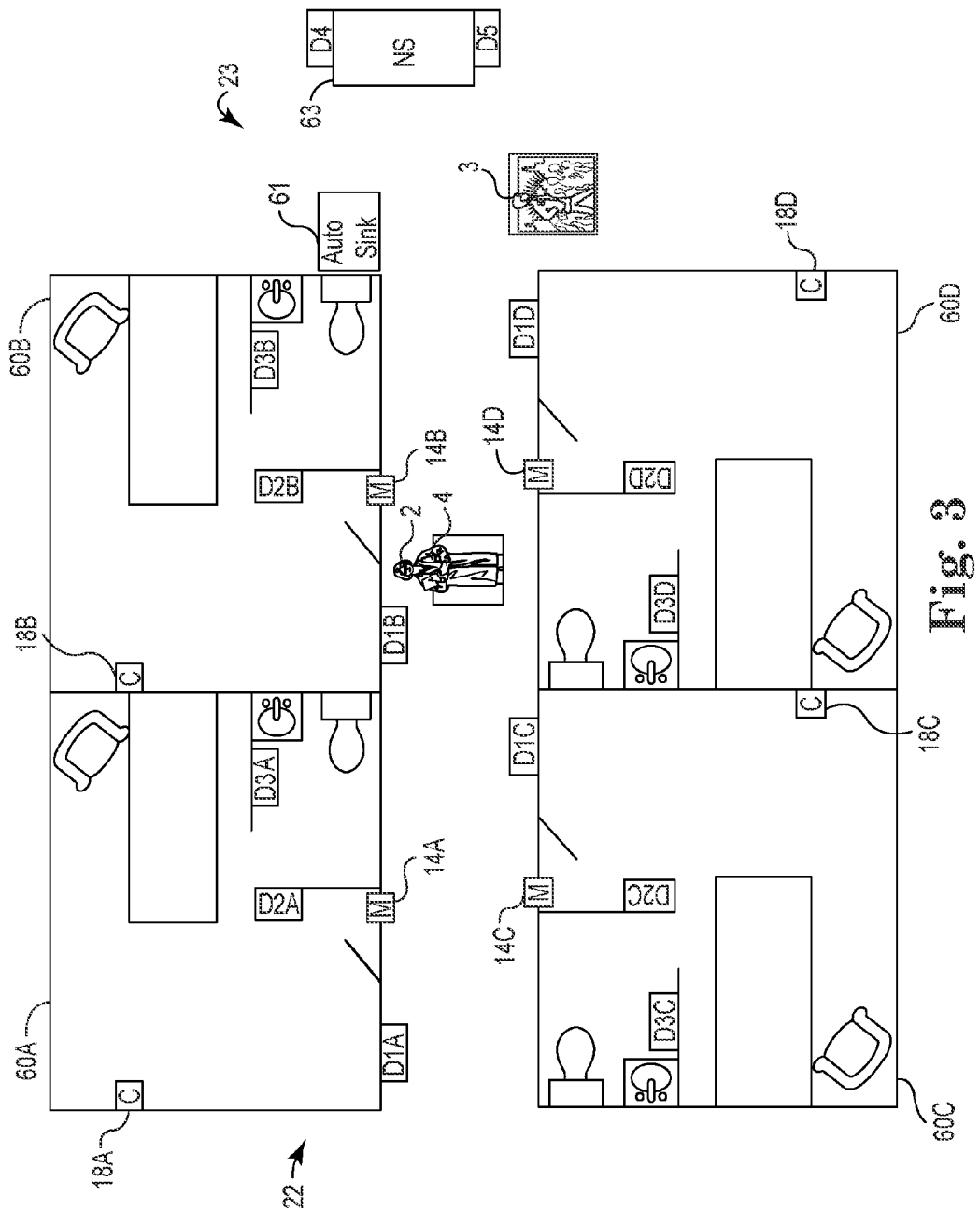
FIG. 3 is a schematic diagram illustrating and example installation of hand hygiene system components in multiple rooms and common areas of a hospital.

FIG. 3 is a schematic diagram illustrating and example installation of hand hygiene system components in multiple rooms and common areas of a hospital 22. In this example, hospital 22 includes patient rooms 60A-60D and common area 23. Each patient room 60 includes one or more dispensers; in this example, each patient room includes three dispensers labeled D1A-D3A, D1B-D3B, D1C-D3C, and D1D-D3D for each patient room 60A-60D, respectively. In this particular example, dispensers D1 and D2 may be room associated alcohol sanitizer dispensers, dispensers D3 may be room associated soap dispenser, dispenser D4 may be a common area alcohol sanitizer dispenser, and dispenser D5 may be a common area soap dispenser. Dispensers D4 and D5 should be assigned to one of the room coordinator modules 18, for example to the coordinator module 18D. In some cases for common area dispensers a separate coordinator module 18 should be designated. It shall be understood that each room or defined space could have more or fewer dispensers, or different combinations of these or other types of dispensers, and that the disclosure is not limited in this respect.

Each patient room 60A-60D also includes a motion detector module 14A-14D and coordinator module 18A-18D, respectively. Common area 23 includes automated hand washing sink 61, nurses station 63 and dispensers D4 and D5. One or more HCWs, such as HCW 4, each having an associated electronically readable id tag 4 is present within hospital 22. Also present within hospital 22 are one or more non-HCW persons 3 (e.g., patients, visitors, etc.), who do not have associated id tags.

Although certain examples are shown and described herein, it shall be understood that the number of motion detectors, interrogators and coordinator modules deployed in any particular hand hygiene system may vary depending upon the number and location of rooms and other defined spaces within the hospital, the number and location of dispensers, the communication ranges of the devices, their power requirements, etc. It shall be understood, therefore, that the number of motion detector modules, interrogators and coordinator modules may vary depending upon the hospital architecture and the particular system implementation and that the disclosure is not limited in this respect.

Figure 4:
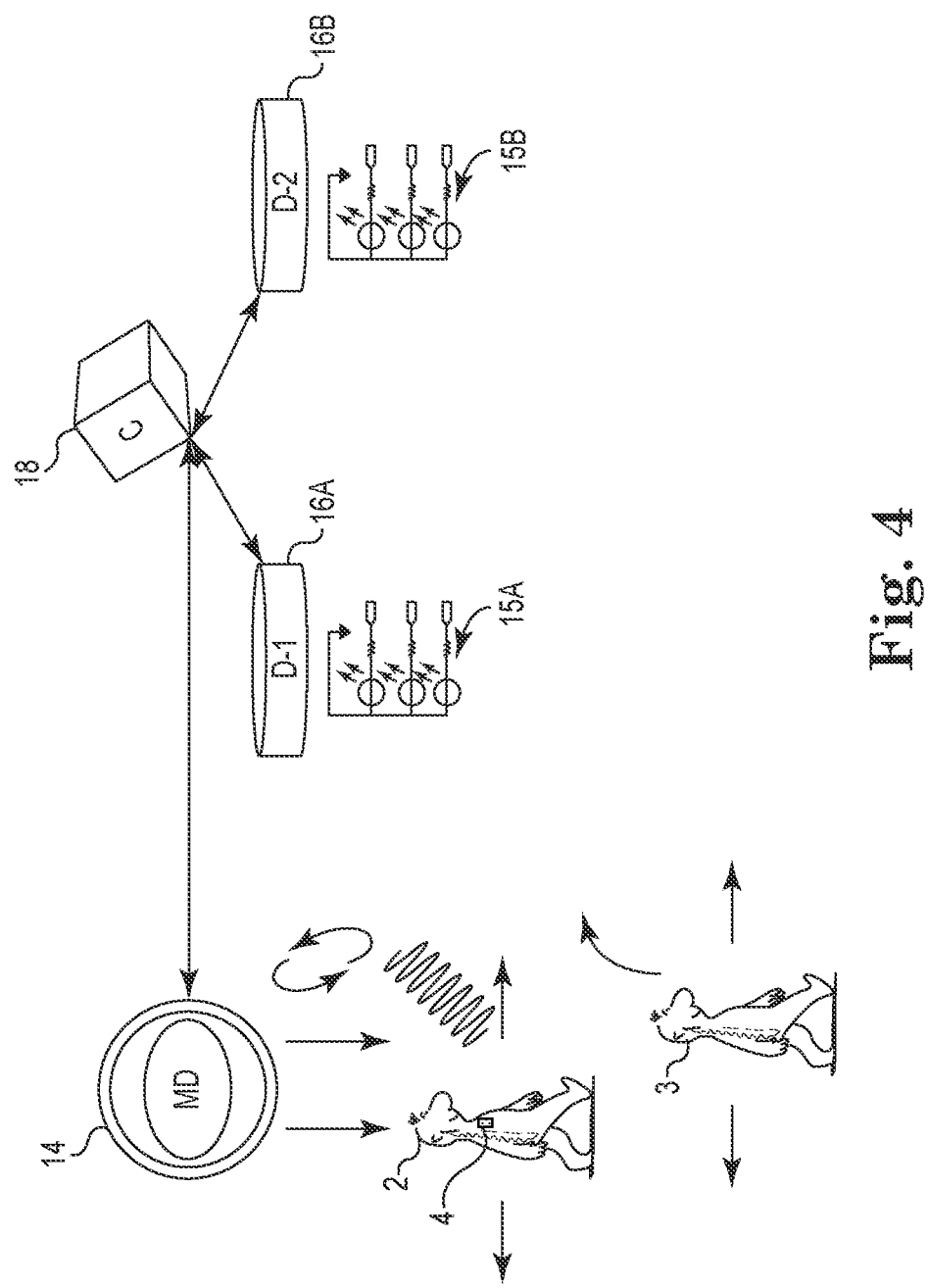
FIG. 4 is a schematic diagram illustrating the room components when a person is detected entering a room or other defined space.

FIG. 4 is a schematic diagram illustrating the room components when a person is detected entering a room or other defined space. When an id tagged HCW 2 enters a room having the components of the hand hygiene compliance system installed, motion detector module 14, which in some examples is installed near the door or entry to the room or other defined space, senses entry of the person 2 into the room. This is termed an "entry event." When an entry event is detected, an interrogator within motion detector module 14 looks for a HCW id tag signal and obtains the HCW identification information from any HCW id tags within range.

In one example, electronically readable id tags 4 are implemented using radio frequency identification (RFID) transponders or tags. The typical RFID tag includes an integrated circuit chip that stores HCW identification information and an antenna that generates a HCW id tag signal that includes the HCW identification information. RFID tags may be active, passive or semi-passive and may operate at any appropriate frequency. RFID tags may also be read-only, read/write or a combination. In other examples, electronically readable id tags 4 may be implemented using other mechanisms for electronically storing and conveying product information, such as bar codes, conductive inks, printed circuits, etc. Thus, although the phrase "electronically readable label" is used throughout this specification, it shall be understood that any electronically readable medium that may be used to store and convey information that is known or will be known to those of skill in the art may be used and that the disclosure is not limited in this respect.

Motion detector module 14 captures product information from the electronically readable HCW id tag 4 and passes the data to the associated coordinator module 18. In the RFID example, motion detector module 14 may include a radio frequency (RF) transmitter and receiver, controlled by a microprocessor or digital signal processor. The RFID module includes an antenna that receives HW id tag signals from HCW id tags within range. The HCW id tag signal includes the HCW identification information from HCW id tag 4 and may also include motion detector id information, time and date of the entry event, etc.

When a non-HCW person enters a room or other defined space, an entry event will be detected but no HCW identification information will be received. This is because non-HCW persons such as patients, visitors, delivery personnel, or other persons, do not have electronically readable id tags. Thus, when a person enters a room and no HCW identification information is received, the detected entry event is associated with a non-HCW identification information to the entry event. In this way, the system is able to distinguish between entry of a HCW and entry of non-health care workers. Also, the system is able to accurately monitor hand hygiene compliance by HCWs and discriminate between hand hygiene events by HCWs and hand hygiene events by non-HCWs.

Upon receipt of the entry event, coordinator module 18 may send a "wake up" signal to each of dispensers 16 within the room or other defined space. Upon receipt of the wake up signal, dispensers 16 may activate one or more audible or visual hand hygiene opportunity indicators 15A and 15B, respectively, the purpose of which is to remind the HCW or non-HCW who entered the room of hand hygiene opportunities within the room.

FIG. 5 is a schematic diagram illustrating the room components when a dispense event is detected. As discussed above, each dispenser 16 includes an activation sensor that detects each time that hand hygiene product is dispensed (a "dispense event"). The dispenser (dispenser 16A in the example of FIG. 5) records a dispense event and detects the HCW identification information from an id tag 4 within range of the dispenser reader. If no HCW identification information is detected, the dispenser (dispenser 16B in this example of FIG. 5) assumes that the dispense event was caused by a non-HCW 3 and associates the dispense event with a non-HCW identifier. This dispense event data, HCW identification information or non-HCW identifier, and any other relevant dispenser data regarding the dispense event, such as dispenser id, product name, time, date, etc., is transmitted to coordinator module 18.

Figure 6A:
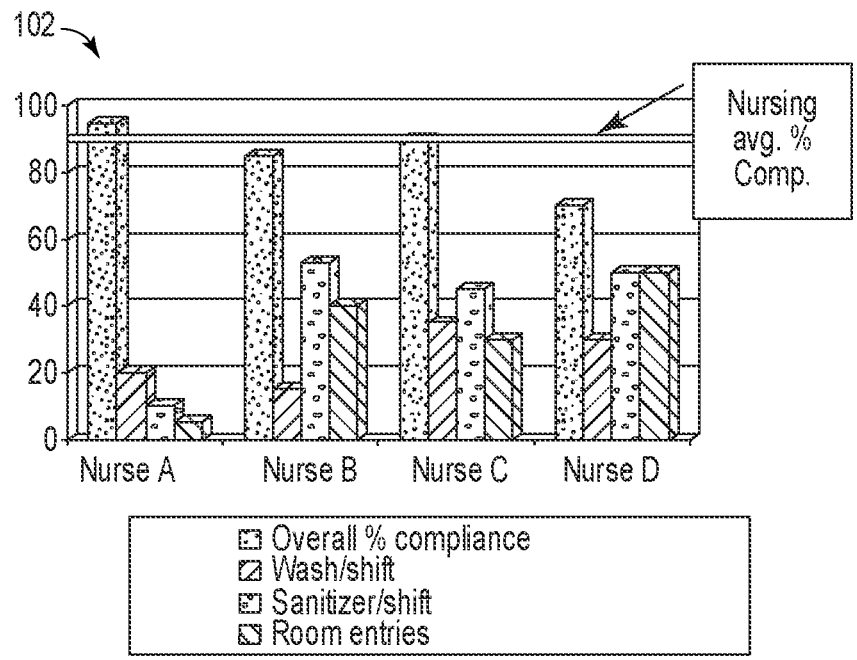
Figure 6B:
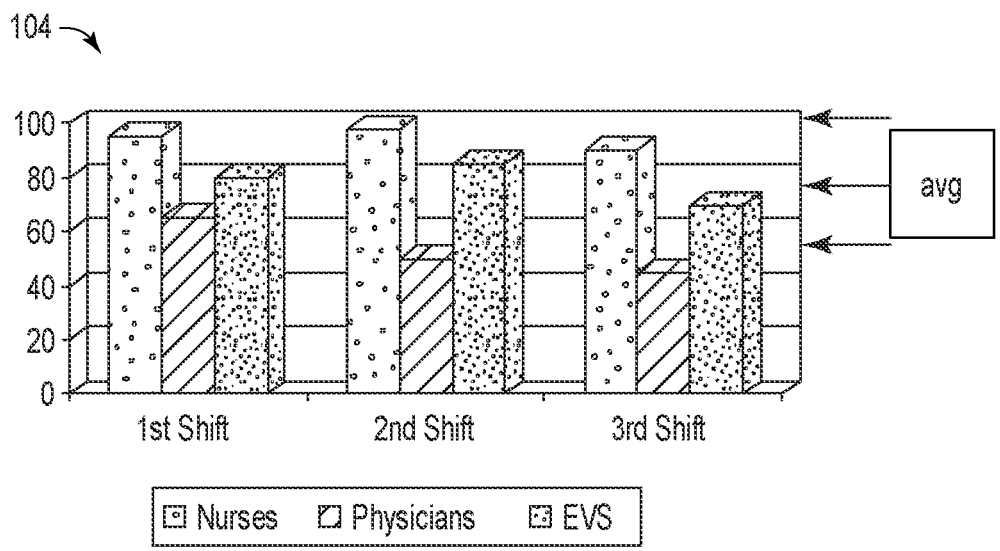

FIGS. 6A-6C show example reports that may be generated by reporting application 34. The reports may be requested and presented in a variety of ways, including text reports, graphs, tables, etc. Reporting application 34 may permit the user to request reports that convey the data in a variety of different ways. For example, reporting application 34 may permit a user to select a particular format (text, graphs, tables, combinations thereof, etc.); select by data type (dispenser data, hospital data, motion detector data, HCW data, coordinator data, etc.); select by date; select by individual HCW type of HCW, department, hospital or multiple hospitals; select by percent compliance; select for example, by highest, lowest or average compliance; or to create and generate reports based on nearly any data collected and stored by hand hygiene compliance system.

These reports may include, for example, detailed analysis and reporting on key metrics, including hand hygiene compliance by individual HCW, type of HCW (nurses, doctors, EVS, etc.), department, type of department, individual hospital, across multiple hospitals, etc. The reports may benchmark current hand hygiene practices across the entire database, across hospitals or other healthcare facilities. The reports may include trending of various key metrics over time, identify particular problem areas (e.g., individual HCW or types of HCW having unsatisfactory hand hygiene compliance) provide actionable improvement plans and assess current practices relative to best hand hygiene practices. It shall be understood that the reports shown in FIGS. 6A-8C are exemplary only, and that other reports may also be generated, and the disclosure is not limited in this respect.

FIG. 6A, for example, illustrates an example compliance report 102. Report 102 details hand hygiene compliance by individual (nurses A-D in this example). Report 102 shows the overall percentage compliance, wash/shift compliance, sanitizer/shift compliance and the number of room entries for each nurse A-D. Report 102 also shows the average percent compliance among these four individual nurses. Report 102 could also show the aver percent compliance among all nurses in a particular department or in a particular hospital, etc.

FIG. 6B, for example, illustrates another example compliance report 104. Report 104 details hand hygiene compliance by shift and by function. For example, report 104 shows the percent compliance for each of three shifts (shift 1, shift 2 and shift 3) for three types of HCWs (nurses, physicians and EVS). Report 104 also shows the aver percent compliance for each type of HCW.

FIG. 6C, for example, illustrates an example maintenance report 106. Report 106 details the status of several dispensers (identified as W231, W255, W375 and E515 in this example). For example, report 106 shows the product status (that is, the relative amount of product remaining in the dispenser). In this example, the status is shown as "OK" for dispenser W231, meaning that dispenser does not need to be refilled at this time. The status is shown as "Low" for dispensers W255, W375 and E515, meaning that those dispensers need to be refilled in the near future. Report 105 also shows the product type for each dispenser and the battery status for each dispenser. A battery status of "Low" means that the batteries should be replaced and a battery status of "OK" means that the batteries do currently not need to be replaced.

Other reports that may be generated may include, for example, summary reports for an entire hospital or other healthcare facility; the total number of dispense events per dispenser over a defined period of time; the total compliance percent for all HCWs by patient room or other defined area, by department, by hospital, or across multiple hospitals; baseline compliance thresholds by individual HCW, type of HCW, by department, by hospital, or multiple hospitals; reports comparing highest, lowest and/or average percentage compliance by any of these breakdowns; reports comparing highest, lowest and/or average number of dispense events per dispenser or per HCW; trending data showing past, present and projected future hand hygiene compliance;

The reports may indicated whether the number of dispense events per dispenser, per room, per individual HCW, per HCW type, per department, per hospital etc. is within acceptable limits and whether it met specified targets for dispense events for each of these parameters.

The reports may highlight particular problems areas where hand hygiene compliance thresholds are not being met. For example, the reports may identify certain individual HCWs, types of HCWs, departments or hospitals having hand hygiene compliance below a specified threshold. This information can help to identify where additional training or corrective action may be necessary.

The reports may also provide a summary of recommended next steps that the hospital may take to improve their hand hygiene compliance results in the future. For example, suggested next steps may be given for continuous improvement and education directed toward individual HCWs or types of HCWs, operational processes, hand hygiene outcome efficiency, etc.

Figure 7:
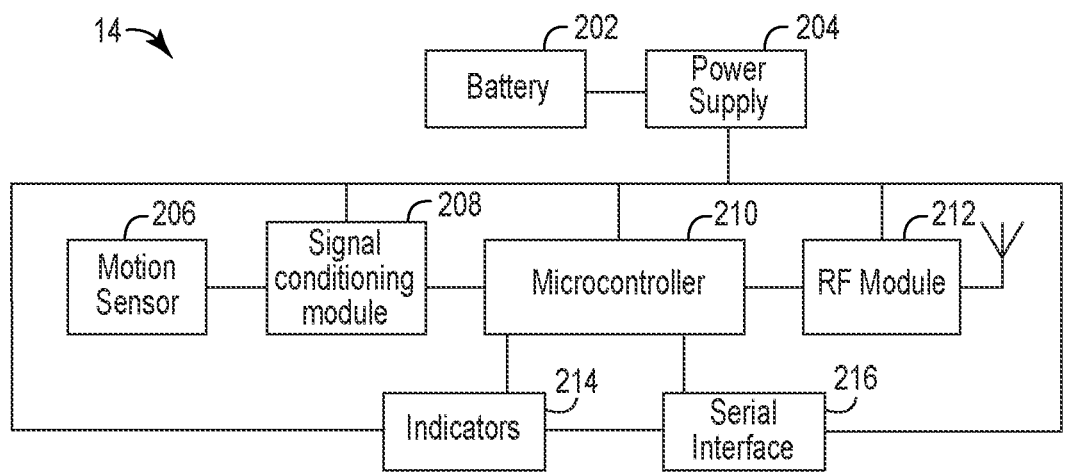
FIG. 7 is a block diagram illustrating an example implementation of a motion detector module.

FIG. 7 is a block diagram illustrating an example implementation of a motion detector module 14. In this example, motion detector module 14 includes a battery 202, a power supply 204, a motion sensor 206, a signal conditioning module 208, a microcontroller 210, an RF module 212, a serial interface 216 and indicators 214. Motion detector module 14 may be a standalone unit placed close to the entrance of a patient room or other defined space. Motion detecting capabilities are provided by motion sensor 206. Motion sensor 206 may have the capability to distinguish incoming persons entering the room and outgoing persons leaving the room. One such motion sensor is the pyroelectric detector PIR 325, available from Glolab Corp, Wappingers Falls, N.Y. However, it shall be understood that other motion sensors could be used and that the disclosure is not limited in this respect. For example, motion sensor 206 could also be implemented using ultrasonic or other type of motion sensing technology.

RF module 212 provides for wireless communication between motion detector module 14 and coordinator module 18. For example, RF module 212 may be implemented using wireless module eZ430RF2500T using the SimpliciTI wireless communication protocol, available from Texas Instruments, Inc., Dallas, Tex. However, it shall be understood that other wired or wireless communication modules and/or protocols could be used and that the disclosure is not limited in this respect.

Indicators 214 may be audible indicator such as a speaker or visible indicators such as LEDs, displays, etc. Indicators 214 may indicate the status of battery 202 or active/inactive status of RF module 212, or other status of motion detector module 14.

Microcontroller 210 includes software modules (described below) that control detection of entry events and communication between motion detector module 14 and coordinator module 18.

Figure 8:
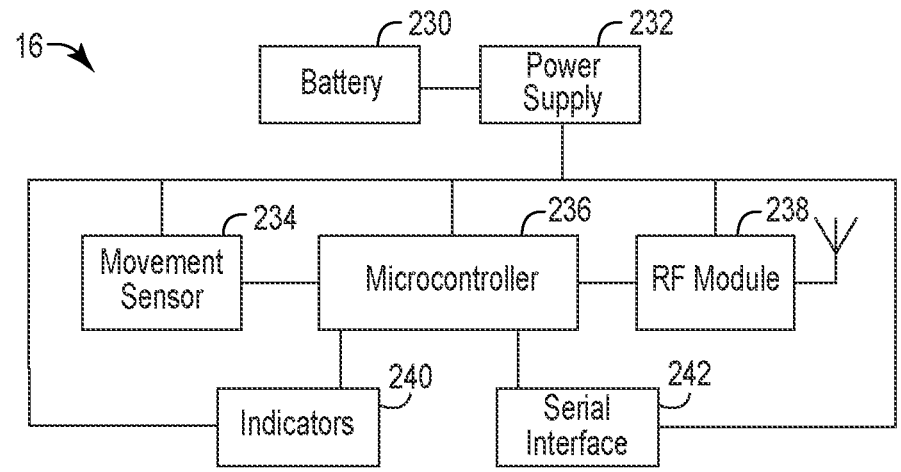
FIG. 8 is a block diagram illustrating an example implementation of a dispenser electronics module.

FIG. 8 is a block diagram illustrating an example implementation of a dispenser electronics module 16. In this example, dispenser module 16 includes a battery 230, a power supply 232, an activation sensor 234, a microcontroller 236, an RF module 238, a serial interface 242 and indicators 240. Activation sensor 234 detects dispense events. For example activation sensor may be implemented using a photo interrupter, a flex sensor, acceleration sensor, IR interrupter, IR reflectance sensor, or other mechanism for detecting mechanical movement of a dispenser button or bar when activated by a user, detecting movement of a dispensing mechanism that actually causes the hand hygiene product to be dispensed, optically detecting such mechanical movement(s) or optically detecting movement of dispensed product, etc.

RF module 238 provides for wireless communication between dispenser module 16 and coordinator module 18. For example, RF module 238 may be implemented using the same wireless module described above with respect to motion detector module 14, that is, the eZ430RF2500T using the SimpliciTI wireless communication protocol, available from Texas Instruments, Inc., Dallas, Tex. However, it shall be understood that other wired or wireless communication modules and/or protocols could be used and that the disclosure is not limited in this respect.

Dispenser indicators 240 may include audible or visual indicators activated during invitation mode, and/or may also include status indicators such as battery status, remaining product status (e.g., whether the dispenser needs to be refilled with hand hygiene product), or other relevant indication of dispenser status.

Microcontroller 236 includes software modules (described below) that control detection of dispense events and communication between dispenser module 16 and coordinator module 18. For example, microcontroller receives an activation signal from activation sensor 234, generates a record of a dispense event and corresponding time stamp and HCW or non-HCW identification information.

Figure 9:
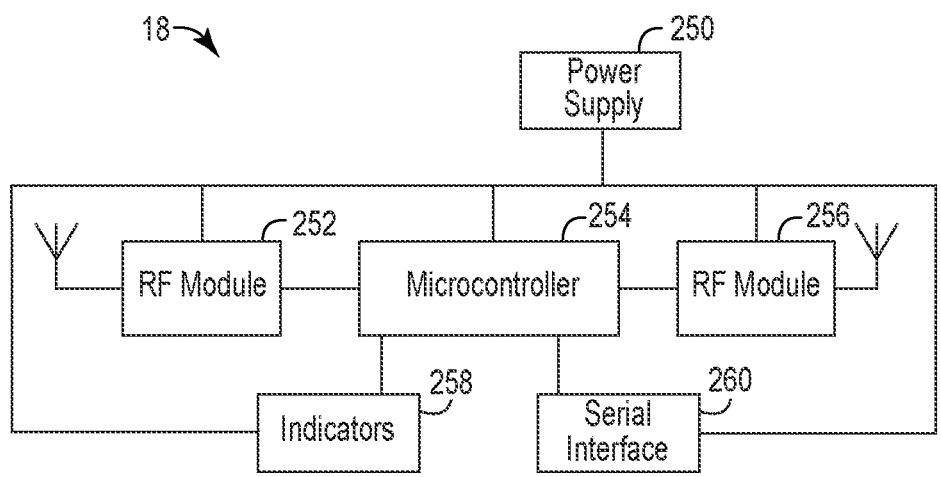
FIG. 9 is a block diagram illustrating an example implementation of a coordinator module.

FIG. 9 is a block diagram illustrating an example implementation of a coordinator module 18. In this example, coordinator module 18 includes a power supply 250, an RF module 252, a microcontroller 254, a second RF module 256, a serial interface 260 and indicators 258. Power supply 250 of coordinator module 18 may be obtained from an AC wall power outlet.

RF module 256 provides for wireless communication between coordinator module 18 and the associated motion detector module 14 and dispenser modules 16. For example, RF module 256 may be implemented using the same wireless module described above with respect to motion detector module 14 and dispenser module 16, that is, the eZ430RF2500T using the SimpliciTI wireless communication protocol, available from Texas Instruments, Inc., Dallas, Tex. However, it shall be understood that other wired or wireless communication modules and/or protocols could be used and that the disclosure is not limited in this respect.

In this example, RF module 252 provides for wireless communication between coordinator module 18 and local hospital computer 28 or other designated computer or database. For example, RF module 252 may be implemented using WiFi module RFD 21715 available from RF Digital, Irvine, Calif. However, it shall be understood that other wired or wireless communication modules and/or protocols could be used and that the disclosure is not limited in this respect.

Microcontroller 254 includes software modules (described below) that control detection of compliant and non-compliant events and communication between coordinator module 18 and motion detector module 14, dispenser modules 16, local hospital computer 28 and/or other remote communication. For example, microcontroller receives entry events and dispense events, determines whether compliant or non-compliant hand hygiene event occurred, and communicates data concerning entry events, dispense events, compliant hand hygiene events, non-compliant hand hygiene events, coordinator status, motion detector status and/or dispenser status to local hospital computer 28 or other designated computer, server or database.

Figure 10:
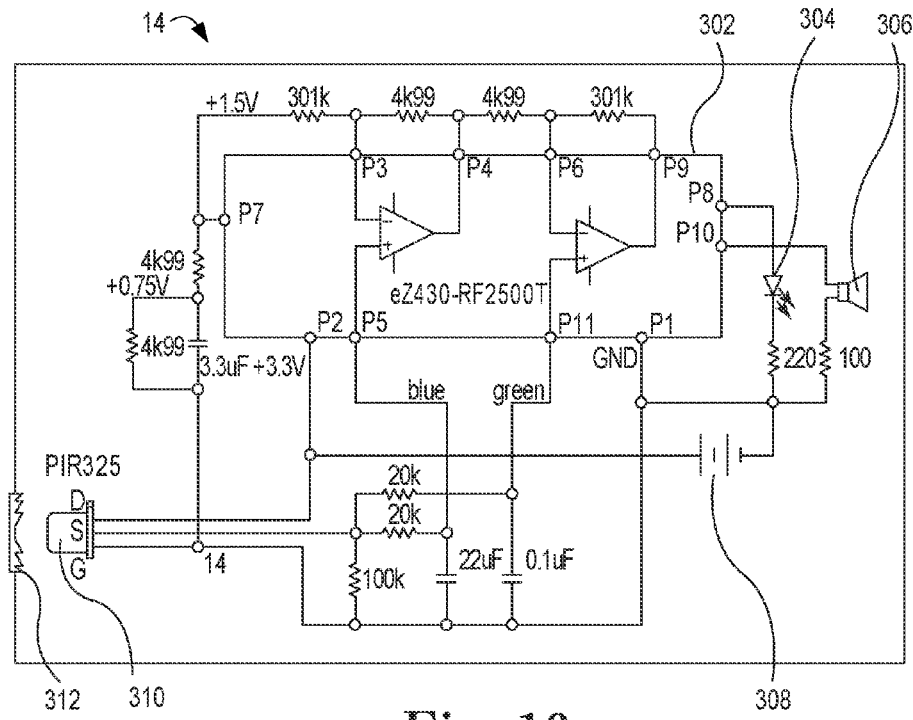
FIG. 10 is a schematic diagram illustrating an example implementation of a motion detector module.

FIG. 10 is a schematic diagram illustrating an example implementation of a motion detector module 14. Motion detector 14 includes a wireless module 302 (eZ430RF2500T using the SimpliciTI wireless communication protocol, available from Texas Instruments, Inc., Dallas, Tex.), visible indicator(s) 304, audible indicator(s) 306, batteries 308, motion sensor 206 (pyroelectric detector PIR 325, available from Glolab Corp, Wappingers Falls, N.Y.), and fresnel lens (available from Glolab Corp., Wappingers Falls, N.Y., for example).

Figure 11:
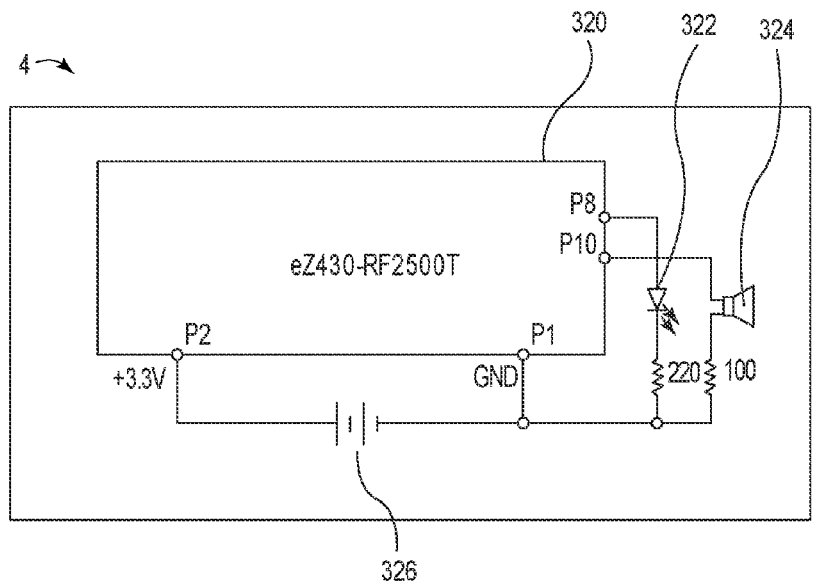
FIG. 11 is an electrical schematic diagram illustrating an example implementation of an id tag.

FIG. 11 is an electrical schematic diagram illustrating an example implementation of an id tag 4. In this example, id tag 4 includes RF module 320 (eZ430RF2500T using the SimpliciTI wireless communication protocol, available from Texas Instruments, Inc., Dallas, Tex.). ID tag 4 also includes visible indicator 322 and/or audible indicator 324. In this example, when an entry event is detected, coordinator 18 may send a "wake up" signal to id tag 4, causing id tag 4 to enter a "reminder mode" in which visible or audible signals serve to remind the person associated with the entry event of a hand hygiene opportunity. However, it shall be understood that ID tag 4 need not include indicators 322/324, nor need it include a reminder mode, that the reminder mode/indicators may be implemented or not depending upon the requirements of the particular hospital, and that the disclosure is not limited in this respect.

Figure 12:
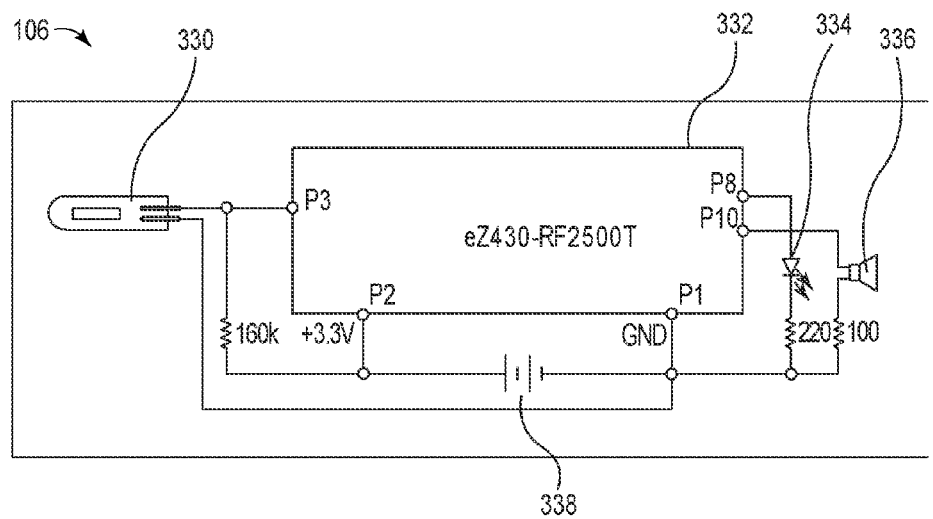
FIG. 12 is an electrical schematic diagram illustrating an example implementation of a dispenser module.

FIG. 12 is an electrical schematic diagram illustrating an example implementation of a dispenser module 16. In this example, dispenser module 16 includes RF module 332 (eZ430RF2500T using the SimpliciTI wireless communication protocol, available from Texas Instruments, Inc., Dallas, Tex.), a flex sensor 330, visible indicator(s) 334, audible indicator(s) 336, and batteries 338. Flex sensor 330 may be implemented using a flexible sensor such as those available from Flexpoint Sensor Systems, Inc. Draper, Utah (www.flexpoint.com).

Figure 13:
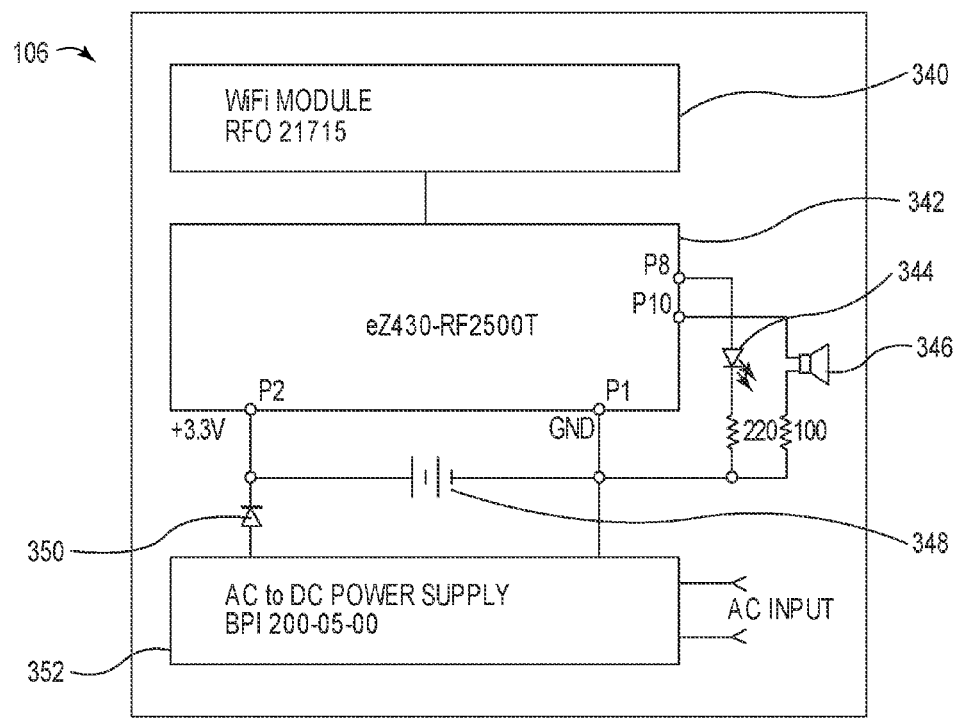
FIG. 13 is an electrical schematic diagram illustrating an example implementation of a coordinator module.

FIG. 13 is an electrical schematic diagram illustrating an example implementation of a coordinator module 18. In this example, coordinator module 18 includes a WiFi module 340 (WiFi module RFD 21715 available from RF Digital, Irvine, Calif.), RF module 342 (eZ430RF2500T using the SimpliciTI wireless communication protocol, available from Texas Instruments, Inc., Dallas, Tex.), visible indicator(s) 344, audible indicator(s) 346, batteries 348, diode 350 and AC to DC Power supply 352 (such as BPI 200-05-00 available from BIAS Power, Buffalo Grove, Ill.).

Figure 14:
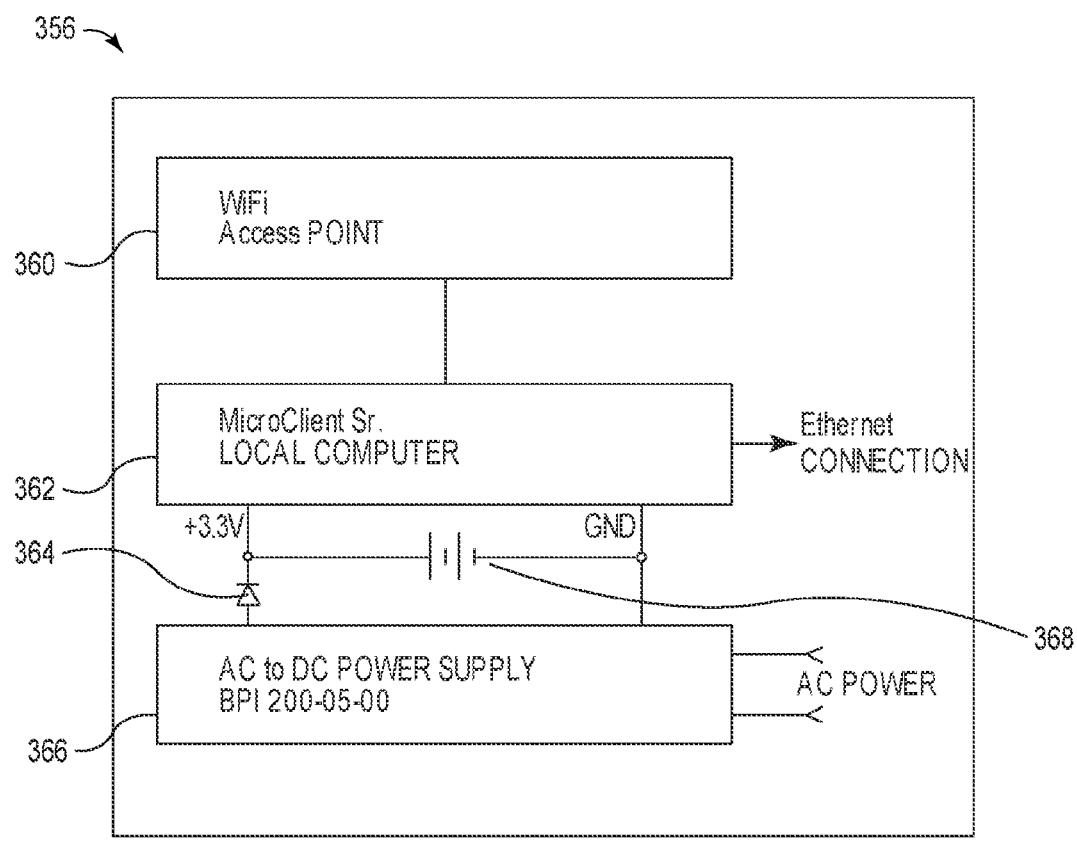
FIG. 14 is an electrical schematic diagram illustrating an example implementation of a local hospital computer or other designated computer having a WiFi access point.

FIG. 14 is an electrical schematic diagram illustrating an example implementation of a WiFi access point for local hospital computer 28 or other designated computer. In this example, a WiFi access point 260 (WiFi Access point model WRT 610N (available from Linksys, Irvine, Calif.) provides for wireless communication between local hospital computer 362 or other designated computer and all of the coordinators 18 in the hand hygiene compliance system. Power is provided via an AC to DC power supply 366.

Figure 15:
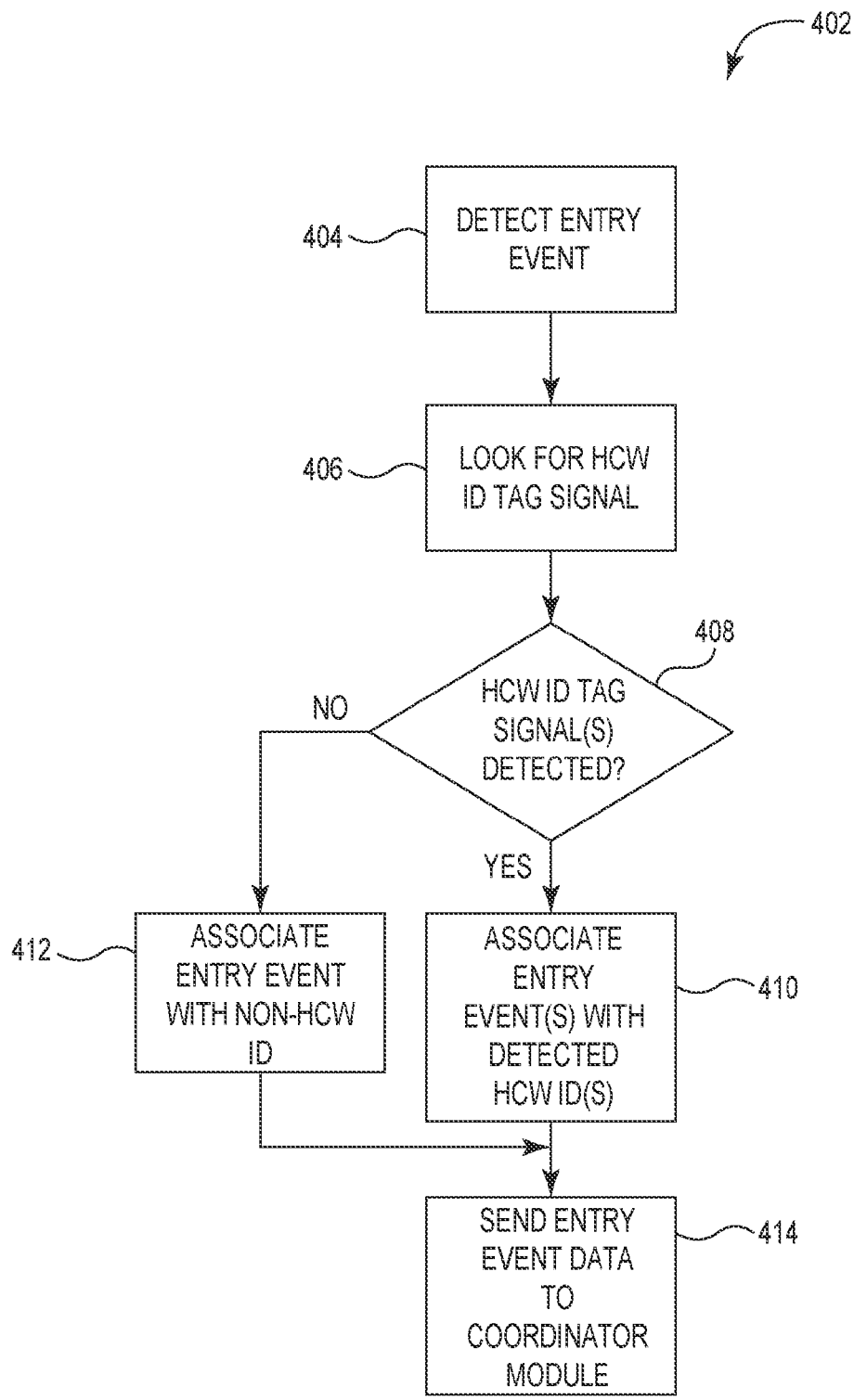
FIG. 15 is a flowchart illustrating an example process of operation for a motion detector module.

FIG. 15 is a flowchart illustrating an example process of operation for motion detector module 14. Motion detector module 14 detects an entry event (404). Motion detector module 14 then attempts to communicate with a HCW id tag 4 within a predefined range (406). For example, the range of motion detector module 14 may be from 0-3 meters. In general the range of motion detector module 14 may be determined so that only the HCW id tag 4 that caused the entry event is detected, rather than other HCW id tags not associated with the entry event, such as those that may already be present in the room.

In one example, when waiting for an entry event to occur, motion detector module 14 may look for HCW id tag signals at periodic intervals such as 0.5 second, 1 second, 2 seconds, 5 seconds or other appropriate time interval. Once motion detector module 14 detects an entry event, it may enter a continuous mode as it attempts to communicate with any HCW id tags 4 within range. Operation of motion detector module 14 in this way may serve to reduce power consumption and preserve battery life. It shall be understood, however, that motion detector module 14 need not operate this way, and that the disclosure is not limited in this respect. For example, motion detector module 14 could operate continuously at all times, periodically at all times, or some other combination of continuous and periodic operation.

If motion detector module 14 detects a HCW id tag signal (408), it associates the entry event with the detected HCW identification information (410) and sends the entry event data (including the HCW id, time, voltage, signal strength, and any other related information) to coordinator module 18 (414). If motion detector module 14 does not detect a HCW id tag signal within a predetermined period of time (408), motion detector module 14 associates the entry event with a non-HCW identification information (412) and sends the entry event data to the coordinator module (414).

Figure 16:
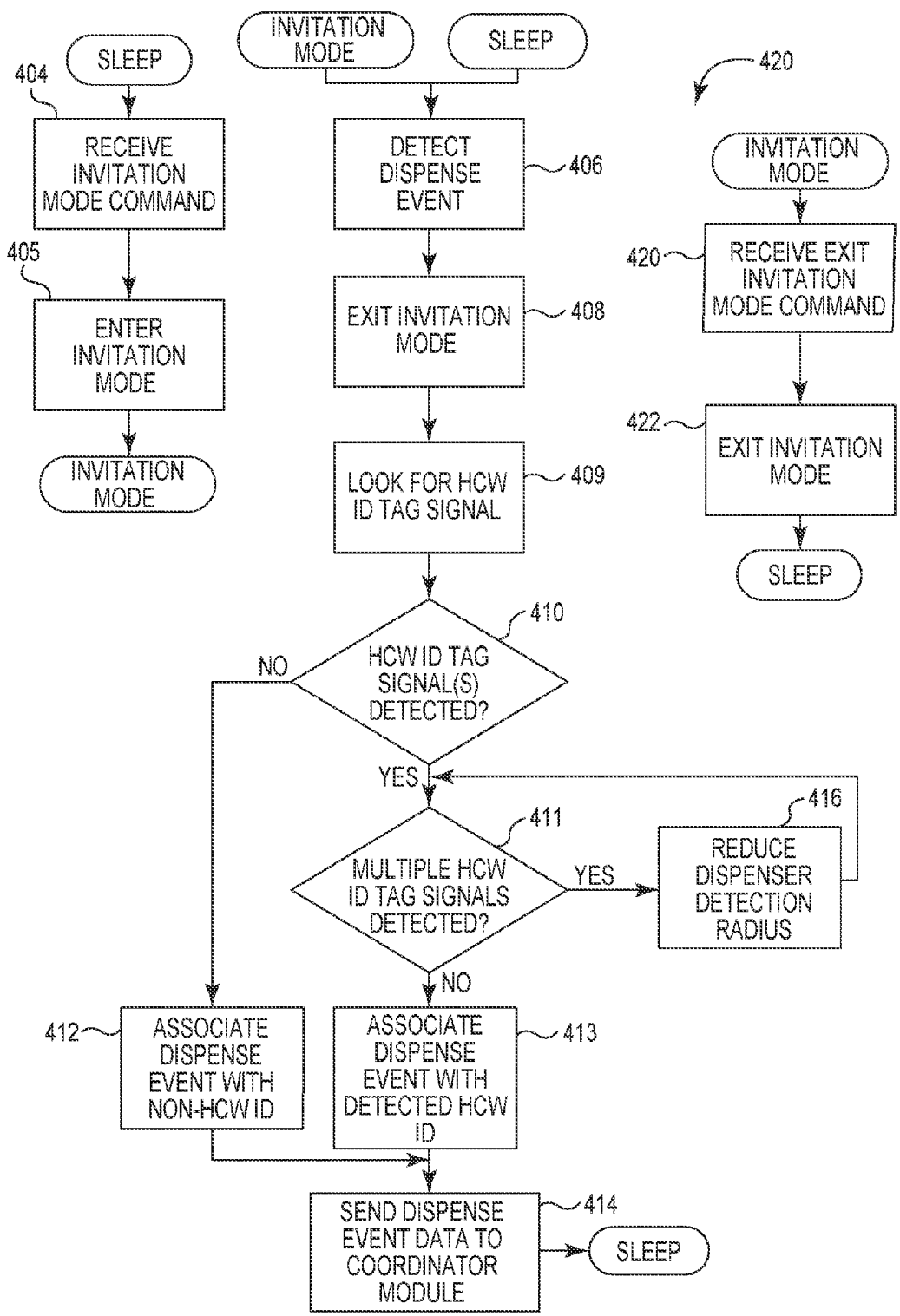
FIG. 16 is a flowchart illustrating an example process of operation for a dispenser module.

FIG. 16 is a flowchart illustrating an example process 420 of operation for dispenser module 16. In the example process shown in FIG. 16, dispenser module 16 spends most of its time in a low power "sleep mode." Operation of dispenser module 16 in this way may serve to reduce power consumption and preserve battery life. It shall be understood, however, that motion detector module 14 need not operate this way, and that the disclosure is not limited in this respect. For example, dispenser module 16 need not include a sleep mode, but may be continuously active if power consumption and/or battery life is less of a concern.

Several events may cause dispenser module 16 to "wake up." For example, if a dispenser 16 receives a command to enter invitation mode (404), dispenser module 16 will enter invitation mode (405), during which audible or visible indicators on the dispenser 16 serve to remind a person entering the room of a hand hygiene opportunity. As another example, if a dispense event occurs (406) while the dispenser module 16 is in sleep mode (406), dispenser module 16 will wake up. If the dispense event is detected (406) while dispenser module 16 is in invitation mode (405), dispenser module will exit invitation mode (408).

Once detector module 16 detects a dispense event, dispenser module 16 looks for any HCW tag signals within range (409) of the dispenser. For example, detector module 16 may have an initial range of 0-1 meter or some other appropriate distance that helps to ensure that only the HCW id tag 4 associated with the HCW who initiated the dispense event is detected and not another nearby HCW id tag.

If no HCW id tag signal is detected within a predefined period of time (410) (such as 0.5 seconds, 1 second, 2 seconds, 5 seconds or other appropriate time interval, for example) dispenser module 16 associates the dispense event with non-HCW identification information.

If a HCW id tag signal is detected within a predefined period of time (410), dispenser will check whether more than one HCW id tag signals have been detected at the same time (411). If only one HCW id tag signal has been detected, dispenser module 16 associates the dispense event with the detected HCW identification information (413). Dispenser module 16 then sends the dispense event data to coordinator module 18 (414).

If multiple HCW id tag signals are detected (411), dispenser module 16 may reduce the detection radius in an attempt to isolate the HCW id tag that is closest to the dispenser (416). For example, dispenser module 16 may modify the output power of the interrogation signal to effectively reduce the detection radius of the dispenser. If multiple HCW id tags are still detected, dispenser module 16 may continue to reduce the detection radius until only one HCW id tag is detected. For example, dispenser module 16 may modify the detection radius from approximately 1.5 meter to approximately 1 meter, and then to 0.5 meters, etc. until a single HCW id tag is isolated. Dispenser module 16 may then associate the dispense event with the isolated HCW id tag (413) and sends the dispense event data to coordinator module 18 (414).

In addition, dispenser module 16 may be in invitation mode when an exit invitation mode command is received (420). This would occur, for example, when an entry event is detected but no corresponding dispense event is detected with a target time window (e.g., a non-compliant event). Dispenser module 16 would then exit invitation mode (422) and re-enter sleep mode.

Figure 17:
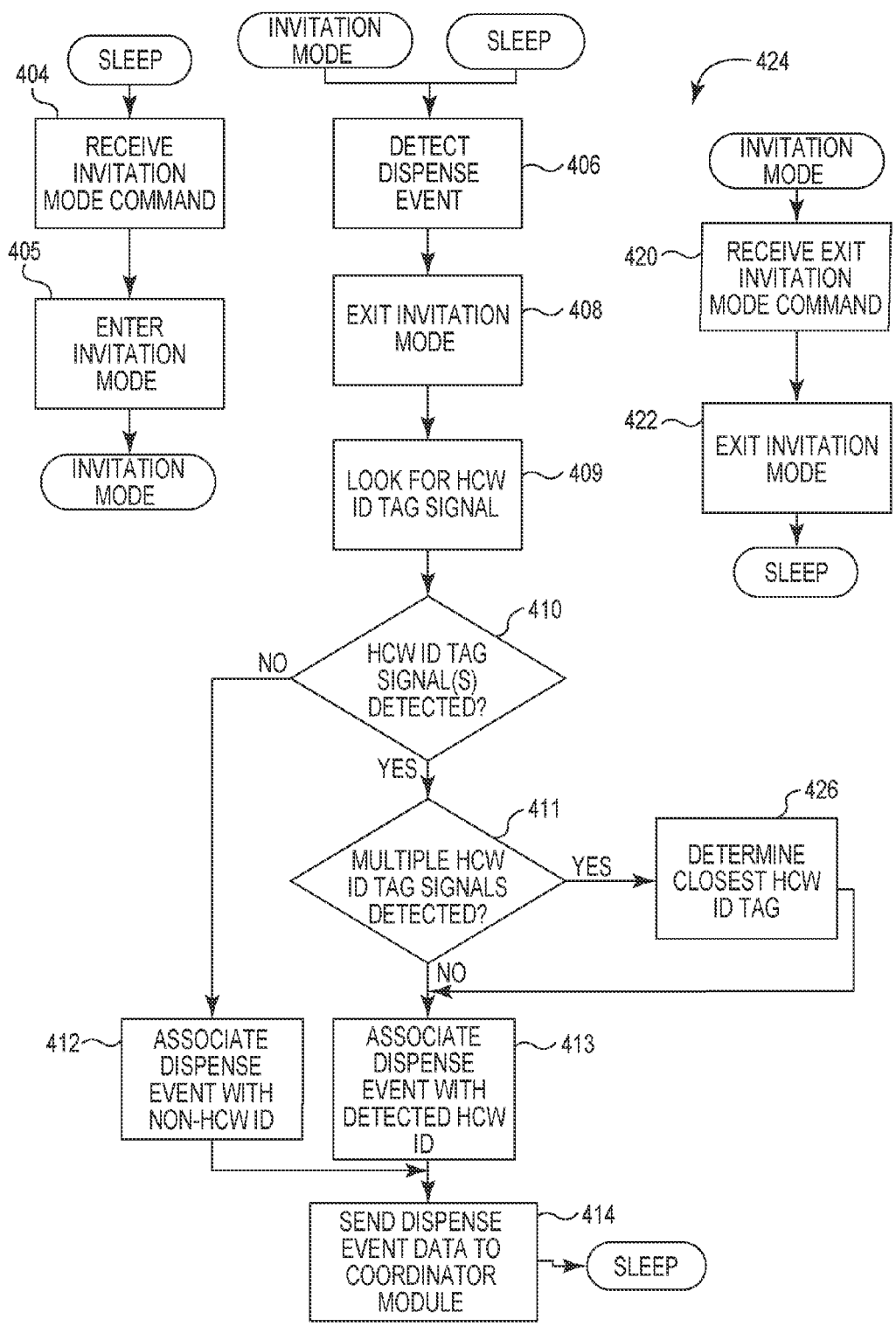
FIG. 17 is a flowchart illustrating another example process of operation for a dispenser module.

FIG. 17 is a flowchart illustrating another example process 424 of operation for dispenser module 16. Process 424 shown in FIG. 17 is identical to the process 420 shown in FIG. 16 except for the manner in which dispenser module 16 attempts to isolate a single HCW id tag from among multiple detected tags. In this example, dispenser module 16 analyzes the signal strength information associated with each of the multiple detected tags to determine which is closest to the dispenser 16 (426). Typically, the HCW id tag with the highest signal strength would be isolated as the HCW id tag that should be associated with the dispense event.

Figure 18:
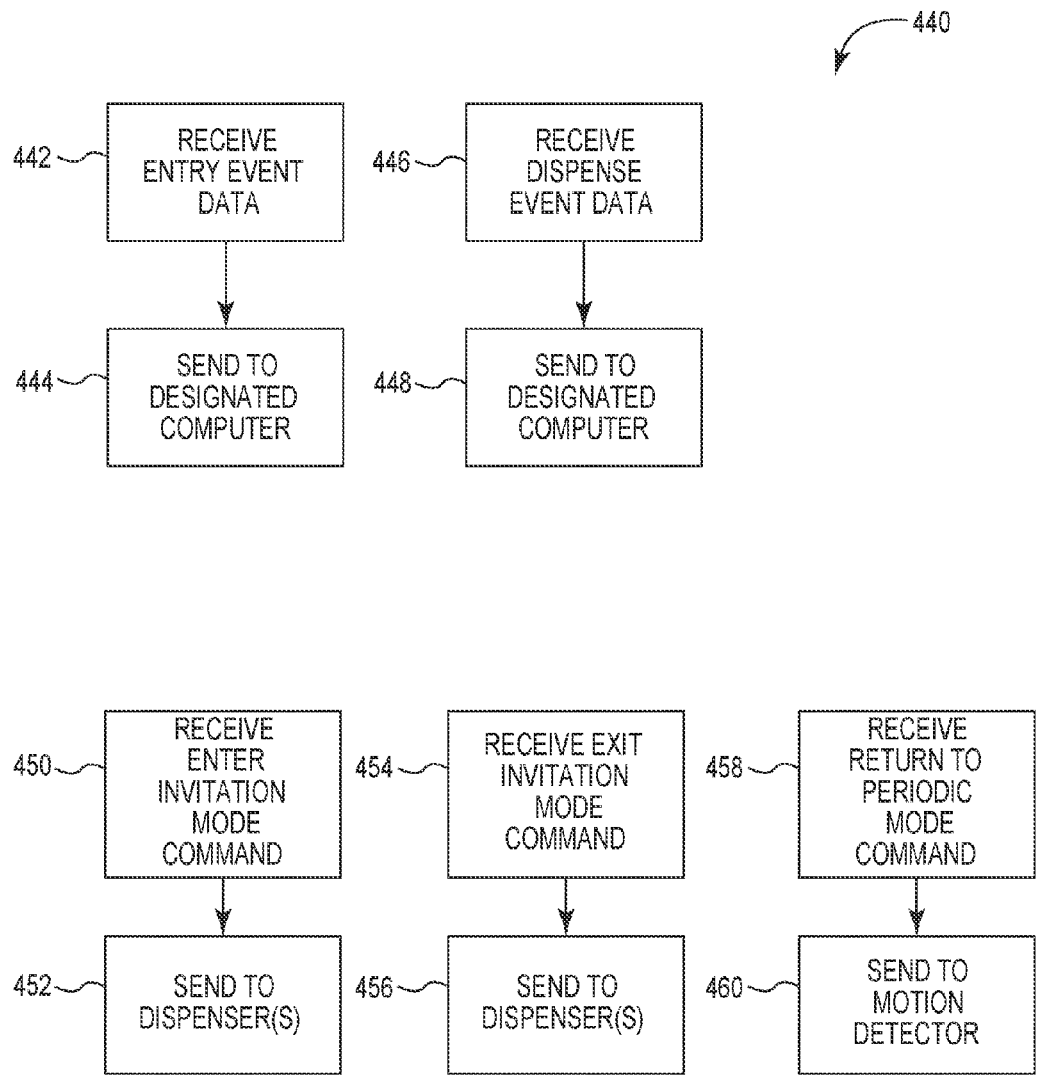
FIG. 18 is a flowchart illustrating example processes of operation of a coordinator module.

FIG. 18 is a flowchart illustrating example processes 440 of operation of coordinator module 18. In this example, a function of coordinator module 18 is to communicate information received from the motion detector 14 and dispenser(s) 16 in the associated room or other defined space to local hospital computer 28 or other designated computer. For example, entry event data from motion detector module 14 (442) and transmits the entry event data to the local hospital computer 28 or other designated computer (444). Coordinator module 18 receives dispense event data from the associated dispenser(s) (446) and transmits the dispense event data to the local hospital computer 28 or other designated computer (448).

Another function of coordinator 18 is to communicate information, such as operational commands, etc., from local hospital computer 28 or other designated computer to the motion detector 14 and dispenser(s) 16 in the associated room or other defined space. For example, enter invitation mode commands (450) and exit invitation mode commands (454) are received by coordinator module 18 and sent to the dispensers 16 in the associated room (452, 456). Similarly, return to periodic mode commands (458) are received by coordinator module 18 and sent to the associated motion detector module 14 (460).

Figure 19:
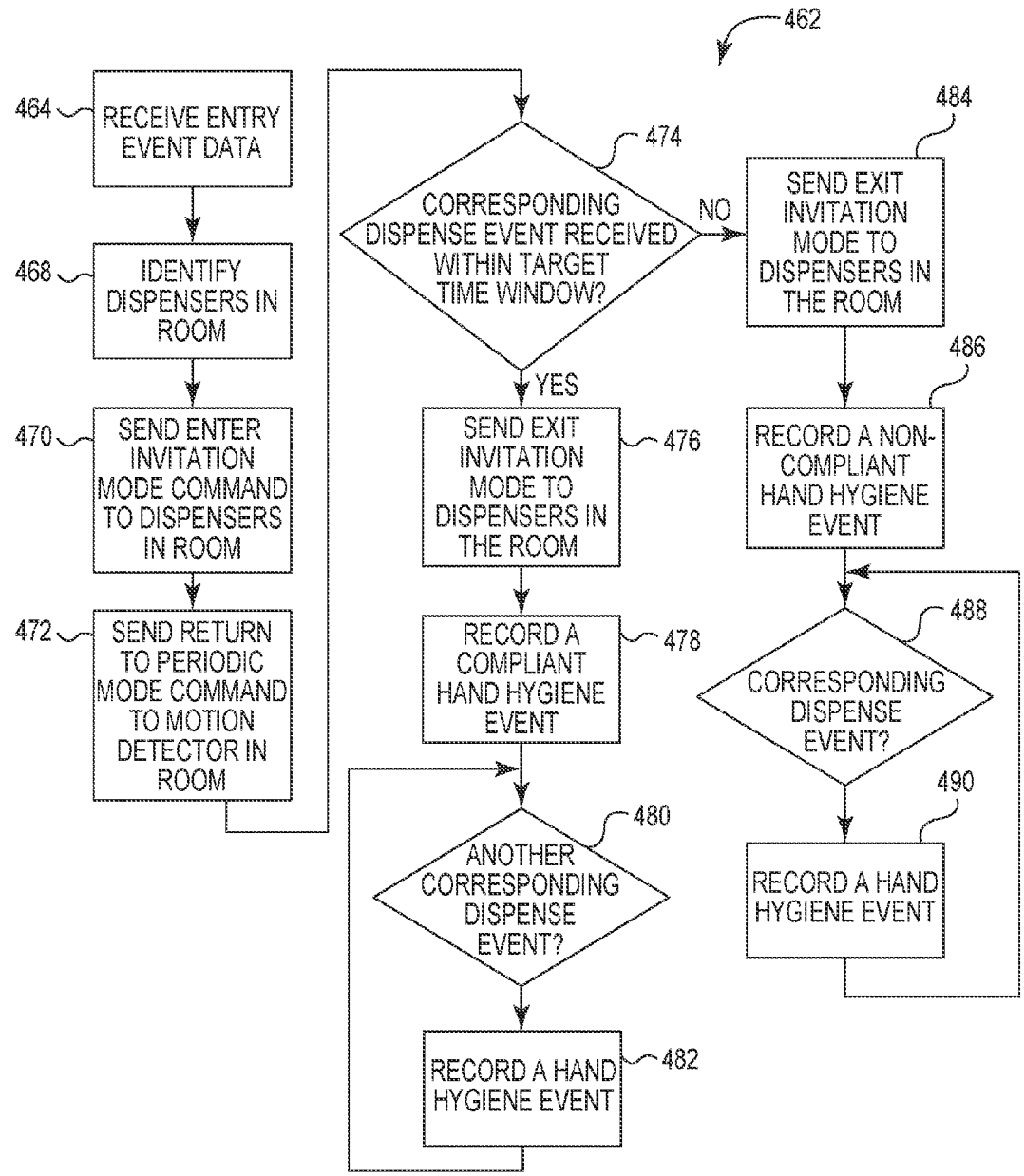
FIG. 19 is a flowchart illustrating an example process by which a local hospital computer or other designated computer determines whether a compliant or non-compliant hand hygiene event has taken place.

FIG. 19 is a flowchart illustrating an example process (462) by which local hospital computer 28 or other designated computer processes the hand hygiene data received from coordinator module 18 to determine whether a compliant or non-compliant hand hygiene event has taken place. Computer 28 receives entry event data from coordinator module 18 (446). Computer 28 identifies which dispensers 16 are in the room associated with the coordinator module 18 (468). Computer 28 sends an enter invitation mode command to the identified dispensers 16 via coordinator 18 (470). Computer 28 may also send a return to periodic mode command to the associated motion detector 14 via coordinator 18 (472).

Computer 28 determines whether a dispense event corresponding to the entry event (that is, a dispense event having the same HCW identification information as the entry event) occurs within a target time window (474). The target time window is determined so that the person associated with the entry event has time to get to one of the dispensers in the room but not so long as to result in an increased likelihood that the person comes into close proximity to the patient without completing a hand hygiene event. For example, the target time window may be between 5 and 30 seconds, or some other appropriate time window.

If a corresponding dispense event is detected (474), computer 28 sends an exit invitation mode command to all of the identified dispensers in the room via coordinator 18 (476). Computer 28 records a compliant hand hygiene event (478) (for example, "HCW id #X entered room #Y at time $t_{enter}$ and washed hands in less than t seconds ($t_{dispense}-t_{enter}$) at dispenser #Z"). If at some later time a HCW who was already present in the room initiates another corresponding dispense event (480), computer 28 will record another hand hygiene event (482) (for example, "($t_{dispense\#2}-t_{enter}$) seconds/minutes after entering room #Y, HCW id #X completed a second (third, fourth, etc.) hand hygiene event at dispenser #Z").

If no corresponding dispense event is detected within the target time window (474) computer 28 may send an exit invitation mode command to the dispensers 16 in the room (484). Computer 28 records a non-compliant hand hygiene event (486) (for example, "HCW id #X entered room #Y at time $t_{enter}$ and failed to complete a compliant hand hygiene event within $t_{target}$ seconds").

If at some later time a HCW who was already present in the room but had failed to complete a compliant hand hygiene event initiates a dispense event (488), computer 28 will record a hand hygiene event (490) (for example, "($t_{dispense\#2}-t_{enter}$) seconds/minutes after entering room #Y, HCW id #X completed a second (third, fourth, etc.) hand hygiene event at dispenser #Z").

For entry events associated with non-HCW identification information (e.g., a person without a HCW id tag), computer 28 may follow a similar process as process 462 shown in FIG. 19. However, for untagged individuals (visitors, patients, etc.) computer 28 may simply record whether or not the untagged individual washed their hands within a defined period of time. For example, a compliant hand hygiene event for an untagged individual (478) may include, for example, "An untagged individual entered room #Y at time $t_{enter}$ and completed a hand hygiene event at dispenser #Z in ($t_{enter}-t_{dispense}$) seconds." A non-compliant hand hygiene event for an untagged individual (486) may include, for example, "An untagged individual entered room #Y and time $t_{enter}$ and did not complete a hand hygiene event within $t_{target}$ seconds."

Figure 20:
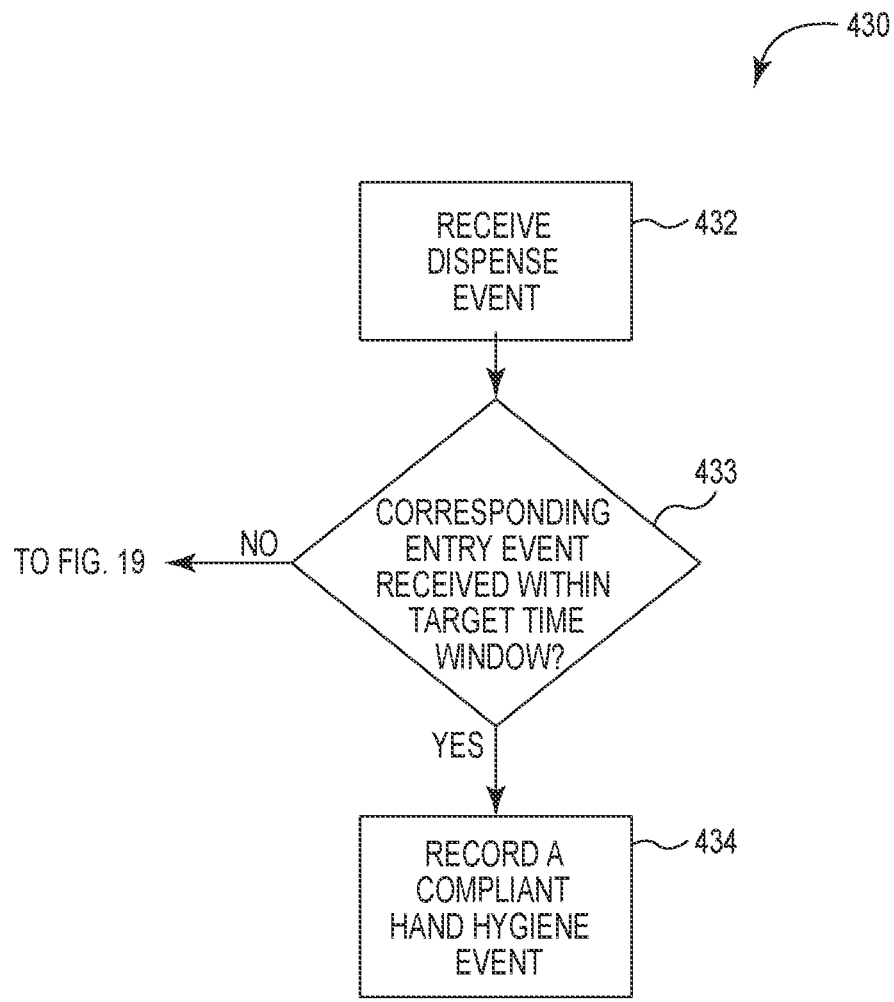
FIG. 20 is a flowchart illustrating a process by which local hospital computer or other designated computer monitors for compliant or non-compliant hand hygiene events for dispensers located outside of a patient room or other defined space.

FIG. 20 is a flowchart illustrating a process 430 by which local hospital computer or other designated computer monitors for compliant or non-compliant hand hygiene events for dispensers located outside of a patient room or other defined space. In some hospitals, or areas or rooms within a hospital, hand hygiene dispensers may be located immediately outside a patient room. In those cases, dispense events occurring at those dispensers corresponding to entry events that occur within a defined target time window may be recorded as compliant hand hygiene events.

For example, local hospital computer or other designated computer receives dispense event data (432). Computer 28 determines whether a corresponding entry event occurs within a target time window (433). If so, computer 28 records a compliant hand hygiene event (434) (for example, HCW id #X completed a hand hygiene event at dispenser #Z at time $t_{dispense}$ and entered room #Y within time $t_{target}$"). If no corresponding entry event is received (433) (e.g., time $t_{target}$ has passed without the person entering the room), computer 28 follows the procedure described above with respect to FIG. 19. For example, computer 28 receives the entry event data (464), identify the dispensers in the room (468), send an enter invitation mode command to the dispensers in the room (470) (thus inviting the HCW to complete a compliant hand hygiene event) and monitor for a compliant or non-compliant hand hygiene event (472-490) as described above.

As described herein, various aspects of the hand hygiene compliance system may be computer implemented, and as such may be incorporated into computer software or hardware. For example, a computer system may collect and analyze data generated during implementation of the hand hygiene compliance system. This information may be stored and analyzed and reports generated to provide feedback to a facility manager or corporation. Furthermore, the analysis may be performed across multiple accounts, such as multiple accounts within a single corporation or organizational region, to compare, for example, one hospital in a corporation with other hospitals within the same corporation or to compare like modules of multiple hospitals.

The techniques described herein may be implemented in hardware, software, firmware or any combination thereof. If implemented in software, the techniques may be realized at least in part by a computer-readable medium comprising instructions that, when executed by computer of a hand hygiene compliance system cause the computer to perform one or more of the techniques of this disclosure. The computer-readable data storage medium may form part of a computer program product, which may include packaging materials. The computer-readable medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, a magnetic disk or a magnetic tape, a optical disk or magneto-optic disk, CD, CD-ROM, DVD, a holographic medium, or the like. The instructions may be implemented as one or more software modules, which may be executed by themselves or in combination with other software.

The computer-readable instructions may be executed in the computer of the system by one or more processors, general purpose microprocessors, ASICs, FPGAs or other equivalent integrated or discrete logic circuitry.

The instructions and the media are not necessarily associated with any particular computer or other apparatus, but may be carried out by various general-purpose or specialized machines. The instructions may be distributed among two or more media and may be executed by two or more machines. The machines may be coupled to one another directly, or may be coupled through a network, such as a local access network (LAN), or a global network such as the Internet. Accordingly, the term "processor," as used herein may refer to any structure suitable for implementation of the techniques described herein.

Various aspects of the hand hygiene compliance system may also be embodied as one or more devices that include logic circuitry to carry out the functions or methods as described herein. The logic circuitry may include a processor that may be programmable for a general purpose or may be dedicated, such as microcontroller, a microprocessor, a Digital Signal Processor (DSP), an Application Specific Integrated Circuit (ASIC), a field programmable gate array (FPGA), and the like.

One or more of the techniques described herein may be partially or wholly executed in software. For example, a computer-readable medium may store or otherwise comprise computer-readable instructions, i.e., program code that can be executed by a processor to carry out one of more of the techniques described above.

The hand hygiene compliance system may also incorporate healthcare worker training and continuing education, such as teaching new or ongoing skills and changing paradigms and behaviors within hospitals. These may include, for example, hand hygiene training, compliance/procedural training, training oversight/monitoring/interventions, comprehensive training to impact outcomes, medical school and association curriculum, certification training, etc. This may include both upfront and periodic refresher training, training materials and a training process to help ensure that HCWs are following hand hygiene best practices.

Figure 21A:
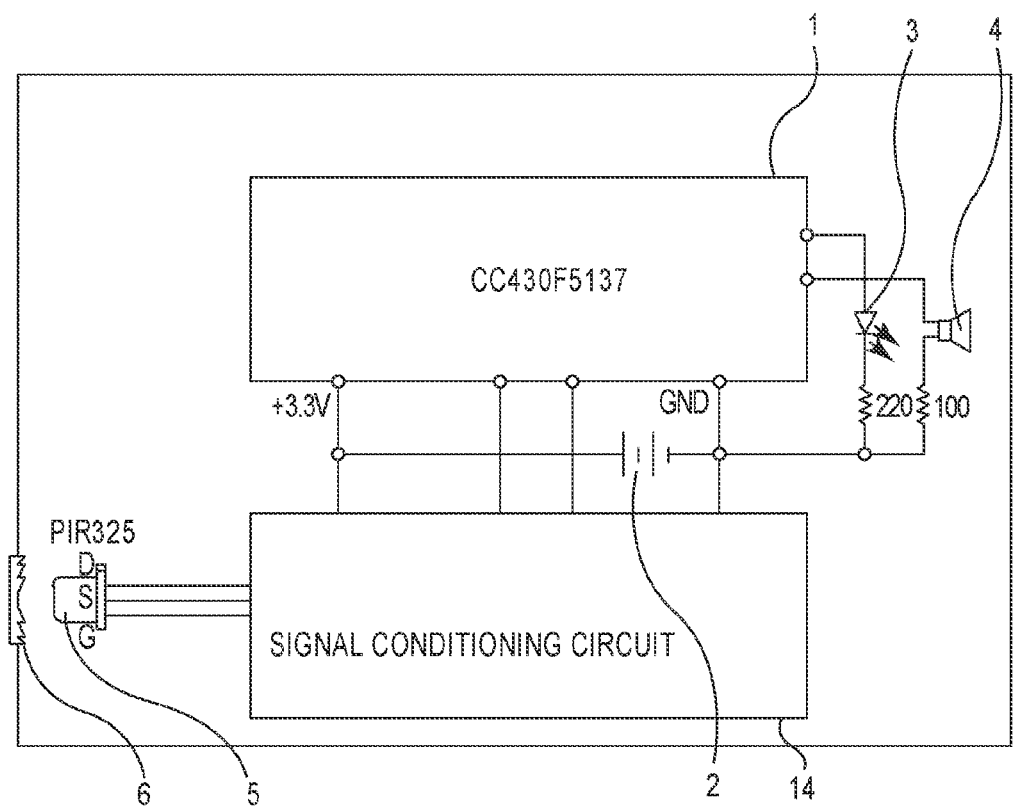
FIGS. 21A-21F are electrical schematic diagrams illustrating example implementations for the components of an alternative hand hygiene compliance system.
Figure 21B:
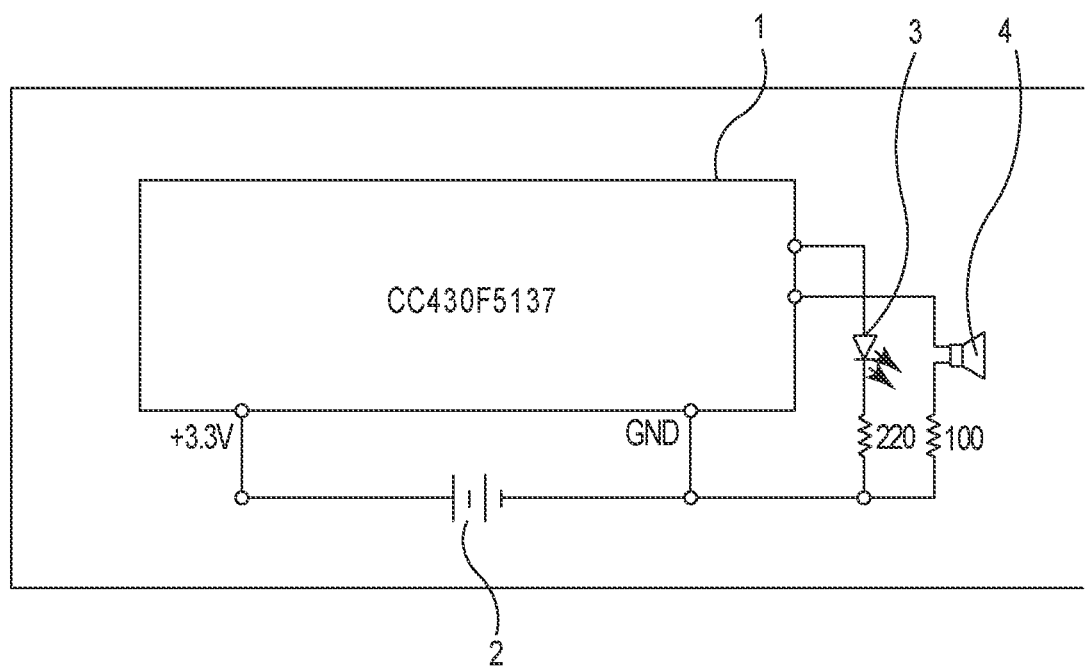
Figure 21E:
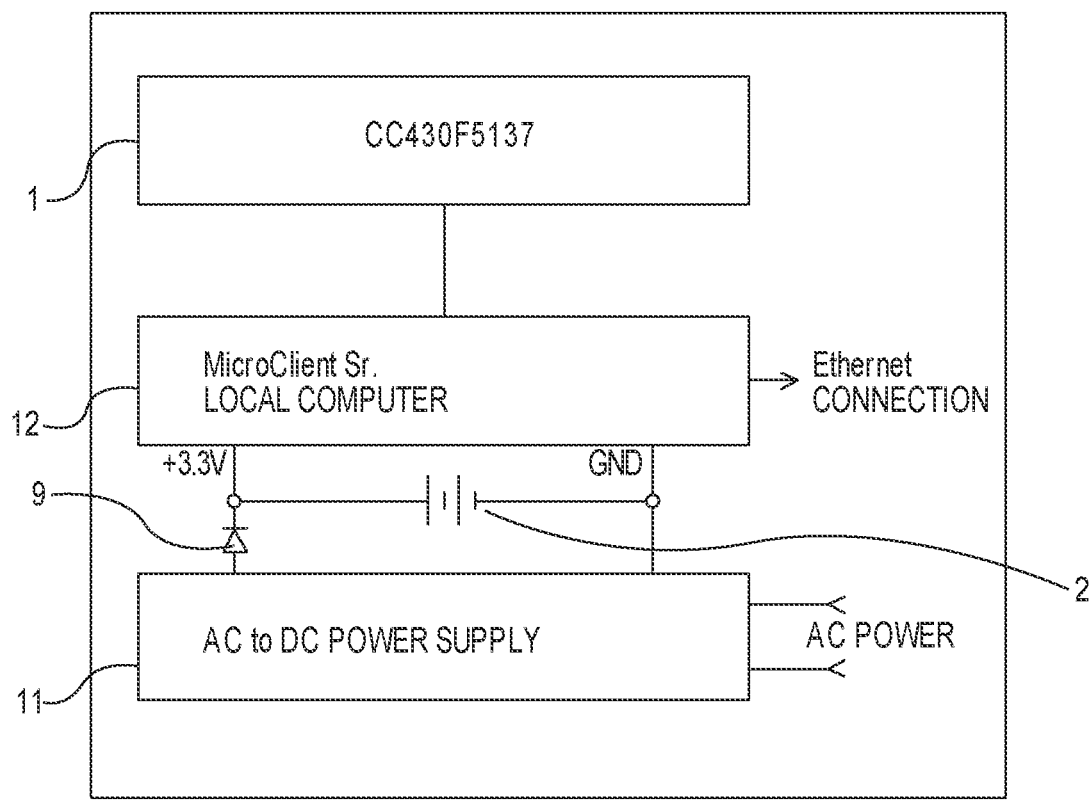
Figure 21F:
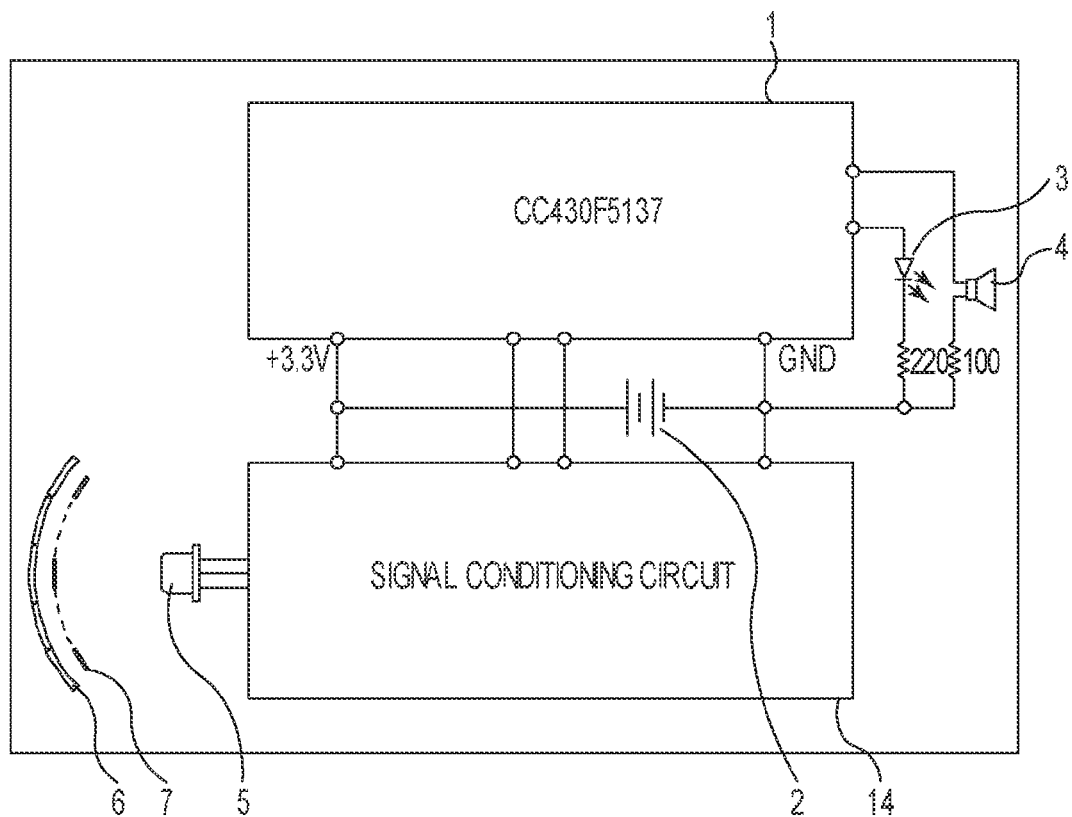
Figure 22A:
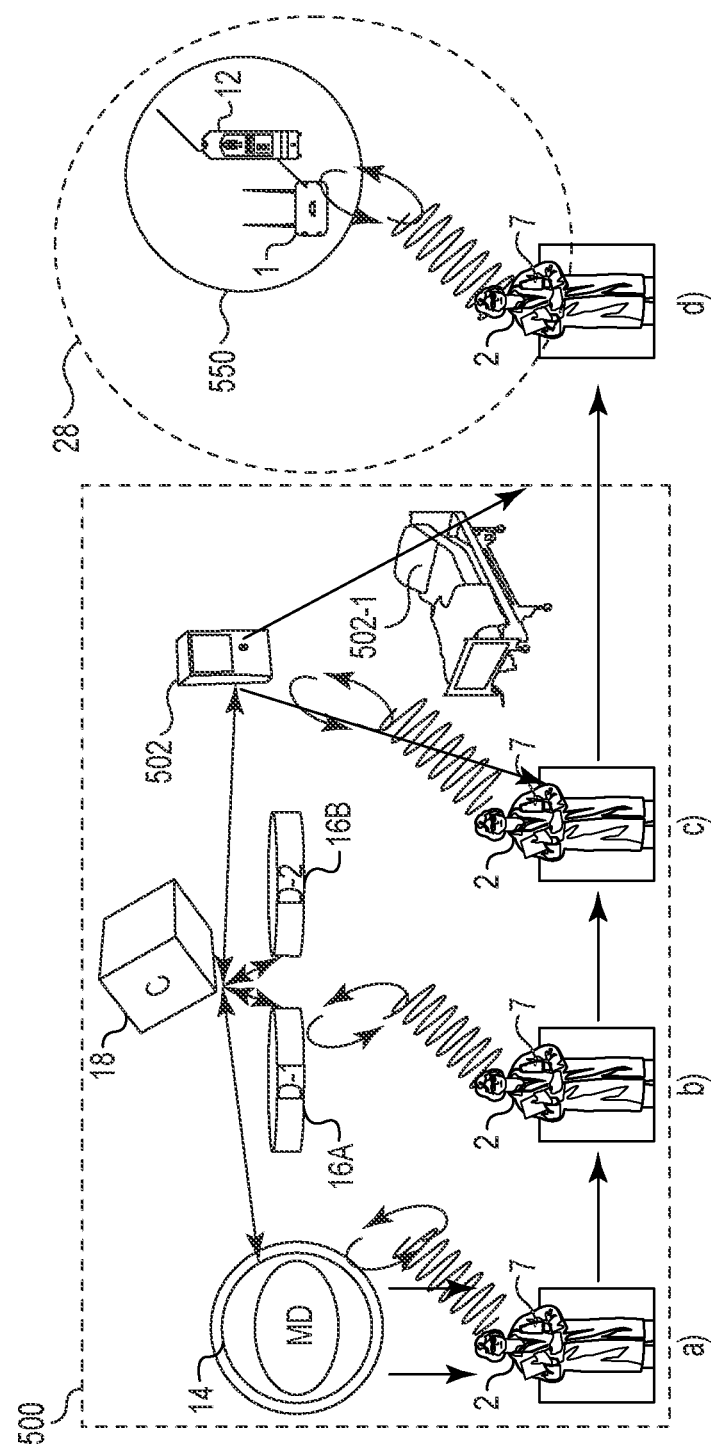
FIG. 22A is a block diagram illustrating an example of the alternative hand hygiene compliance system with multiple independent subnets

Another example implementation of a hand hygiene compliance system, shown in FIG. 22 A, comprises multiple subnet zones 500 each of which provides independent hand hygiene compliance monitoring in limited areas. The system of FIG. 22A may provide a power efficient system with an extended coverage without integrating into a hospital's wireless system. Health Care Workers (HCW) 2 have ID tags 7 which normally operate within a relatively short communication range (a low power setting resulting in a maximum range of about 3-10 meters, for example). The HCW id tag 7 stores all entry event data and dispense event data related to that HCW id tag. Throughout the day, as the HCW tags 7 move about the hospital, they will at times enter a data gathering area 28 within the hospital that serves as a tag data download site. An electrical schematic diagram of an example data gathering station 550 is shown in FIG. 21E. It includes a local computer 12 having a wireless or wired connection to the hospital network and a wireless communication unit 1 able to communicate wirelessly with HCW id tags 7. Any HCW id tag signal in the data gathering area will be detected. The data gathering station 550 may then switch the id tag into a relatively longer communication range and obtain the HCW identification information, entry event data and dispense event data associated with each HCW id tag present in the data gathering area 28.

For example, a subnet 500 can be assigned to each patient room (shown in FIG. 22A) and may include, for example, IR motion detector 14 (shown in FIG. 21A) at the entry, dispensers 16A and 16B (shown in FIG. 21C), wireless coordinator 18 (shown in FIG. 21D), and an IR proximity wireless check point 502 (shown in FIG. 21 F). In this example, IR proximity wireless check point 502 and data gathering station are implemented using System on a chip CC430F5137 (Available from Texas instrument Inc., Dallas, Tex.).

Figure 23A:
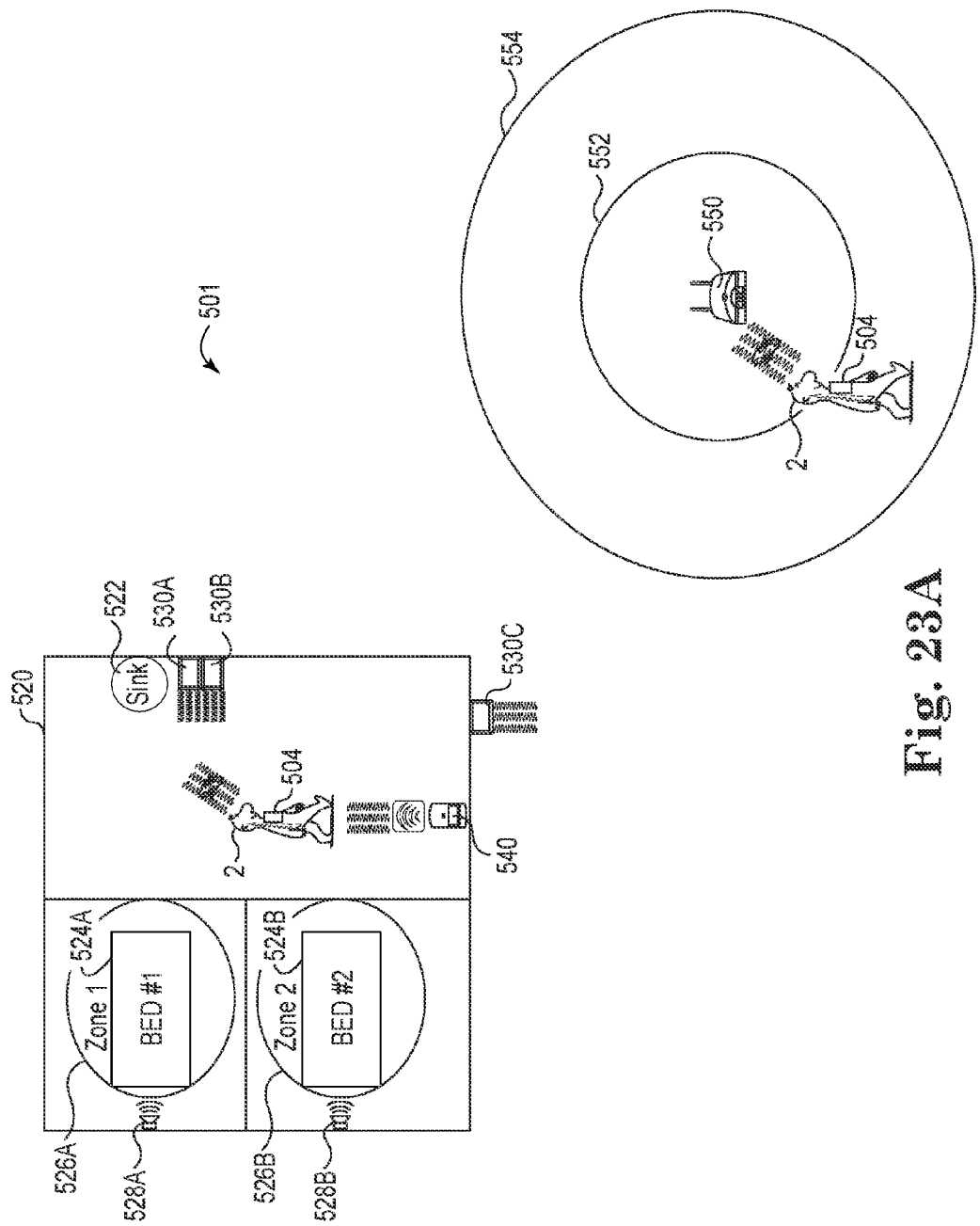
FIGS. 23A and 23B are a diagram illustrating an example hand hygiene compliance system 501 in which a plurality of hand hygiene compliance badges, each uniquely associated with a different one of a plurality of HCWs, monitor hand hygiene compliance in a healthcare or other facility.

Wireless communication of motion detector 14, dispensers 16A and 16B, coordinator 18 and checkpoint 502 with a tag (FIG. 21B) has a low power setting limited to one subnet 500, or patient room in this example. IR proximity wireless check point 502 (FIG. 21 F) has similar schematics as IR motion detector (FIG. 21A). It includes a Fresnel lens array 6 and an opaque shield 7 with transparent zones forming detection areas for a Pyroelectric detector 5. IR proximity wireless check point 502 is placed near areas where monitoring of hand hygiene compliance is desired, such as patient-centered protection zones. Each check point 502 may therefore be associated with an operational area limited to one patient bed 502-1 or other patient-centered zone. Opaque shield 7 blocks a central part of the detection zone. For example, the opaque shield 7 blocks detection in the area of the detection zone in which the patient bed is present, thus the patient bed is essentially invisible for the Pyroelectric detector 5 but any movements in the perimeter around the bed 502-1 can be detected. This ensures that movements of the patient do not trigger motion detection. Coordinator module (FIG. 21D) turns IR proximity wireless check point 502 in continuous mode of operation for limited time (e.g., 5-30 seconds) when an entry event occurs. When IR proximity wireless check point 502 detects the tag in proximity it can communicate with tag. The tag analyzes the time delay between last hand washing event and can remind HCW 2 that hand washing is required. In this example, tag 7 keeps stores information about all hand hygiene compliance events or non-compliance events in which this tag is involved. For example, id tag 7 records hand hygiene information (dispenser data, entry data, entry/exit into or out of check point zone) when a HCW 2 is near points a), b), c) as shown in FIG. 23A and download information when HCW 2 is in the data gathering area 28 as shown in FIG. 23A point d). Tag 7 may also receive from coordinator 18 information about hand compliance monitoring events which where recorded but have no connection with a person carrying a tag. Multiple tags 7 store all hand hygiene information which can be downloaded automatically when tags are in proximity of a local subnet reader (checkpoint) 550 (FIG. 21E).

Figure 22B:
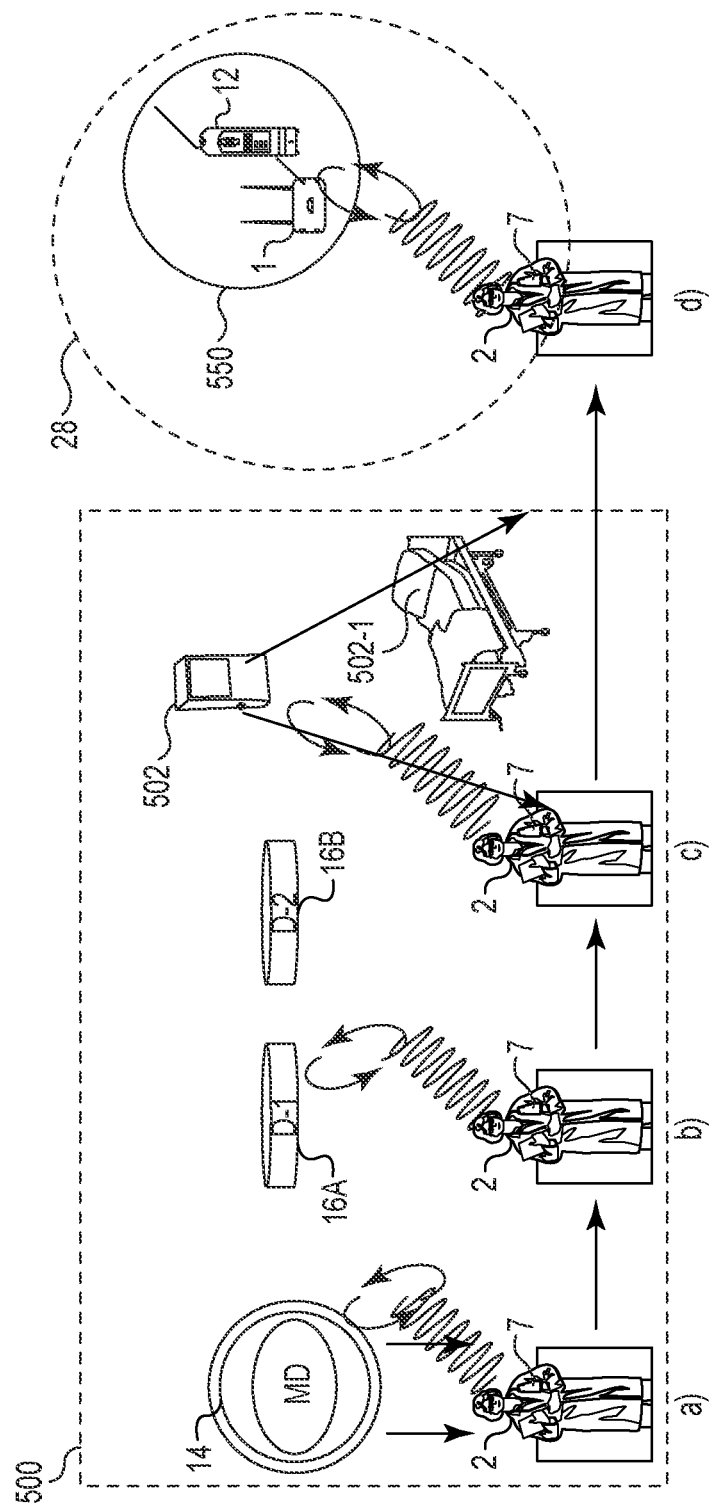
FIG. 22B is a block diagram illustrating an example of another+alternative hand hygiene compliance system.

Another example hand hygiene compliance system is shown in FIG. 22B. The system FIG. 22B is similar to that of FIG. 22 but does not include a coordinator module. The system of FIG. 22B accumulates data about hand hygiene compliance only for people who have tags. In this example, each subnet zone 500 includes a motion detector 14, dispensers 16A and 16B or an IR proximity wireless check point 502. When motion or a dispense event is detected, wireless communication with the tag is turned ON for a relatively short period of time (e.g., 2-3 seconds). HCW id tags can receive hand hygiene information, analyze it and store in memory. In this example the IR proximity wireless check point 502 can synchronously reestablish communication with the id tag 7 each 1-5 seconds to confirm that specific id tag 7 still is in the protection zone.

Advantages of the hand hygiene compliance system may include documented improvements in hand hygiene compliance, patient satisfaction scores, and HAI risk reduction and associated cost savings. Advantages may also include fewer patient deaths and patient complications due to HAIs.

Although the hand hygiene compliance system has been described with respect to hospitals or other healthcare facilities, it shall be understood that this concept may also be applied to hand hygiene compliance in many different enterprises in which an integrated approach to hand hygiene in a portion of a facility or an entire facility is desired. For example, the modular hand hygiene compliance system may be adapted for use in applications such as hotel room cleaning, education facilities, long term care, restaurants, food service, food and beverage facilities, food packing, eating areas, rest rooms, food preparation areas, cooking areas, etc.

In another example hand hygiene compliance system, monitoring of hand hygiene compliance is initiated when a HCW comes into relatively close proximity to a patient. In this example, monitoring of hand hygiene compliance is organized around patient-centered critical control points (CCP), such as patient beds, examination tables, or other patient locations where monitoring of hand hygiene compliance is desired. Protection zones are set up around each CCP, thus defining a protected area around each patient. Each HCW is assigned a compliance badge that is uniquely associated with the HCW. A set of compliance rules, stored by a motion detector associated with each AOC, are communicated to each compliance badge that enters the AOC. To monitor hand hygiene compliance, each compliance badge monitors entry and exit from areas of concern (AOC), entry and exit from patient protection zones, and hand hygiene product dispense events. Using the compliance rules, each compliance badge monitors occurrence of compliant or non-compliant hand hygiene events. Each compliance badge thus monitors and stores compliance data unique to each HCW. A plurality of data gathering stations set up in various locations around the healthcare facility, such as nurse's stations, cafeterias, etc., initiate automatic download of compliance data whenever a badge is within range. The compliance data from all compliance badges in the system may be transmitted to a local hospital computer and/or remote computer 560 for data analysis and reporting.

In another example, each compliance badge need not store healthcare worker identification information. For example, each badge may include a unique badge identifier, so that all dispense events associated with each badge may be monitored and analyzed. In this example, the local or remote computer (such as local computer 555, server computer 560 or user computer 554) may include the ability to associate each badge with an individual HCW. However, it shall be understood that there may be circumstances in which it may be undesirable or unnecessary to specifically identify individuals and their associated hand hygiene activities, and that more generalized monitoring of hand hygiene compliance via unique badge identifiers may in some circumstances be sufficient.

Figure 23B:
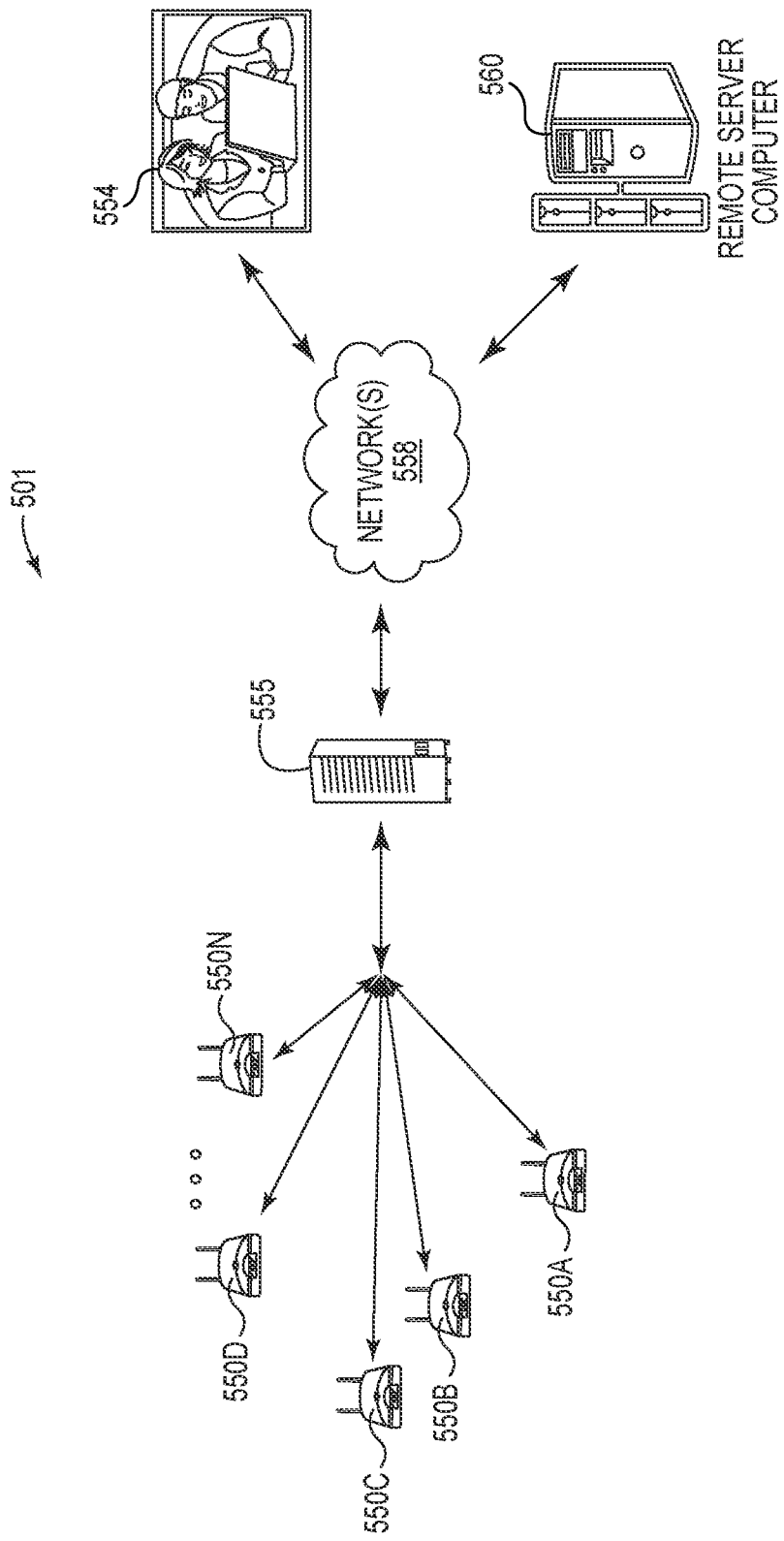

FIGS. 23A and 23B are a diagram illustrating an example hand hygiene compliance system 501 in which a plurality of hand hygiene compliance badges, each uniquely associated with a different one of a plurality of HCWs, monitor hand hygiene compliance in a healthcare or other facility. In this example, a plurality of areas of concern (AOC) in which monitoring of hand hygiene compliance is desired are set up in various areas throughout a healthcare facility. In FIG. 23, the AOC 520 is a patient room. The example AOC 520 includes two patient beds, 524A and 524B, and a sink 522. Although a patient room is illustrated in this example, AOC 520 could also be a critical care unit, recovery room, operating room, examination room, or any other defined area within a healthcare facility in which monitoring of hand hygiene compliance may be desired. AOC 520 may also include any number of sinks, beds, or other AOC features depending upon the particular needs of each AOC or the particular set up of each AOC.

Within each AOC is at least one patient-centered critical control point (CCP). In FIG. 23, patient beds 524A and 524B are defined as CCPs. Associated with AOC 520 are elements of the example hand hygiene compliance system, including one or more hand hygiene product dispensers 530, in this case two in-room dispensers, 530A and 530B and one outside-room hand hygiene product dispenser 530C; a motion detector 540, and critical control point (CCP) zone emitters 528A and 528B (referred to generally as zone emitters 528), each associated with a CCP 524A and 524B, respectively. The system 501 also includes a plurality of compliance badges 504 (one of which is shown in FIG. 23), each associated with a different one of a plurality of healthcare workers (HCW) 2 (one of which is shown in FIG. 23).

In operation, each CCP emitter 528A and 528B generates a protection zone, 526A and 526B, respectively in this example, around the associated CCP, in this case, the two patient beds 526A and 526B present in AOC 520. However, it shall be understood that critical control points and associated protection zones may be defined with respect to any area within a healthcare facility where a patient could be located and monitoring of hand hygiene compliance may be desired, such as patient beds, chemotherapy stations, treatment areas, surgical tables, examination tables, etc. In this example, zone emitters 528 generate an ultrasonic protection zone around each patient bed.

Each compliance badge 504 includes a microprocessor, an ultrasonic receiver that detects entry into a CCP protection zone 526A or 526B (a "protection zone entry event"), a rule implementation module (instructions for detecting occurrence of compliant or non-compliant hand hygiene events), a power conservation module, a chirp alarm, and a badge data module that stores compliant/non-compliant events and other associated data. To reduce energy consumption and increase battery life, each compliance badge 504 remains in a "power conservation mode" unless present within an AOC or within range of a data gathering station 550 (shown in FIG. 23B).

Motion detector 540 detects movement within AOC 520. For example, motion detector 540 detects movement within proximity to the entrance of an AOC (to detect entrance of persons into the AOC 520). This is termed an "entry event." Motion detector 540 may also detect movement within the AOC 520 (to detect presence of persons moving within the AOC 520). If movement is detected, motion detector 540 broadcasts a wireless "wake-up" signal within the AOC. Each compliance badge 504 within the AOC receives the "wake-up" signal and activates the ultrasonic receiver on the badge. At this point the badge 504 is in "active mode."

Motion detector 540 also stores a set of hand hygiene compliance rules for monitoring compliant/non-compliant hand hygiene events with the associated AOC. Each type of AOC (e.g., patient room, examining room, operating room, therapy station, etc.) may be associated with a different set of compliance rules. Thus, each motion detector 540 in the system as a whole stores compliance rules specific to the AOC with which it is associated.

When a compliance badge 504 is detected entering the AOC, motion detector 540 broadcasts the compliance rules for receipt by all compliance badges within the AOC. Using the compliance rules, compliance badge 504 then monitors the associated HCWs hand hygiene compliance by monitoring entry and exit from protection zones 526A and 526B and any hand hygiene product dispense events that occur while badge 504 is in the AOC. Each compliance badge 504 thus monitors and stores hand hygiene compliance data unique to each HCW.

To detect dispense events, each of dispensers 530 includes an activation or event sensor that detects when hand hygiene product is dispensed (a "dispense event"). In this respect, dispensers 530 may operate in a similar manner to the dispenser described above with respect to the dispenser of FIG. 8 or 21C, for example. Each dispenser 530 includes a wireless dispenser reader that detects HCW id data from any compliance badge 504 within range of the dispenser reader and associates the HCW id data with the detected dispense event.

The wake-up signal broadcast by motion detector 540 may also may cause dispensers 530 to enter an "invitation mode", in which the dispenser activates one or more visual or audible indicators whose purpose is to remind the person entering the room of a hand hygiene opportunity. In some examples, different dispensers throughout the AOC may display invitations at different times as the HCW 2 is detected moving about the AOC from one CCP zone to another CCP zone.

When a HCW leaves the AOC 520 and comes within range of a data gathering station 550, data gathering station 550 initiates automatic download of the compliance data stored on compliance badge 504. As shown in FIG. 23B, a plurality of compliance data gathering stations 550A-55N are set up at various locations around the healthcare facility, such as nurses stations, cafeterias, etc. The compliance data collected from each badge in the system may be transmitted to a local hospital computer 555 and/or remote server computer 560. Local hospital computer 555 and/or remote server computer 560 may then analyze the data and generate one or more hand hygiene compliance reports. These reports may be viewed/printed locally at the healthcare facility and/or at the remote computer 560. In addition, users 554 may view/print the reports remotely via a network such as the internet 558.

Figure 24:
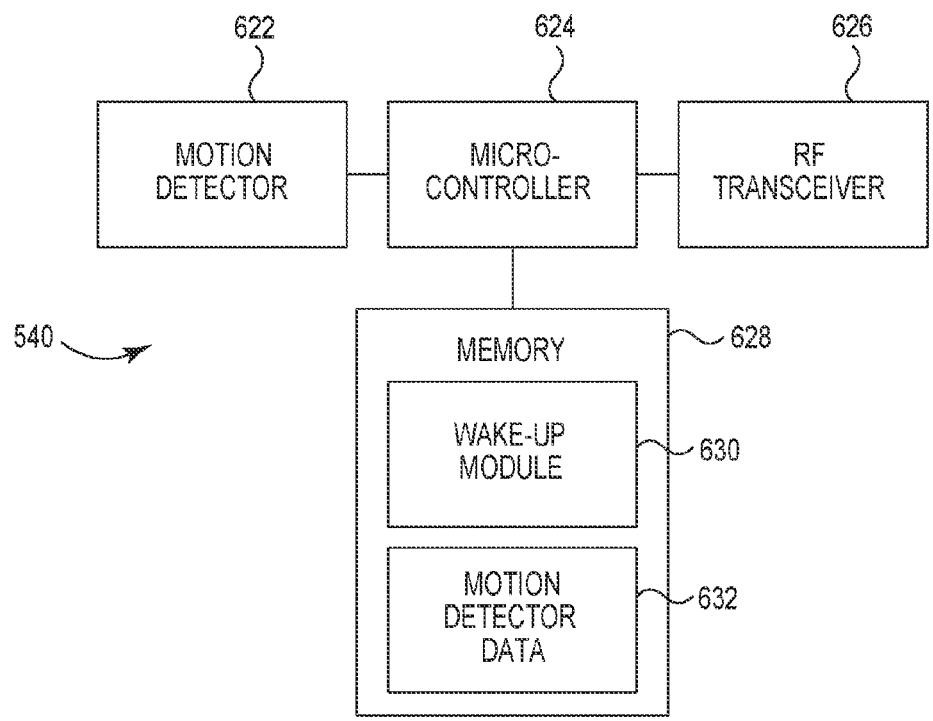
FIG. 24 is a block diagram of an example motion detector.

FIG. 24 is a block diagram of an example motion detector 540. Motion detector 540 includes an IR-based motion detector 622 and an RF transmitter 626. If motion detector 622 detects an AOC entry event or movement within the AOC, the IR motion detector 622 signals the internal RF transmitter 626 to send out the wake-up broadcast to all badges within the AOC. The RF module 626 also transmits the compliance rules that define compliant/non-compliant events for the associated AOC. A memory 628 includes a wake-up module that controls transmission of the wake-up signal. Memory 628 also stores motion detector data 632. Motion detector data 628 may include, for example, data concerning each wake-up signal (time and date stamped). Motion detector data 628 may also include, for example, battery status; motion detector id; motion detector type; physical location (e.g., hospital room number, or other defined area within the hospital, such as a standalone hand washing station, procedure room, lab, common area, operating room, therapy station, etc.); date of installation; maintenance records; detected person events, whether wearing a compliance badge (HCW) or not (non-HCW); detected healthcare worker ids; date and time stamps; and other data associated with the motion detector 540.

Figure 25:
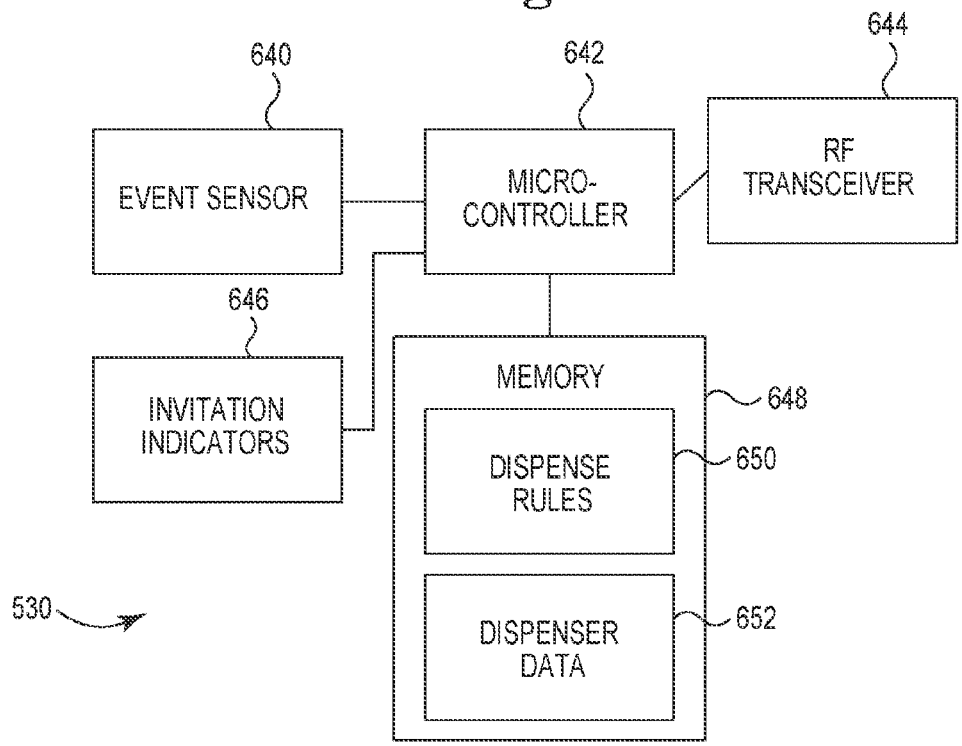
FIG. 25 is a block diagram of an example dispenser.

FIG. 25 is a block diagram of an example dispenser 530. Dispenser 530 includes an event/activation sensor 640, a microcontroller 642, an RF module 644 and indicators 646. Event/activation sensor 640 detects dispense events, and may be implemented as described above with respect to FIG. 8. Indicators 646 may include audible or visual indicators activated during invitation mode, and/or may also include status indicators such as battery status, remaining product status (e.g., whether the dispenser needs to be refilled with hand hygiene product), or other relevant indication of dispenser status.

Microcontroller 648 controls detection of dispense events and communication between dispenser module 16 and compliance badges 504. For example, microcontroller receives an event signal from sensor 640, generates a record of a dispense event and corresponding time stamp, receives HCW or non-HCW identification information from a detected compliance badge, generates corresponding dispenser data concerning the dispense event and transmits the dispenser data to the compliance badge 504.

Figure 26:
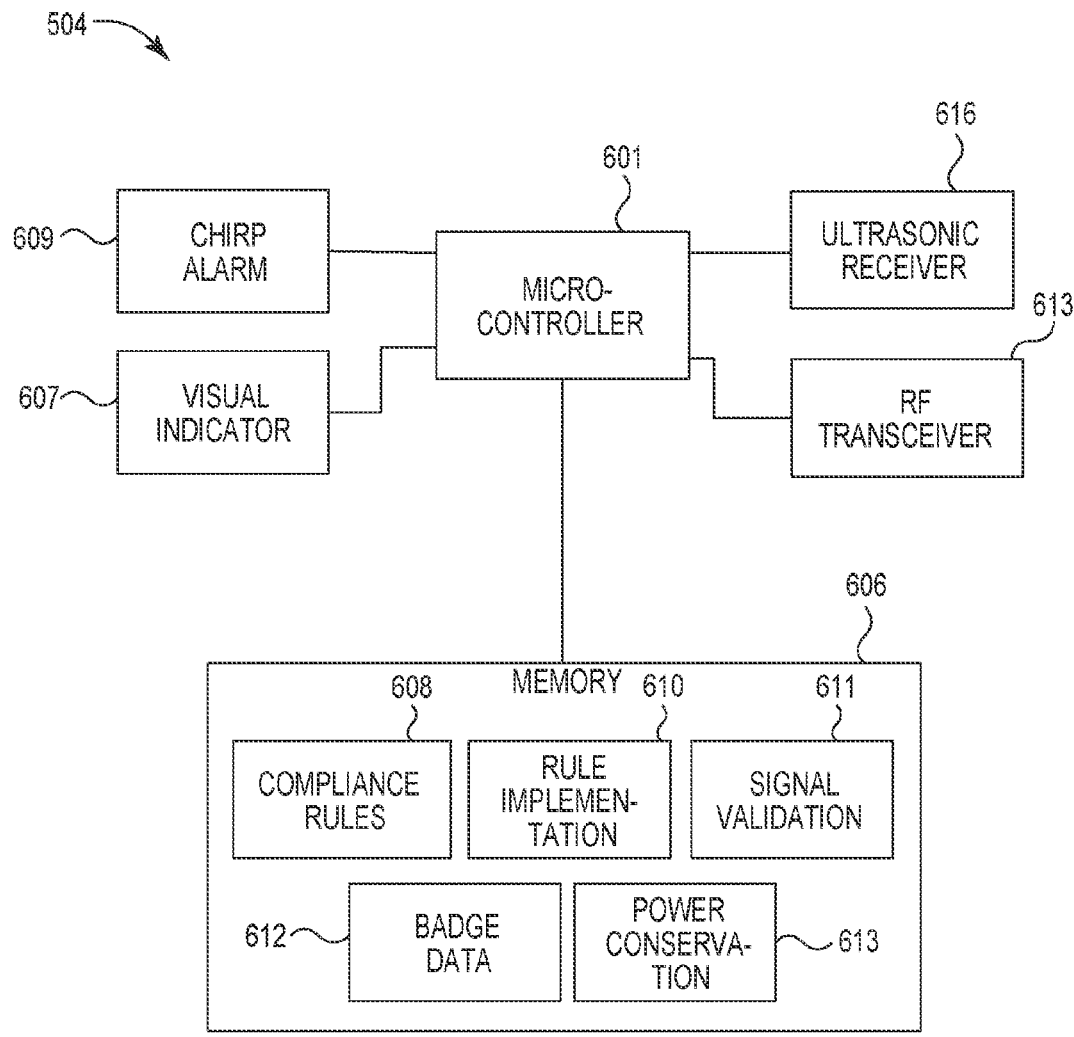
FIG. 26 is a block diagram of an example compliance badge.

FIG. 26 is a block diagram of an example compliance badge 504. Compliance badge includes an ultrasonic receiver 616 that detects the ultrasonic signal generated in a patient protection zone, an RF transceiver 613 that communicates with dispensers 530, motion detector 540 and data gathering stations 550, an audible (e.g., chirp) alarm 609, visual indicators 607. Badge 504 also includes a microcontroller 601 that controls communication with the dispensers 530, motion detector 540 and data gathering stations 550, detects entry into the ultrasonic protection zone, and analyzes the compliance rules to monitor hand hygiene compliance. A memory 606 stores the necessary software and data for the compliance badge 504, including, for example, the compliance rules 608 received from the motion detector upon entry into an AOC; a rule implementation module for implementing the compliance rules to detect compliant/non-compliant hand hygiene events; a sleep/wake-up module that controls automatic power down of the ultrasonic receiver to enter power conservation mode and that also controls activation of ultrasonic receiver when a wake-up signal is received; badge data 612 associated with the compliance badge 612; motion detector data 614 received from motion detector 540; dispenser data 615 received from the dispensers 530A-530C; and an ultrasonic signal validation module 611.

Badge data 612 may include, for example, HCW id, healthcare facility id, AOC entry events, protection zone entry events, dispense events, compliant and non-compliant hand hygiene events, date and time stamps for each event, and any other data relevant to hand hygiene compliance.

As an alternative to motion detector 540 sending out a wake-up signal within AOC 520 whenever motion is detected, badge 504 may include a motion sensor, such as an accelerometer, that detects movement of the associated HCW 2. In this example, if badge 504 senses movement of HCW 2, the ultrasonic receiver would remain activated. In this example, therefore, the ultrasonic receiver would power-down when the badge is not being used, such as, for example, when HCW 2 removes their badge, sets it down or does not use it for a period of time, such as during the times when they are on duty.

Figure 27:
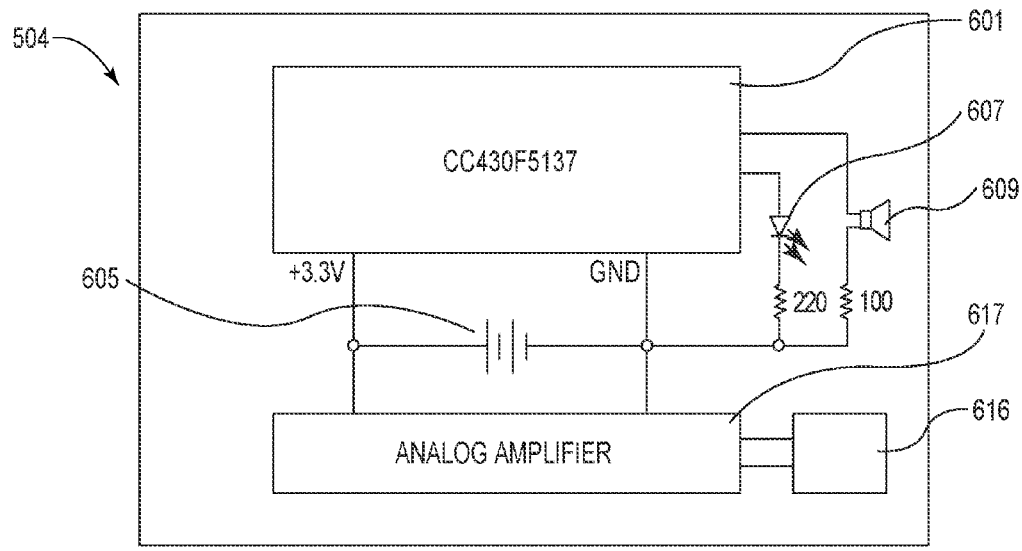
FIG. 27 is a more detailed block diagram of an example implementation for a compliance badge.

FIG. 27 is a more detailed block diagram of an example implementation for a compliance badge 504. In general, compliance badge 504 is an ID tag with RF and ultrasonic capability. Compliance badge 504 includes a microcontroller 601, batteries 605, at least one visible indicator such as a Light Emitting Diode (LED) 607, a speaker/chirp alarm 609, an ultrasonic receiver 616 and an analog circuit with amplifier 617. In this example, the microcontroller and memory may be implemented using system on a chip CC430F5137, available from Texas Instrument Inc., Dallas, Tex. Such a controller includes RF channels for communication with motion detector, zone emitter 528 and/or dispensers 530. Compliance badge 504 may also include touch switch (not shown) that allows HCW 2 to turn off any audible or visual alarms on the badge if necessary.

Figure 28:
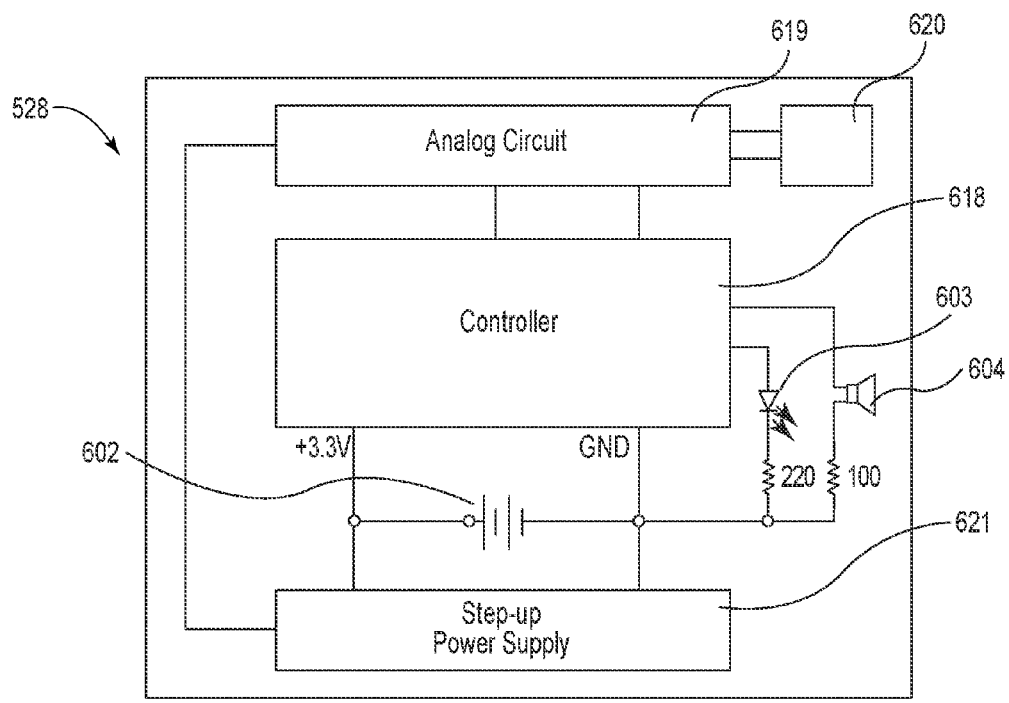
FIG. 28 is a block diagram of an example implementation for the ultrasonic zone emitter.

FIG. 28 is a block diagram of an example implementation for ultrasonic zone emitter 528. Zone emitter generates an ultrasonic patient protection zone, such as zones 526A and 526B, around a CCP. Zone emitter 528 includes batteries 602, step-up power supply 621, a low battery indicator, such as a Light Emitting Diode (LED) 603, a speaker 604, a controller 618, an analog ultrasonic driver circuit 619 and an ultrasonic transducer 620. Zone emitter 528 may include a variable shape ultrasonic emitter containing variable power settings for setting up protection zones of varying sizes, depending upon the CCP at issue. Zone emitter 529 may also provide a shaping function to the sonic coverage. In some examples, to extend battery life, zone emitter 229 may operate in a pulse mode, sending out the sonic coverage periodically, such as every 2-3 seconds. Zone emitter 529 may also be capable of sonic data transmission for a zone ID and/or low-battery alarm information may be transmitted to a compliance badge that enters into the protection zone.

Zone emitter 528 may be powered by AC power or by batteries 602. Controller 618 in some examples can be system on a chip CC430F5137, the same as controller 601 shown on FIG. 27 for compliance badge 504. Such a controller includes RF channels for communication with compliance badges 504 or motion detector 540. In the event of battery powered zone emitter 528, the wake-up signal broadcast by motion detector 540 may also be received by zone emitter 528 to activate ultrasonic transducer 620. In this way, zone emitter 528 may operate in a power conservation mode similar to that described for badge 504. In some examples zone emitter 528 may also include an RF transmitter, ultrasound receiver and motion detector. In such case, compliance badges 504 may also include an ultrasound transmitter for two-way communication with the zone emitter.

Figure 29:
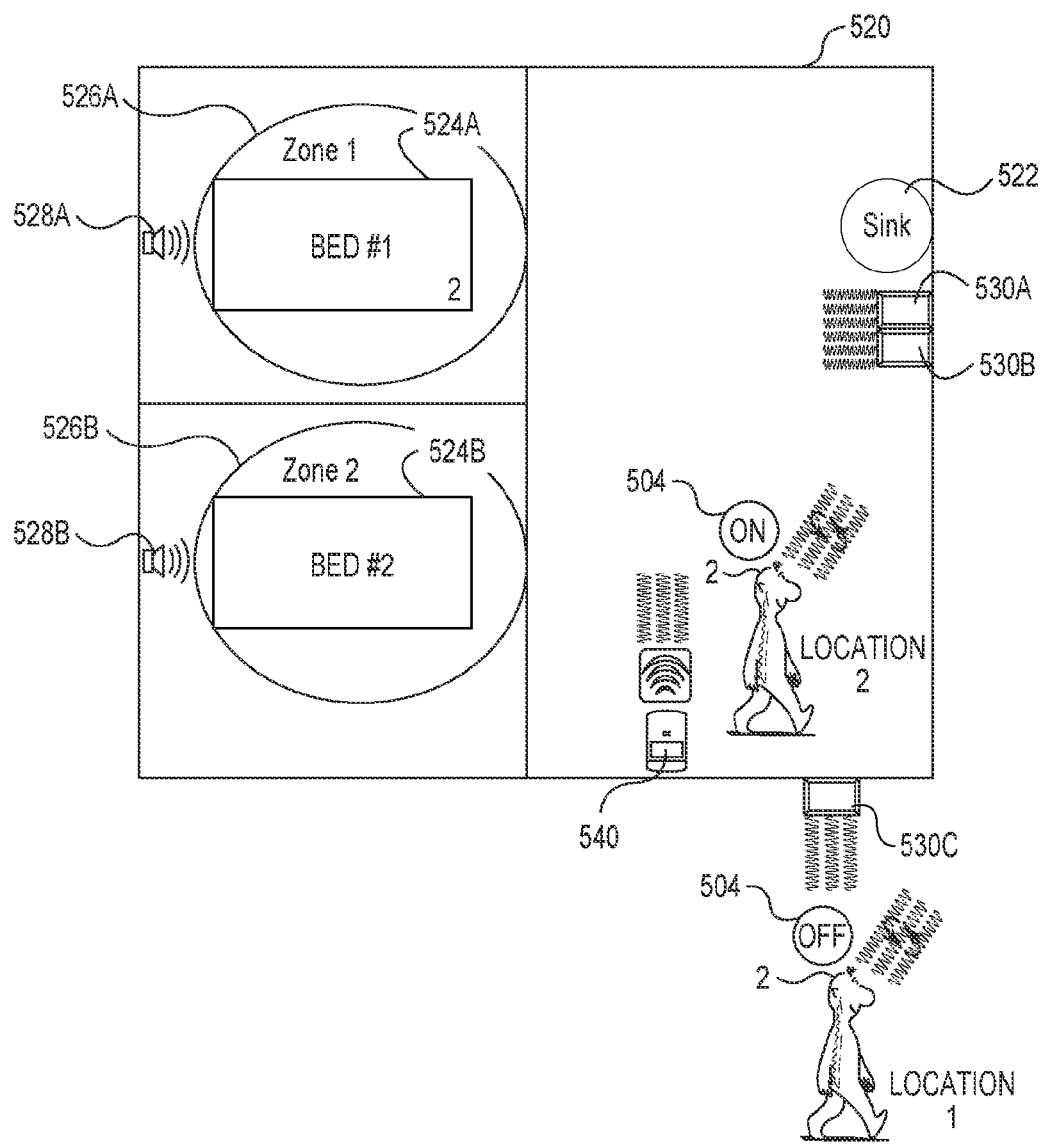
FIGS. 29-33 are diagrams illustrating example operation of the hand hygiene compliance system when a HCW enters and is present within a patient room AOC.

FIGS. 29-32 are diagrams illustrating example operation of the hand hygiene compliance system when a HCW 2 enters and is present within a patient room AOC 520. In FIG. 29, HCW 2 (at location 1) washes their hands at outside dispenser 530C. Location 1 may be in a hallway of the healthcare facility, for example. Note that while in location 1 the HCW is not present within a defined AOC, and that therefore the associated compliance badge 504 is in the power conservation mode. In power conservation mode, the ultrasonic receiver within badge 504 is off, as indicated in FIG. 23.

When HCW 2 washes their hands at dispenser 530C, dispenser 530C detects the dispense event, records it, and looks for a signal containing HCW identification information from a compliance badge 504 within range of the dispenser reader (or with non-HCW identification information if no ID data is detected). The dispenser then transmits dispenser data to the compliance badge 504, including, for example, dispenser id, product id, time and date stamp of the dispense event, battery life data, number of dispenses and number of dispense remaining until out-of-product, and/or other dispenser status information.

Dispenser 530C will also transmit the compliance rules associated with AOC 520. The compliance rules may include, for example, a zone interaction rule and a loitering rule. The zone interaction rule (or simply, zone rule) and the loitering rule are used by compliance badge 504 to analyze dispense events, AOC entry events and protection zone entry events to identify compliant and non-compliant hand hygiene events. The zone interaction rule defines the maximum allowable time between a dispense event and when a person is allowed to enter a patient protection zone. That is, the zone interaction rule defines the amount of time after occurrence of a dispense event within which the HCW must enter a protection zone in order for the dispense event to qualify as a compliant hand hygiene event. The loitering rule permits a HCW to leave a protection zone and return to the same protection zone within a defined period of time. The dispenser may also transmit product-specific compliance rules, if any. For example, certain hand hygiene products may have shorter or longer zone interaction times or loitering times than other hand hygiene products, for example.

In some examples, certain of dispensers 530 may be programmed not to transmit compliance rules. For example, for a dispenser 530 mounted on a common wall with a dispenser in a different AOC (for example, when two AOCs share a common wall) those dispensers may be programmed not to transmit compliance rules in the event that the compliance rules for the two AOCs are not the same. This would prevent badges in the first AOC from receiving compliance rules from dispensers located in the second AOC in the event that they are in range of the dispenser in the second AOC.

In addition to transmitting the compliance rules to badge 504 upon detection of a dispense event, dispenser 504 also resets a zone interaction timer that keeps track of whether the maximum allowable time as defined by zone interaction rule has expired. That is, detection of a dispense event results in a resetting of the zone interaction timer. Each hand hygiene event thus restarts the zone interaction timer and essentially starts a new dispense event/zone interaction cycle.

In FIG. 23, HCW 2 has entered patient room AOC 520. Upon detection of the entry event, motion detector 540 broadcasts a wake-up signal within the AOC. Upon receipt of the wake-up signal, badge 504 activates its ultrasonic receiver. Motion detector may also transmit a motion detector id, time and date stamp for the entry event, motion detector battery life assessment, and/or other motion detector status information. Motion detector 504 may also transmit the compliance rules associated with AOC 520. However, detection of an entry event does not reset the zone interaction timer. In this example, only dispense events reset the zone interaction timer.

In order for a dispense event to be considered a compliant hand hygiene event, the HCW must enter a protection zone before expiration of the zone interaction timer that is started when the dispense event occurs. For example, if the zone interaction rule states that the zone interaction time is 10 seconds and Dr. Jones washes their hands (the dispense event) at dispenser 530C at time t=0, Dr. Jones must enter either one of protection zones 526A or 526B before time t=10 seconds in order for the dispense event and the entry event to qualify as compliant hand hygiene events.

Figure 30:
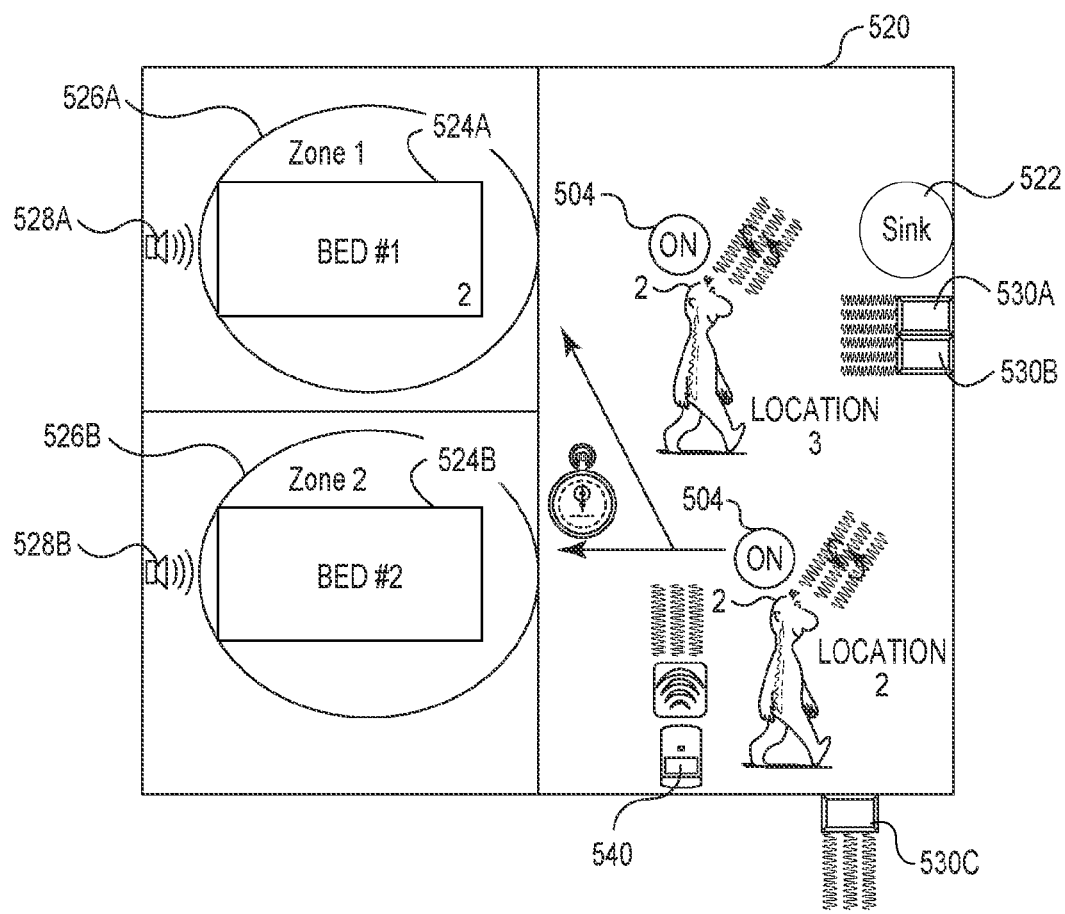

As shown in FIG. 30, once inside the AOC, to be compliant, HCW 2 may either enter one of protection zones 526A or 526B before expiration of the zone interaction timer. Alternatively, HCW 2 may wash their hands at one of in-room dispensers 530A or 530B. Assuming that dispenser 530A detects a dispense event, dispenser 530A obtains the HCW id information from the compliance badge 504. Dispenser 530A would then transmit the dispenser data for the dispense event, including the HCW id, the dispenser id, product id, time and date stamp of the dispense event, battery life data, number of dispenses and number of dispense remaining until out-of-product, and any other dispenser data for receipt by compliance badge 504.

Dispenser 530A will also transmit the compliance rules associated with AOC 520, and reset the zone interaction timer. Thus, each time a hand hygiene event is detected, the zone interaction timer is reset, thus permitting the HCW additional time to enter a protection zone.

Figure 31:
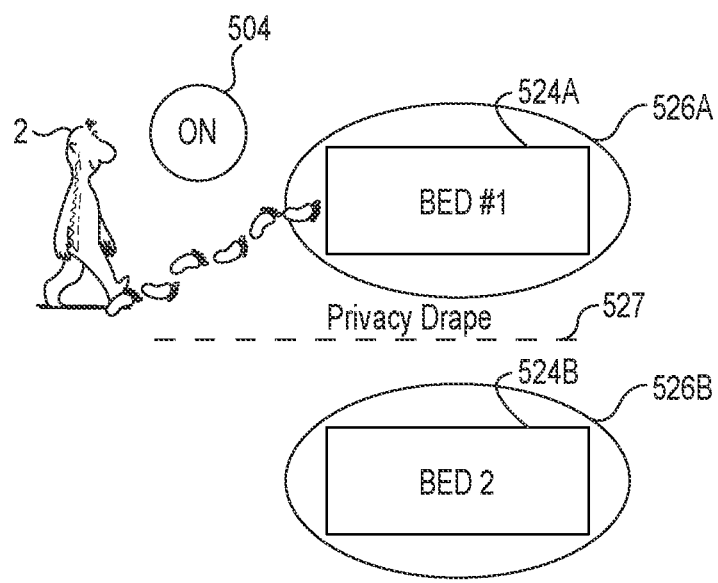

In FIG. 31, HCW 2 enters protection zone 526A for patient bed 524A (a "protection zone entry event" or simply "zone entry event"). Upon detection of the zone entry event (detected by badge 504 when it enters a protection zone) badge 504 checks whether the zone interaction timer is still active. If so, the detected zone entry event into protection zone 526A is a compliant event. Because the zone entry event is a compliant event, there is no alarm. Badge 504 registers the most recent dispense (in this example, the dispense event at dispenser 530A) and the zone entry event (in this example, the entry event into protection zone 526A) as a compliant hand hygiene event(s). Zone id information, battery status, and/or other zone emitter status information may also be transmitted from the zone emitter 528A to the badge 504.

Once a compliant zone entry event is detected, the zone interaction timer is canceled; that is, as long as HCW 2 remains in protection zone 526A, no alarm is generated as long as the zone id does not change (i.e., HCW 2 remains in the same zone) and the loitering rule (described below) is not violated.

Alternatively, if upon detection of the zone entry event the zone interaction timer has expired, badge 504 registers the dispense event and the zone entry event as non-compliant hand hygiene event(s). In addition, audible and/or visual alarms on badge 504 may be activated to alert HCW 2 that a non-compliant event occurred. Badge 504 may include a touch switch or other mechanism that enables the HCW to deactivate the alarm, or the alarms may time out after a predetermined period of time.

Figure 32:
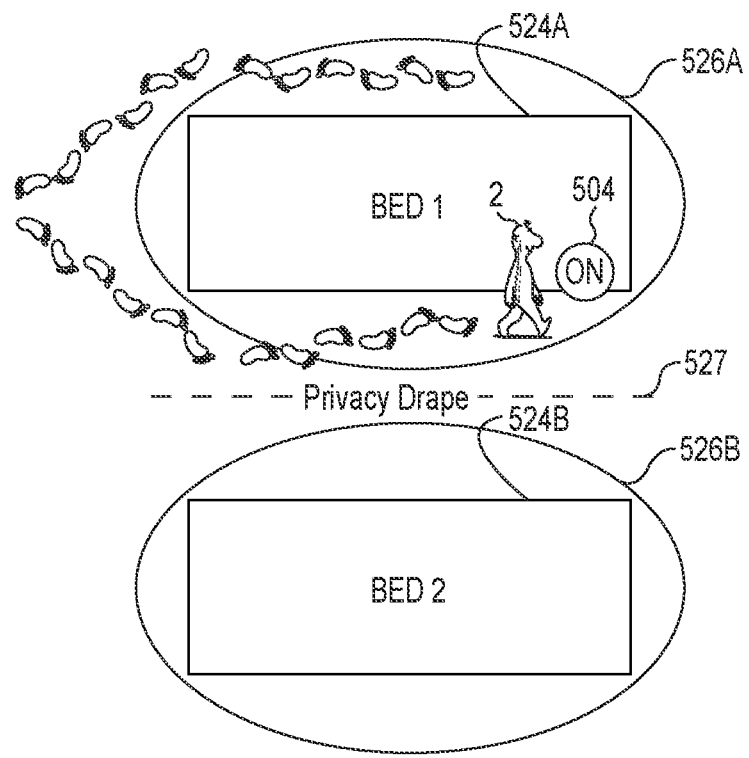

FIG. 32 illustrates operation of the loitering rule. In this example, HCW has already performed a compliant zone entry event into zone 528A and is working in zone 528A. At some later time, compliance badge 504 detects a zone exit event for HCW 2 as they leave zone 528A. Badge 504 detects when this zone exit event occurs, and saves the zone exit event data with a date and time stamp. Badge 504 also starts the loitering timer to monitor the length of time that HCW 2 remains outside of zone 528A. According to the loitering rule, if HCW 2 re-enters (a "zone re-entry event") the same protection zone (in this case, zone 528A) within the prescribed loitering time, the zone exit event and zone re-entry event are determined to be compliant events. However, if HCW 2 does not re-enter the same protection zone within the prescribed loitering time (without an intervening dispense event) the zone re-entry event is determined to be non-compliant. Badge 504 will register the non-compliant zone re-entry event and activate the audible/visual alarms on compliance badge 504 to alert HCW 2 to the non-compliant event.

Figure 33:
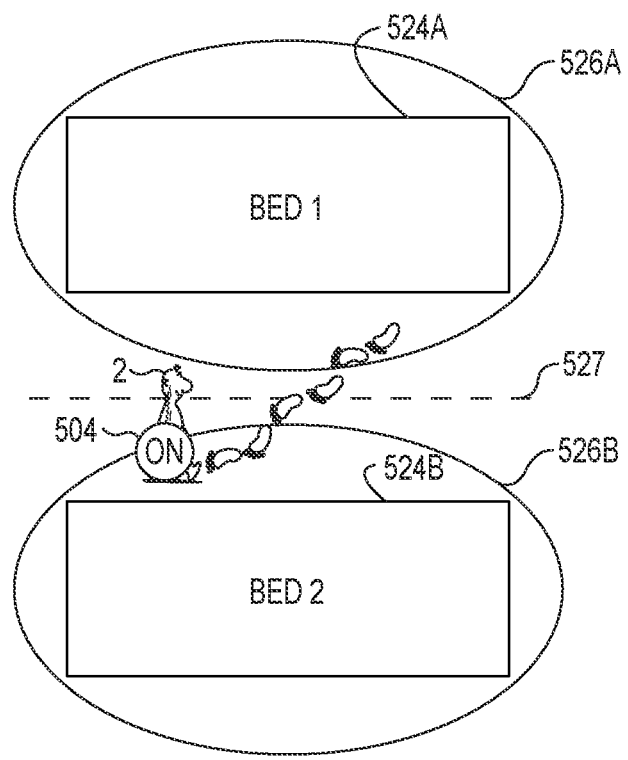

As another example of the loitering rule, FIG. 33 illustrates the case of HCW 2 exiting one protection zone (in this case zone 526A) and entering a different protection zone (in this case, zone 526B) within the prescribed loitering time. However, according to the loitering rules, entry into a second protection zone before expiration of the loitering clock for a first protection zone is defined as a non-compliant event. The non-compliant event (entry into zone 5286 without an intervening dispense event) would be stored by badge 504 as a non-compliant event. Also, even if the loitering timer for the first protection zone had expired, entry into a different protection zone without an intervening dispense event is defined as a non-compliant hand hygiene event.

The zone interaction rule(s) and the loitering rule(s) may be defined specifically for each AOC. Alternatively, compliance rules may be defined for specific types of AOCs. For example, the zone interaction rule may set the zone timer in the range of 5-20 seconds, for example. The loitering rule may define the loitering timer in the range of 3-8 seconds, for example. It shall be understood, therefore, that the zone interaction rules and/or the loitering rules may vary depending upon the AOC at issue, the hand hygiene product at issue, and the requests of the particular healthcare facility, and the disclosure is not limited in this respect.

Motion detector 540 continually monitors AOC 520 for movement to determine presence of a person or persons (other than the patient, who presumably spends most of their time in their patient bed and therefore would not trigger motion detector 540) in the AOC. Whenever movement is detected (regardless of whether it is a HCW, patient or other person in the room), motion detector 540 broadcasts the wake-up signal. This ensures that the ultrasonic receivers on each compliance badge 504 within AOC 520 are activated for as long as they remain within AOC 520. Thus, in FIGS. 29-33, compliance badge 504 is indicated as being "ON" when HCW 2 is inside of AOC 520. Motion detector 540 may broadcast the wake-up signal each time motion is detected within AOC 520, or may broadcast the wake-up signal at periodic intervals for as long as motion is detected. For example, motion detector 540 may broadcast the wake-up signal every 5-30 seconds for as long as motion is detected. Motion detector 540 may also continue to broadcast the wake-up signal for at least some defined period of time after motion has been detected (e.g., anywhere from 1-5 minutes, for example), to ensure that the ultrasonic receivers on the badges 504 remain activated even if a HCW is still present but standing relatively still within AOC 520.

Figure 34:
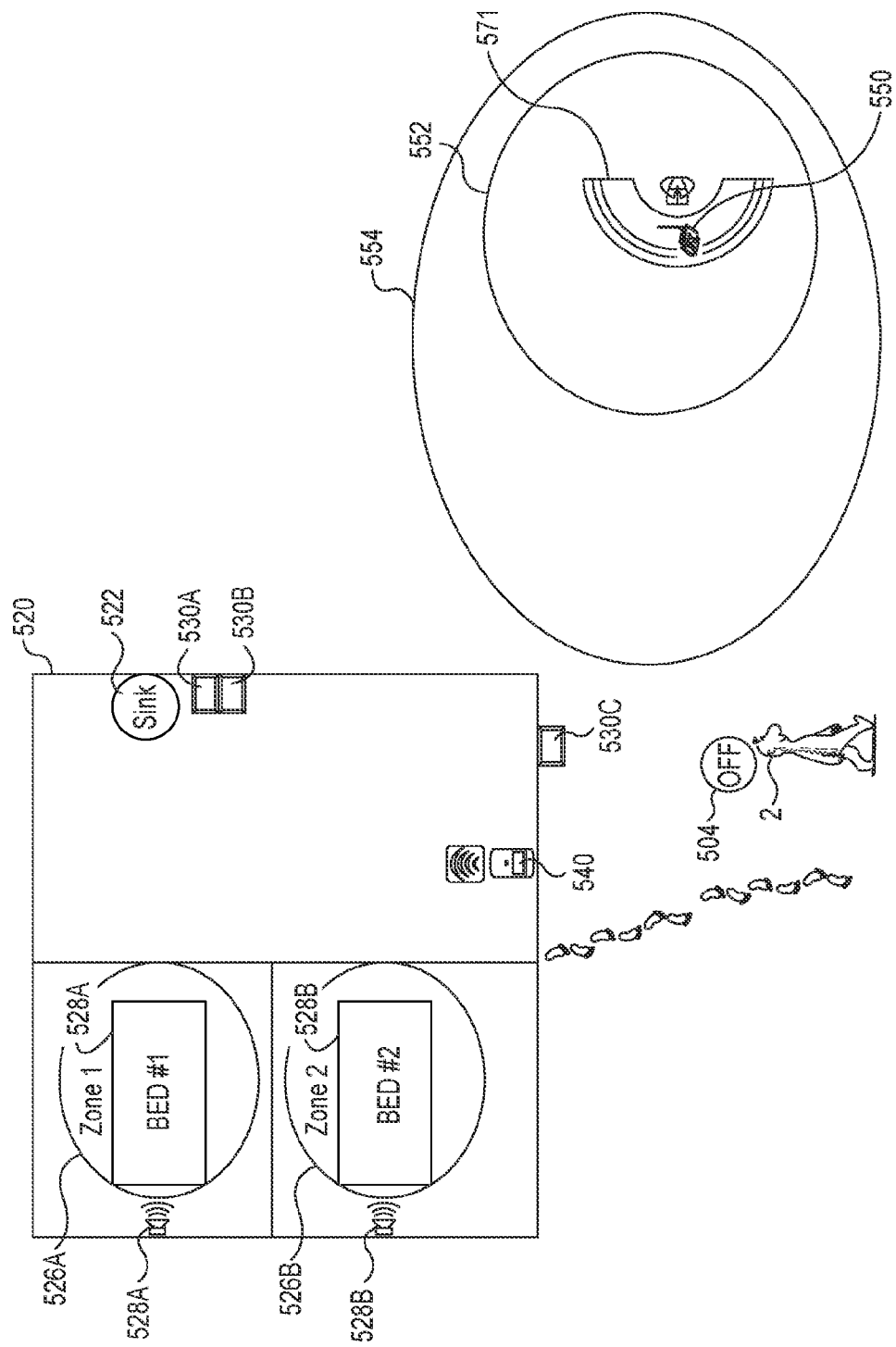
FIG. 34 illustrates an example operation of the hand hygiene compliance system after HCW exits AOC.

FIG. 34 illustrates an example operation of the hand hygiene compliance system after HCW 2 exits AOC 520. Badge 504 includes a power conservation module 613 (FIG. 26) that manages activation and power-down of ultrasonic receiver 616. As described above, badge 504 remains in power conservation mode, during which the ultrasonic receiver remains powered-down, if no wake-up signal is received. When badge 504 receives a wake-up signal, ultrasonic receiver is activated and a power-down timer is started. The power-down timer defines the length of time that ultrasonic receiver will remain active after the last wake-up signal is received. Each time a wake-up signal is received, the power-down timer is reset, ensuring that the ultrasonic receiver remains activated for as long as badge 504 is within range of a wake-up signal and is thus presumed to be present within an AOC. For example, as long as HCW 2 is present within AOC 520, badge 504 is within range of the wake-up signal sent by motion detector 540. Each time the wake-up signal is received, badge 504 resets its power-down timer, thus ensuring that the ultrasonic receiver remains activated for as long as HCW 2 remains in AOC 520.

When HCW 2 leaves AOC 520 and is out of range of motion detector 540, badge 504 will no longer receive the wake-up signal from motion detector 540 and, assuming HCW 2 does not receive wake-up signals from a motion detector associated with a different AOC, the power-down timer will not be reset and will eventually expire. Badge 504 will deactivate the ultrasonic receiver when the power-down timer expires. By so doing, the battery life of badge 504 may be extended because the ultrasonic receiver need not be active if HCW 2 is not present within an AOC. The power-down timer may be defined as any period of time that is reasonable under the circumstances, for example, the power-down timer may be of sufficient length to allow HCW 2 to step out and re-enter the AOC after a short period of time, etc. The power-down timer may be anywhere between 1 and 3 minutes, for example. However, it shall be understood that the disclosure is not limited in this respect.

In FIG. 34, HCW 2 has exited AOC 520, the power-down timer on badge 504 has expired, and the ultrasonic receiver on badge 504 has been powered-down. Badge 504 is thus indicated as being "OFF." Badge 504 now carries a payload of data concerning hand hygiene compliance. The data carried by badge 504 includes hand hygiene compliance data uniquely linked to HCW 2, such as AOC entry events, dispense events, zone entry events, and a record of compliant and non-compliant hand hygiene events. The data carried by badge 504 also includes redundant system status information (redundant in the sense that the same system status data may be carried by multiple compliance badges 504) such as dispenser battery status, zone emitter battery status, out-of-product alerts, number of dispenses, etc. The data carried by badge 504 is referred to herein generally as "badge data" (indicated by reference numeral 612 in FIG. 26, for example) and may include, for example, the hand hygiene data uniquely linked to HCW 2 as well redundant system status data.

The badge data may also include a data gauge that indicates generally the amount of badge data currently being stored by badge 504. Phrased another way, the data gauge may indicate whether or not sufficient data is stored on badge 504 to initiate download of the badge data when the compliance badge 504 comes within range of a data gathering station 550. Depending upon the requirements of the particular healthcare or other facility, badge data may not need to be downloaded whenever new badge data is available. For example, it may be sufficient to download badge data from each compliance badge every hour, every day or every week. The data gauge may thus be used to indicate whether a sufficient payload of data is present on badge 504 to initiate automatic download of the data. The data gauge may be programmed to reflect to the approximate length of time it may typically take to acquire a certain amount of data. In addition, regardless of the status of the data gauge, data may be automatically downloaded by data gathering stations 550 if data has not been received from a badge 504 for a predefined period of time.

Data gathering stations 550 are located at various places throughout the healthcare facility, such as nurse's stations, cafeterias, etc. In the example of FIG. 34, data gathering station 550 is located at a nurse's station 572. As mentioned above, data gathering station 550 initiates automatic download of badge data whenever a badge 504 is within range. In this example, data gathering station 550 includes multiple ranges or zones: a first download zone 552 (the download initiation zone) and a second download zone 554 (the maximum download zone).

Figure 35:
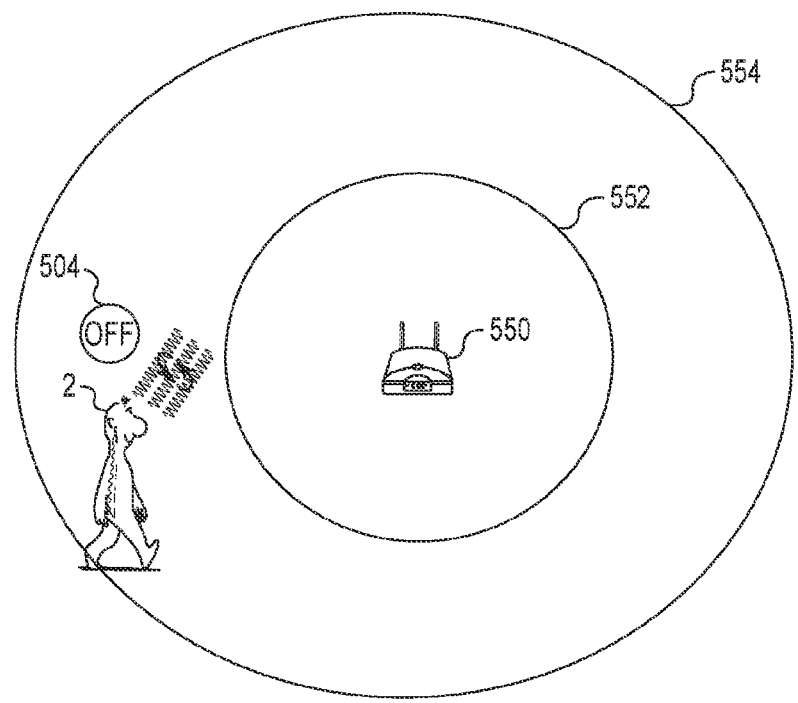
FIGS. 35 and 36 illustrate example operation of hand hygiene compliance system and automatic download of badge data by data gathering station.
Figure 36:
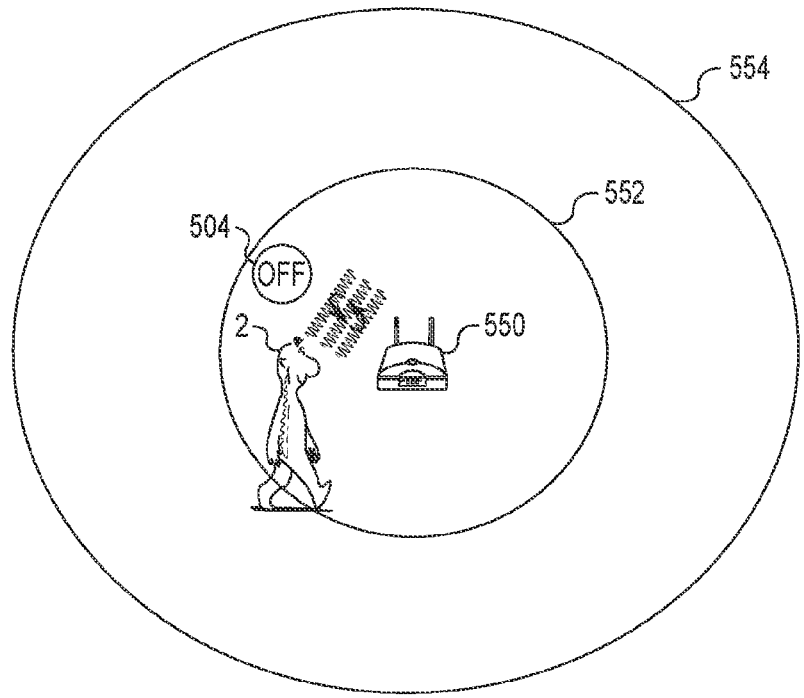

FIGS. 35 and 36 illustrate example operation of hand hygiene compliance system and automatic download of badge data by data gathering station 550. Data gathering station 550 does not initiate automatic download of badge data unless badge 504 is detected within download initiation zone 552. Thus, in FIG. 35, although badge 504 is present within maximum download zone 554, badge 504 ignores download requests until it enters download initiation zone 552. When badge 504 is detected within zone 552 (FIG. 36), data gathering station 550 initiates automatic download of badge data. For example, data gathering station 550 may include an RF transceiver that generates an RF interrogation signal and badge data download protocol to obtain badge data from badge 504. Download of badge data continues as long as badge 504 is detected within the maximum download zone 554. Thus, badge data transfer may continue over a broader range than is initially required to begin automatic download.

Once all of the badge data is transferred, badge 504 may enter a "data accumulation" mode and will ignore automatic badge data download requests from any of data gathering stations 550 until the data gauge indicates that the minimum data level has been obtained, or until a maximum time period without badge data download has elapsed.

In the event that HCW 2 leaves the maximum download zone before all available badge data is transferred, there are several possible courses of action. For example, badge 504 and/or data gathering station 550 may keep track of where the data transfer left off and transfer the remaining badge data the next time a badge data download is initiated. The data gauge may be adjusted to reflect the fact that some of the badge data was transferred, or it may be left where it was to ensure that the remaining badge data is downloaded the next time badge 504 receives a badge data download request. Alternatively, badge 504/data gathering station 550 may abandon the attempted badge data download and resend all of the badge data the next time badge 504 comes within range of a data gathering station.

Figure 37:
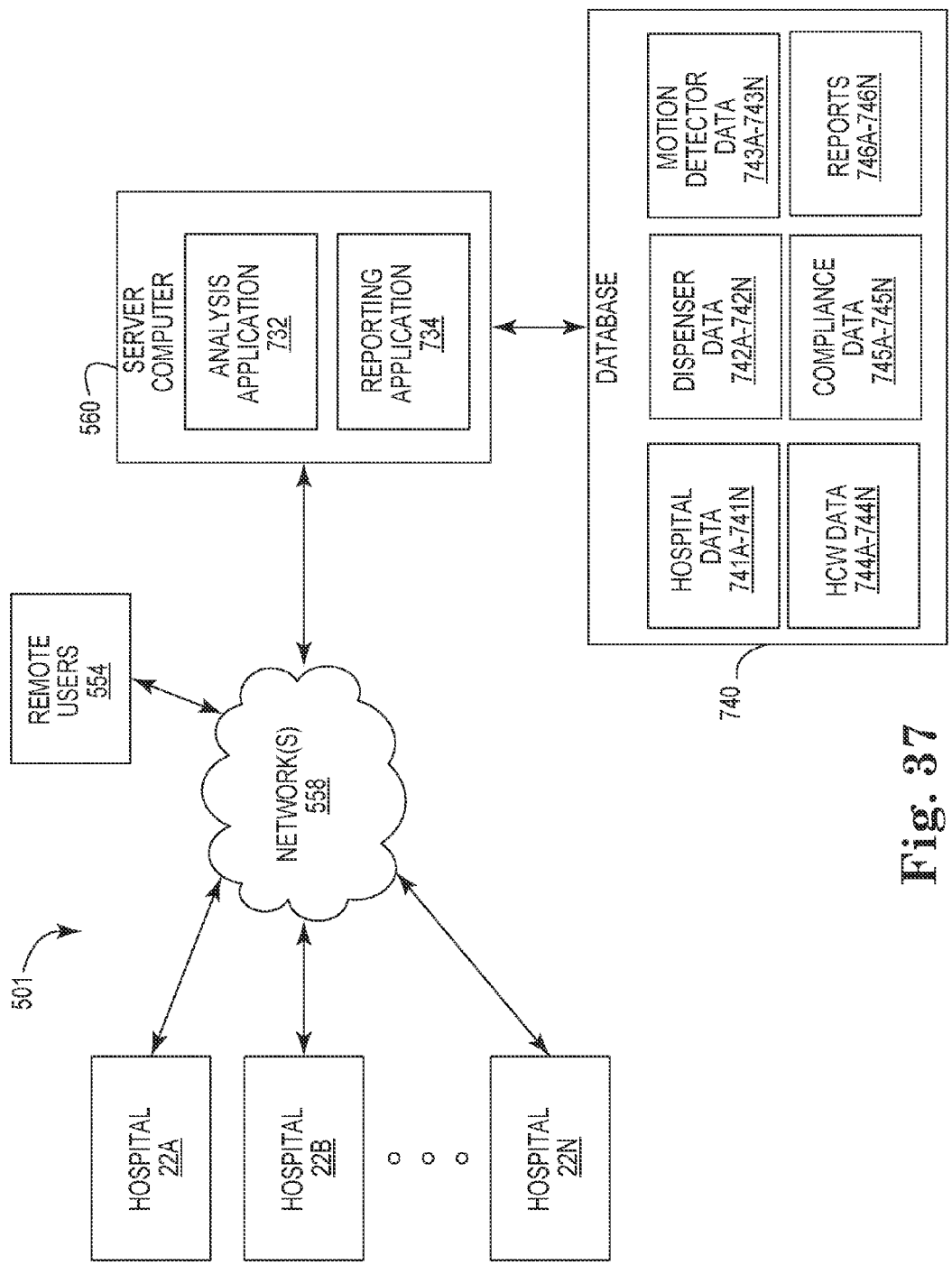
FIG. 37 is a block diagram illustrating an example communications environment within which the example hand hygiene compliance system may be used.

FIG. 37 is a block diagram illustrating an example communications environment within which the example hand hygiene compliance system 501 may be used. One or more hospitals or other healthcare facilities 22A-22N are coupled via network(s) 558 to server computer 560. Network(s) 558 may include, for example, one or more of a dial-up connection, a local area network (LAN), a wide area network (WAN), the internet, a cell phone network, satellite communication, or other means of electronic communication. The communication may be wired or wireless. Server computer 560 is coupled to a local server computer at each hospital 22A-22N via network(s) 558 to receive data related to hand hygiene compliance that is gathered and stored on local storage media at each hospital. Server computer 560 may also send commands, instructions, software updates, etc. to each hospital via network(s) 558. Server computer 560 may receive data or otherwise communicate with the hospitals on a periodic basis, in real-time, upon request of server computer 30, or at any other appropriate time.

The data received from hospitals 22A-22N, as well as other data associated with the operation of the hand hygiene compliance system, may be stored on a database 740. Database 740 may store, for example, hospital data 741A-741N associated with each of the hospitals 22A-22N, respectively; dispenser data 742A-742N associated with each of the hospitals 22A-22N, respectively; motion detector data 743A-743N associated with each of the hospitals 22A-22N, respectively; health care worker data 744A-744N associated with each of the hospitals 22A-22N, respectively; compliance data 745A-745N associated with each of the hospitals 22A-22N, respectively; and reports 746A-746N associated with each of the hospitals 22A-22N, respectively.

Hospital data 741A-741N may include data that uniquely identifies or is associated with the respective hospital or other healthcare facility 22A-22N. As such, hospital data 741A-741N may include, for example, hospital identification information, employee information, management information, accounting information, business information, pricing information, area of concern (AOC) information, critical control point (CCP) information, data gathering station information, information concerning those persons or entities authorized to access the reports generated by the hand hygiene compliance system, date and time stamps, caregiver identification, visitor identification and additional information relating to other aspects of the corporation or operation and other information specific to each individual hospital 22A-22N.

Dispenser data 42A-42N may include, for example, any information associated with operation of the hand hygiene product dispensers in the respective hospital 22A-22N. For example, dispenser data 42A-42N may include, without limitation, one or more of the following data types: dispenser id; dispenser type; dispensed product name; dispensed product type (e.g., sanitizer, soap, alcohol, etc.); dispensed product form (solid, liquid, powder, pelleted, etc.); dispensed product amounts (by volume, weight, or other measure); dispensing times, dates, and sequences; detected healthcare worker ids linked to specific dispensing events; empty dispenser indications; dispenser AOC location; compliance rules; and other information associated with or originating at the dispenser site, whether detected by a dispenser or by an associated device.

Motion detector data 743A-743N may include, for example, information concerning the entry and exit of compliance badged persons from a hospital room or other defined AOC in the respective hospital 22A-22N. For example, motion detector data 743A-743N may include, without limitation, motion detector id; motion detector type; physical location (e.g., hospital room number or other defined AOC within the healthcare facility); date of installation; maintenance records; detected person events, whether compliance badged or not; detected healthcare worker ids; date and time stamps; and other data associated with the motion detector modules of the respective hospital 22A-22N. Healthcare worker (HCW) data 744A-744N may include, for example, information concerning employees of the respective hospital 22A-22N. For example, HCW data 744A-744N may include, without limitation, HCW name, employee id number and/or other identification information; position (physician, nurse, physician assistant, physical therapist, EVS, etc.); work schedule; and other HCW related information for the healthcare workers in the respective hospital 22A-22N.

Compliance data 745A-745N may include, for example, all of the compliance information collected by the compliance badges associated with each of the respective hospitals 22A-22N. For example, compliance data 746A-746N may include, without limitation, records of compliant and non-compliant hand hygiene events, including compliant and non-compliant AOC entry and exit events, dispense events, and CCP entry and exit events, as determined by each compliance badge 504A-504N for each hospital 22A-22N.

Server computer 560 includes an analysis application 732 that analyzes the data received from each of hospitals 22A-22N and stores the results for each hospital 22A-22N in the database 740. Analysis application 732 may analyze the hospital data 741A-741N, dispenser data 742A-742N, motion detector data 743A-743N, HCW data 744A-744N, and/or compliance data 745A-745N either alone or in various combinations with each other to monitor hand hygiene compliance by individual HCW, type of HCW (e.g., nurses, doctors, EVS, etc.), individual departments, type of department, unit, ward, individual hospital, type of hospital, across multiple hospitals, or by various other selected parameters.

A reporting application 734 generates a variety of reports that present the analyzed data for use by the person(s) responsible for overseeing hand hygiene compliance at each hospital 22A-22N. Reporting application 734 may generate a variety of reports to provide users local to each hospital 22A-22N or remote users 554 with both qualitative and quantitative data regarding hand hygiene compliance at their hospital, and/or to compare data over time to determine whether improvement has occurred. Reporting application 734 may also users to benchmark hand hygiene compliance at multiple hospitals or other healthcare facilities.

Reports 746A-746N associated with each hospital 22A-22N, respectively, may also be stored in database 740. Examples of the reports that may be generated by reporting application 734 are described with respect to FIGS. 6A-6C. Reports 749A-749N may be accessed by users local to each hospital 22A-22N or by remote users 554 over one or more network(s) 558. One or more of the reports 749A-749N may be downloaded and stored on a local hospital computer, such as hospital server computer 555 shown in FIG. 23B, user computer associated with remote users 554, other authorized computing device, printed out in hard copy or further communicated to others as desired.

Local hospital computer 555 (FIG. 23B) or database may also store the above-described hand hygiene data (e.g., hospital data, dispenser data, motion detector data, HCW data, and/or compliance data) associated with that hospital. Hospital computer 555, database, or other local computer(s), may also include local analysis and reporting applications such as those described above with respect to analysis and reporting applications 732 and 734. In that case, reports associated with that particular hospital may be generated and viewed locally, if desired. In another example, all analysis and reporting functions are carried out remotely at server computer 560, and reports may be viewed, downloaded or otherwise obtained remotely. In other examples, some hospitals 22 may include local storage and/or analysis and reporting functions while other hospitals 22 rely on remote storage and/or analysis and reporting. Thus, it shall be understood that these storage, analysis and reporting functions may also be carried out locally or at some other location, and that the disclosure is not limited in this respect.

In another example, rather than setting up CCP protection zones around patient beds or other physical location within a healthcare or other facility, the critical control points could be defined as the patients themselves. In this example, each patient may be assigned a CCP zone tag that establishes a personalized protection zone around the patient. The personal protection zone is able to move around as the patient moves throughout various areas within the healthcare facility. Patients and/or hospital assets may be tracked or located using the combination of compliance badges/tags and an arrangement of AOCs set up around a hospital or other healthcare facility.

Figure 38:
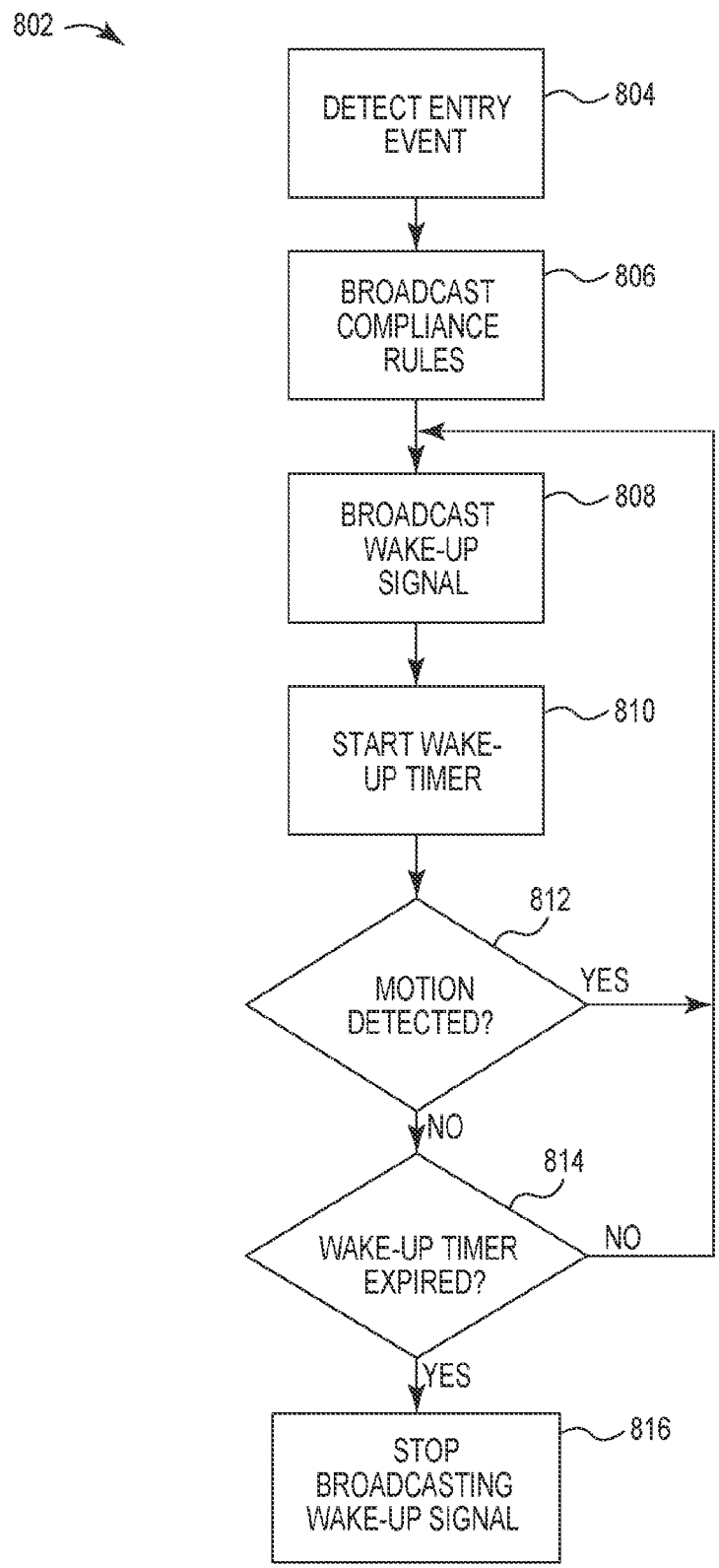
FIG. 38 is a flowchart illustrating another example process of operation for a motion detector module.

FIG. 38 is a flowchart illustrating another example process of operation for a motion detector module 540 (802). Upon detection of an entry event (804) motion detector 540 broadcasts the compliance rules specific to the associated AOC 520 (806). These compliance rules are then received and stored by any compliance badges within the AOC 520. Motion detector also broadcasts a wake-up signal (808). Receipt of the wake-up signal causes a compliance badge to activate its ultrasonic receiver and thus go from power conservation mode (in which the ultrasonic receiver is turned off to save power) to active mode (in which the ultrasonic receiver is turned on) in which compliance badge may detect entry and exit from protection zones established within the AOC, such as protection zones 526A and 526B.

Upon detection of an entry event, motion detector starts a wake-up timer (810). The wake-up timer determines the time frame within which motion must be detected in order for motion detector 540 to continue broadcasting wake-up signals. For example, if no motion is detected within AOC 520 for a predetermined period of time as governed by the wake-up timer, motion detector will stop broadcasting wake-up signals. This is because it may be assumed in this example that, if no motion is detected before the wake-up timer expires, no HCWs are present in the AOC, and that there are therefore no compliance badges 504 present within the AOC that must be kept active for monitoring of hand hygiene compliance. Motion detector 540 continues to monitor the AOC for motion (812). If motion is detected (812), and/or periodically for as long as the wake-up timer is not expired (814), motion detector continues to broadcast the wake-up signal to ensure that all compliance badges within AOC 520 remain in active mode for as long as they remain in AOC 520 (808). If motion is not detected (812) and the wake-up timer is expired (814) motion detector stops broadcasting the wake-up signal (816).

Figure 39:
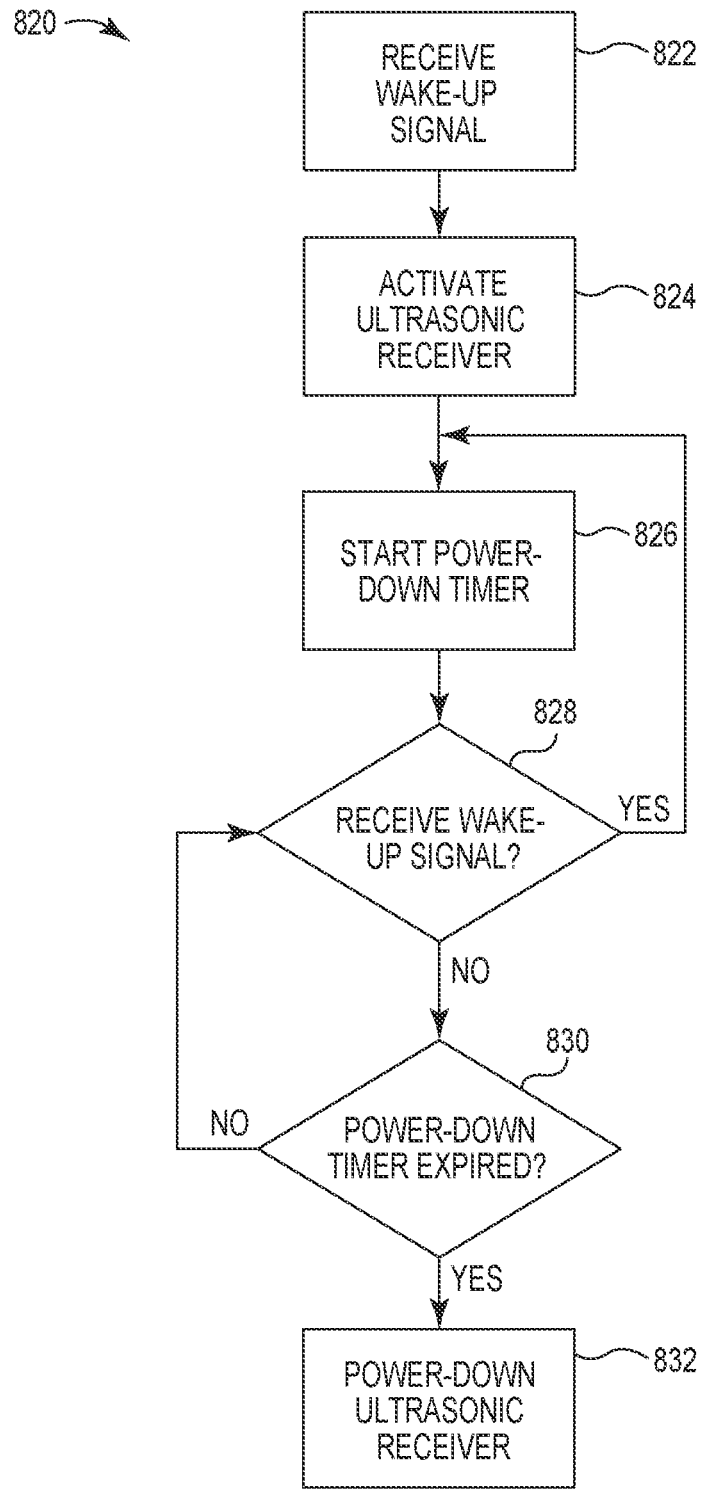
FIG. 39 is a flowchart illustrating an example wake-up process for a compliance badge.

FIG. 39 is a flowchart illustrating an example wake-up process (820) for a compliance badge 504. When a compliance badge 504 receives a wake-up signal broadcasted from a motion detector 540 (822), compliance badge 504 activates its ultrasonic receiver (824). At this time a power-down timer controlled by power conservation module 613 of compliance badge 504 is started (826). Each time a wake-up signal is received (828) the power-down timer is restarted (826). When no wake-up signal has been received (828) and the power-down timer has expired (830), compliance badge 504 powers down the ultrasonic receiver (832).

Figure 40:
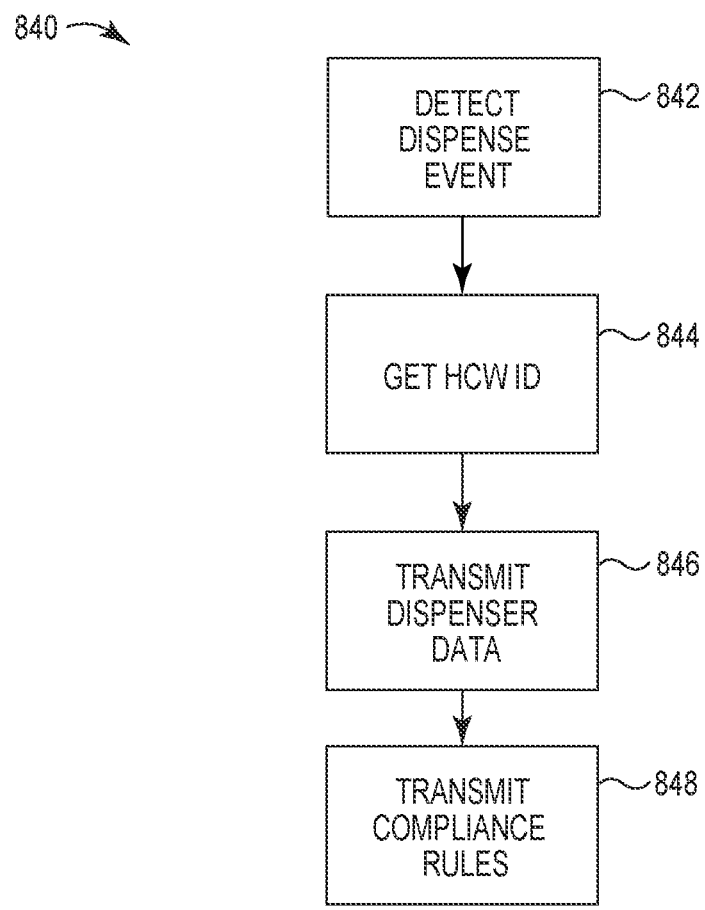
FIG. 40 is a flowchart illustrating an example process of operation for a dispenser module.

FIG. 40 is a flowchart illustrating an example process (840) of operation for a dispenser module, such as dispensers 530A-530C. When a dispenser detects a dispense event (842), the dispenser gets the HCW id information from the compliance badge 504 associated with the HCW who initiated that dispense event (844). One way dispenser module may do this is as described above with respect to dispenser module 16 as shown in FIGS. 16 and 17. The dispenser may then transmit the dispenser data (846) (e.g., data concerning the dispense event and associated HCW id data and date and time stamps, as well as battery status, total number of dispenses, number of dispenses remaining, out-of-product or low product status, and/or other dispenser status information, etc.). Dispenser 530 also transmits the compliance rules specific to the associated AOC 520 (848). This is may occur alternatively or in addition to the transmission of the compliance rules by motion detector 540.

Figure 41:
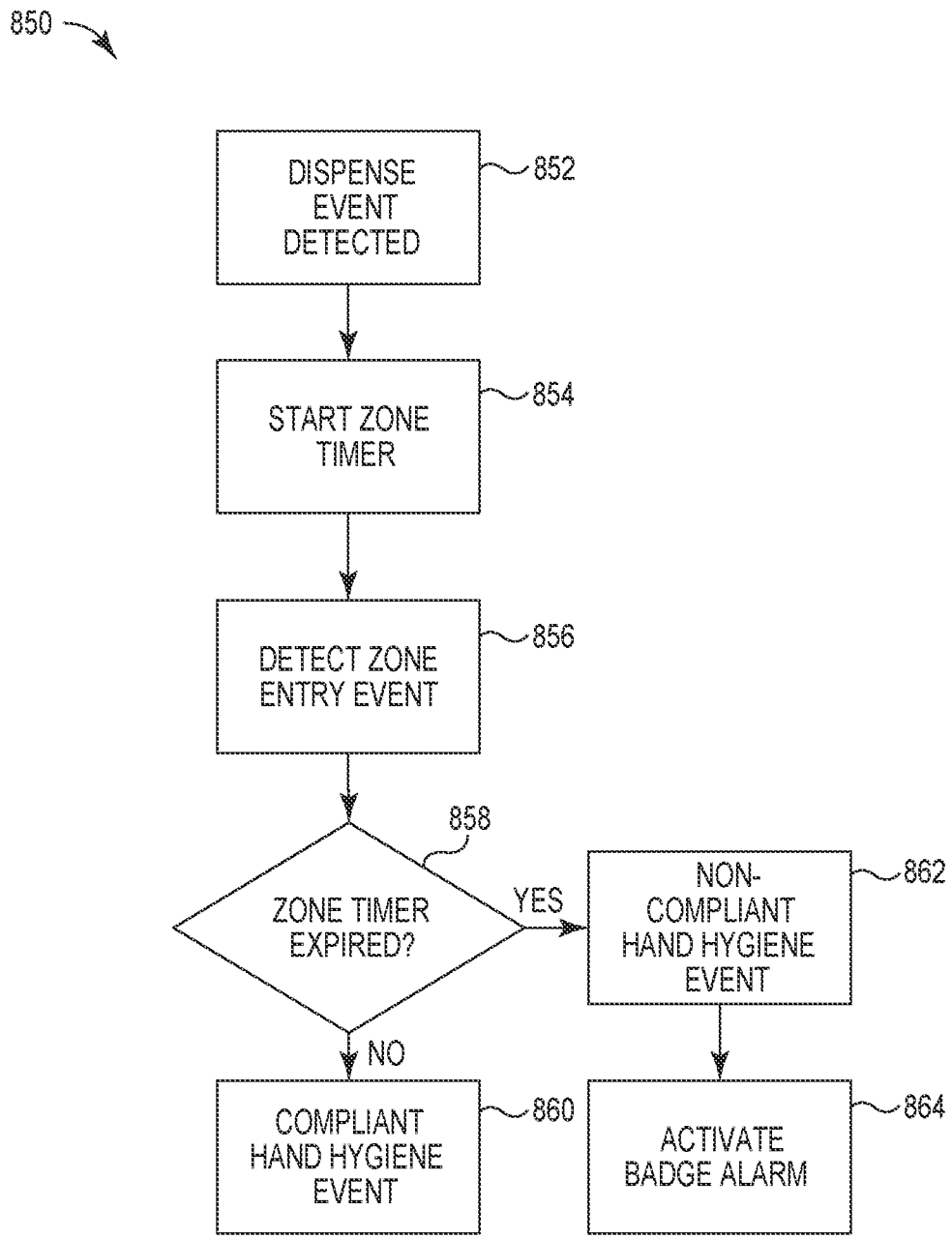
FIG. 41 is a flowchart illustrating another example process for a compliance badge.

FIG. 41 is a flowchart illustrating another example process (850) for a compliance badge. When a dispense event is detected (852) compliance badge 504 starts the zone interaction timer (854). When compliance badge 504 detects a zone entry event (856), compliance badge 504 determines whether the zone interaction timer has expired (858). If not, the zone entry event is recorded as a compliant hand hygiene event (860). Alternatively, if the zone interaction timer has expired (858), compliance badge 504 records the zone entry event as a non-compliant hand hygiene event (862) and may activate the badge alarm(s) to alert the HCW to the occurrence of a non-compliant event.

Figure 42:
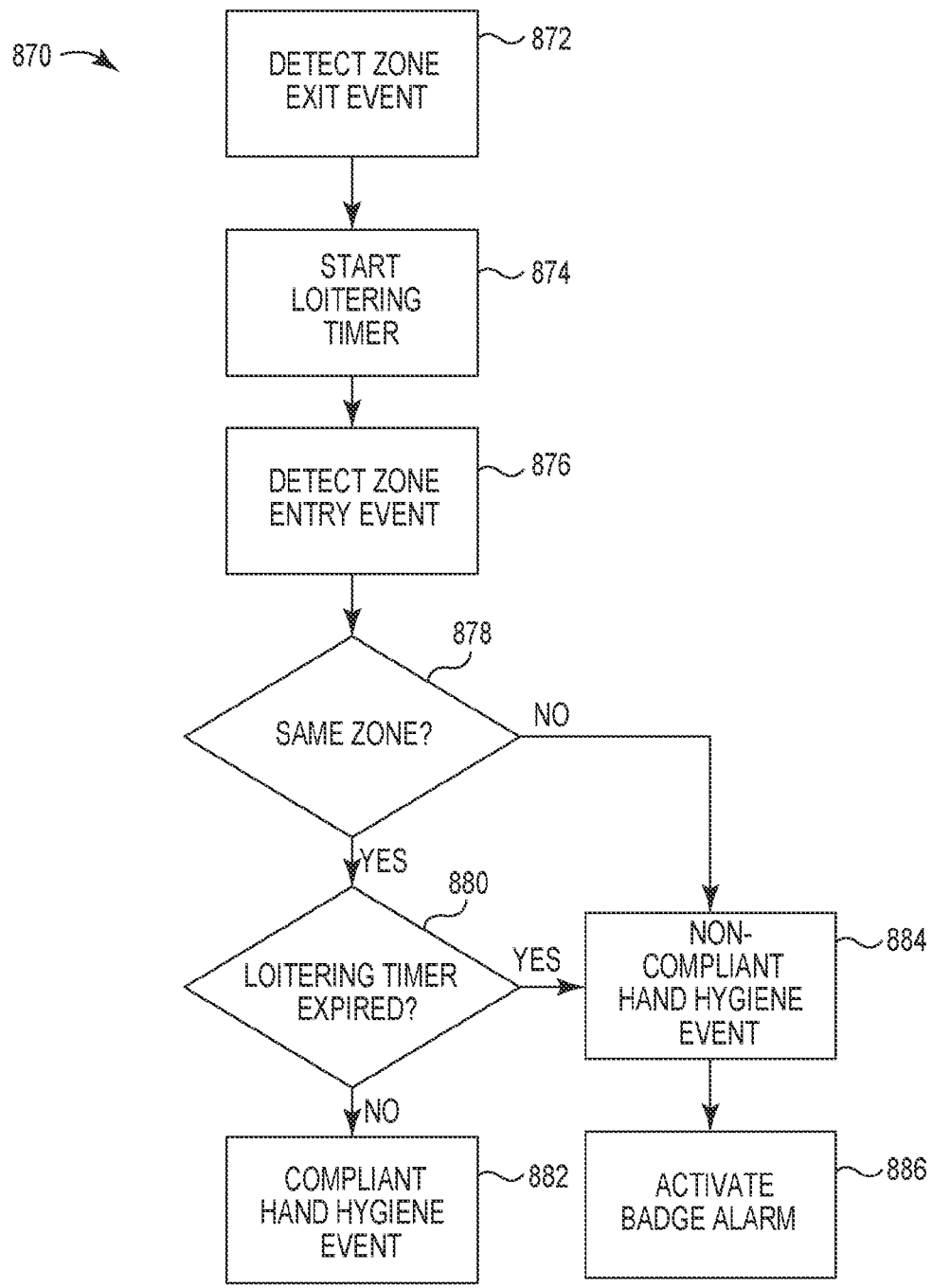
FIG. 42 is a flowchart illustrating another example process for a compliance badge.

FIG. 42 is a flowchart illustrating another example process (870) for a compliance badge. This process begins with the assumption that there has been detection of a previous compliant zone entry event, and the HCW is present within the protection zone. When compliance badge 504 detects a zone exit event (872), the loitering timer is started (874). If badge 504 detects another zone entry event (876), badge 504 checks whether the second zone entry event corresponds to the same protection zone as the initially compliant zone entry event (878). If so, badge 504 determines whether the loitering timer has expired (880). If the loitering timer has not expired, the second zone entry event is recorded as a compliant hand hygiene event (882).

Alternatively, if badge 504 detects a second zone entry event (876), and the second zone entry event does not corresponds to the same protection zone as the initially compliant zone entry event (878), badge 504 records the second zone entry event is recorded as a non-compliant hand hygiene event (884). Any badge alarms may also be activated at this point to alert the HCW to the occurrence of a non-compliant hand hygiene event. This is because, for purposes of hand hygiene compliance, a HCW should not be allowed to work in a first protection zone and enter into a second, different protection zone (and potentially carrying with him or her any contaminants from the first protection zone) without an intervening dispense event.

It should be noted that if at any time during any of the processes shown in FIG. 42 a dispense event is detected, compliance badge returns to execute the process shown in FIG. 41. In this way, each time a dispense event is performed, the associated HCW is permitted to enter any protection zone in the AOC, so long as it is done within the amount of time permitted by the zone interaction timer.

Figure 43:
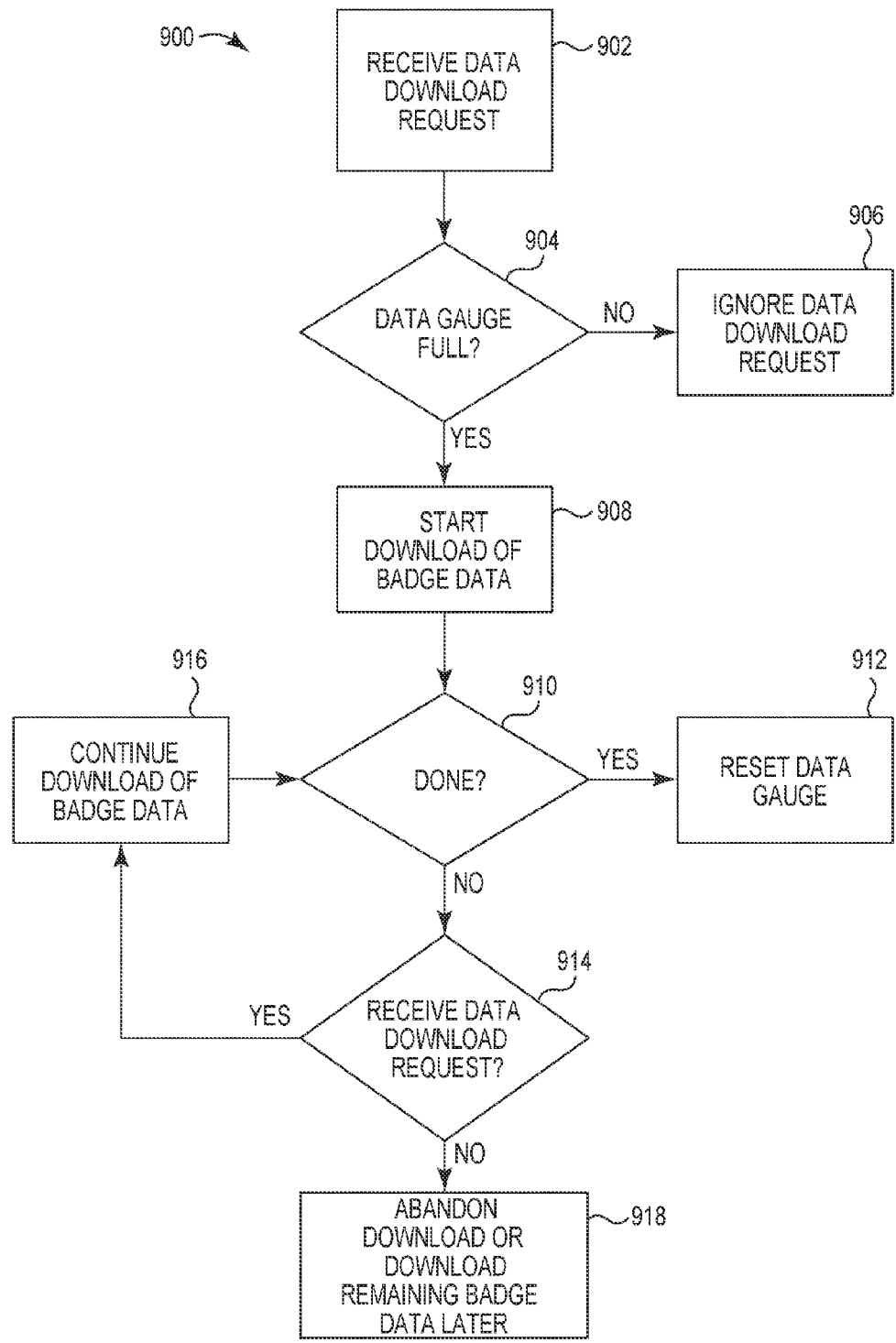
FIG. 43 is a flowchart illustrating an example badge data download process.

FIG. 43 is a flowchart illustrating an example badge data download process (900) executed by a compliance badge. When compliance badge 504 receives a data download request (902), compliance badge 504 checks whether its data gauge is full (904). If not, the badge may ignore the data download request (906). Badge 504 will continue to ignore all data download requests until the data gauge is full (904). If the data gauge is full, compliance badge 504 initiates a badge data download communication protocol with the data gathering station that sent the data download request (908). When the badge data download is complete (901), badge 504 resets its data gauge (912). Data gathering station periodically broadcasts data download requests throughout the maximum data gathering zone (e.g., maximum data gathering zone 554). Badge 504 continues to transmit badge data (916) as long it is within the maximum data gathering zone and is receiving download requests (914).

If at any point during the badge data download the badge 504 exits the maximum data gathering zone, badge 504 will no longer receive data download requests (914). This means that the badge is out of range of the data gathering station and cannot complete the badge data download (i.e., the badge data download was incomplete). At this point the badge 504 may wholly abandon the badge data download and re-attempt to transfer all of the badge data the next time it receives a badge data download request (918). Badge 504 may leave the data gauge at the full position to ensure that the badge data download is initiated the next time badge 504 receives a badge data download request. Alternatively, badge 504 may mark where the badge data transfer left off and continue the badge data download at some future time (918). In the event that an incomplete badge data download occurs and the remaining badge data is to be downloaded later, badge 504 may adjust the data gauge to indicate that a portion of the badge data has been downloaded, or may leave the data gauge at the full position to ensure that the badge data download continues the next time a data download request is received.

Although example zone emitters 528 are described herein as generating ultrasonic protection zones, and that compliance badges 504 include ultrasonic receivers for detecting entry and exit from the ultrasonic protection zones, it shall be understood that other implementations for generating protection zones and for detecting entry and exit from those zones could also be used without departing from the scope of the present disclosure. For example, zone emitters 528 could generate protection zones using radio frequency (RF), infrared (IR), microwave or any other appropriate frequency or frequency spectrum, or that the zone emitters could use motion detectors or other means of detecting presence within a protected zone, and the zone emitters and compliance badges would then include the hardware and software components associated with the chosen implementation. Likewise, although compliance badges 504, motion detectors 540 and dispensers 530 are described herein as communicating via RF signals, it shall be understood that other forms of wireless communication, including ultrasonic, infrared, microwave, etc., could be used without departing from the scope of the present disclosure.

Although certain examples are shown and described herein, it shall be understood that depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Further, it shall be understood that while various components of example hand hygiene systems are shown and described this disclosure, hand hygiene systems with additional or different components are contemplated within the scope of the disclosure. In various examples, one or more components of a hand hygiene system described in this disclosure may be omitted from a hand hygiene system, as will be appreciated by those of ordinary skill in the art.

FIG. 44A is a diagram illustrating another example hand hygiene compliance system 1000A in which a plurality of uniquely identifiable hand hygiene compliance badges, such as compliance badge 1004 worn by a wearer, such as HCW 2, and one or more dispensers, such as dispensers 1006A-1006C, monitor hand hygiene events in a healthcare or other facility in which monitoring of hand hygiene activities is desired. In these examples, each compliance badge may, but need not, store healthcare worker identification information. For example, each badge may include a unique badge identifier, so that all dispense events associated with each badge may be monitored and analyzed. In this example, a local or remote computer (such as local computer 555, server computer 560, or user computer 554) may include the ability to associate each badge with an individual HCW. However, it shall be understood that there may be circumstances in which it may be undesirable or unnecessary to specifically identify individuals and their associated hand hygiene activities, and that more generalized monitoring of hand hygiene compliance via unique badge identifiers may in some circumstances be sufficient.

Hand hygiene compliance system 1000A shares some of the components of hand hygiene compliance system 501 (FIGS. 23A and 23B) in that a plurality areas of concern (AOC) in which monitoring of hand hygiene compliance is desired are set up in various areas throughout a healthcare facility. At least one of a plurality of hand hygiene compliance badges, such as compliance badge 1004, is used to store and transmit hand hygiene compliance data to a data gathering station, in this case data gathering station 1020. Unlike the example of hand hygiene compliance system 501, however, hand hygiene compliance system 1000A does not include patient-centered critical control points (CCPs) or corresponding critical control point zone emitters 528. Hand hygiene compliance system 1000A may therefore provide some similar advantages to hand hygiene compliance system 501 while requiring fewer components and offering easier installation. The data gathering station 1020 may transmit the hand hygiene information to one or more local and/or remote computers as described above with respect to FIG. 1 or FIG. 23B, for example.

Hand hygiene system 1000A includes hand hygiene product dispensers 1006, in this case three dispensers 1006A, 1006B, and 1006C. In different examples, hand hygiene system 1000A may include fewer dispensers (e.g., one or two) or more dispensers, depending on and the physical layout and functional requirements of AOC 1002. Regardless, each dispenser 1006 includes an activation or event sensor that detects when a hand hygiene product is dispensed. This is referred to as a "dispense event." In this respect, each dispenser 1006 may operate in a similar manner to the dispensers described with respect to FIG. 8, 21C, or 23, for example. Further, each dispenser 1006 may include a wireless dispenser reader that detects presence of a compliance badge within range of the dispenser reader.

Dispensers 1006 may also communicate with the at least one compliance badge 1004. For example, when a dispense event is detected and presence of a compliance badge is detected, the dispenser may transmit a dispense event signal. The dispense event signal is indicative that a dispense event occurred, and may include dispenser identification information. The dispense event signal may also include, in some examples, status information associated with the dispenser, such as battery status, product type, fault conditions, total number of dispenses, total number of badged and/or unbadged dispenses, etc. For purposes of the present description, a "badged dispense" means a dispense of product to a person who has a compliance badge, that is, the dispenser detected a compliance badge within range at the time the dispense event took place. An "unbadged dispense" means a dispense of product to a person who does not have a badge; that is, the dispenser did not detect a badge at the time the dispense event took place.

Figure 44B:
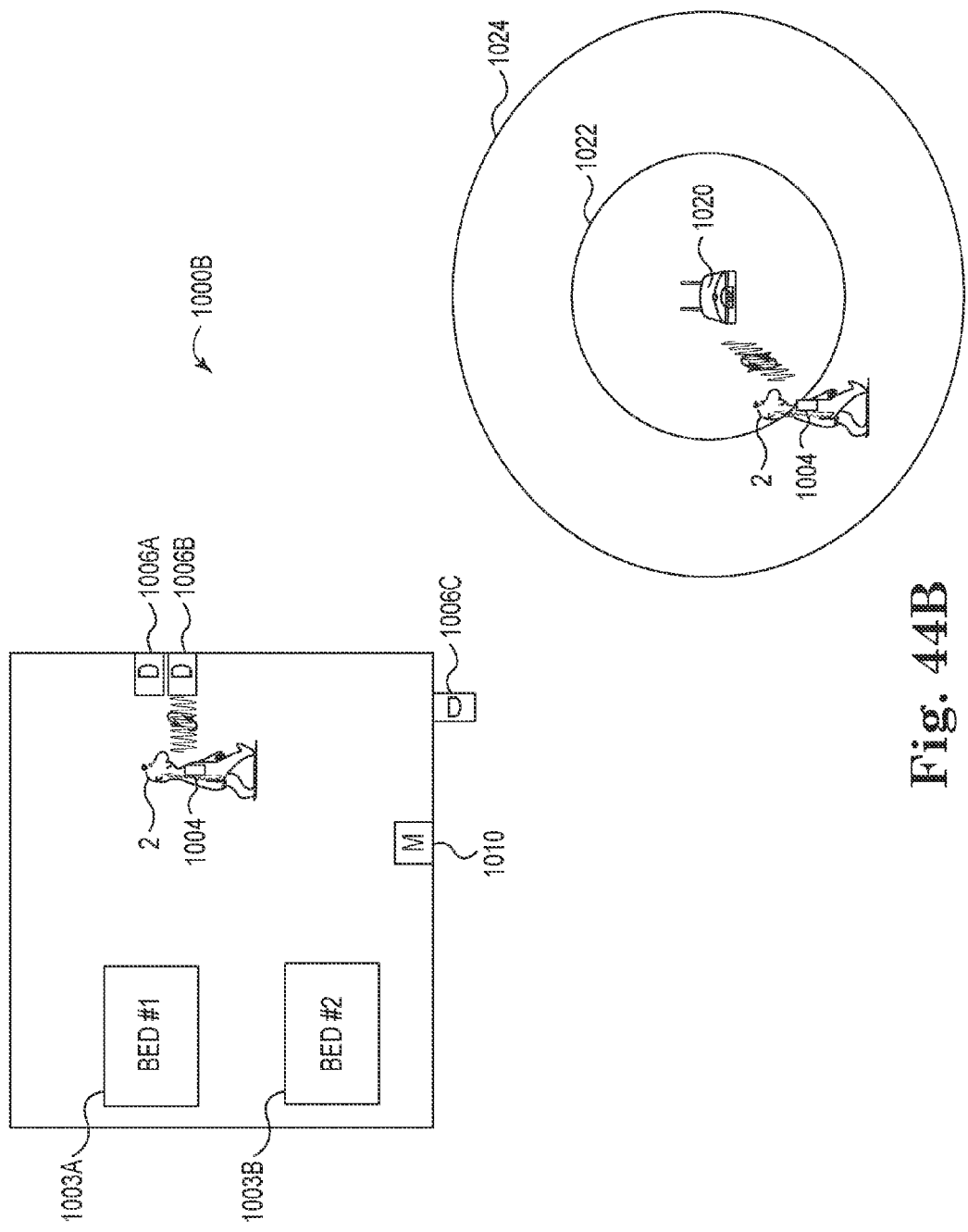
FIG. 44B is a diagram illustrating another example hand hygiene compliance system.

FIG. 44B is a diagram illustrating another example hand hygiene compliance system 1000B. Hand hygiene system 1000B is similar to hand hygiene system 1000A of FIG. 44A, except that system 1000B also includes a motion detector 1010. The hardware components and operation of motion detector 1010 may correspond to motion detector 540 described with respect to FIGS. 23 and 24, for example. In operation, motion detector 1010 detects movement within AOC 1002. For example, motion detector 1010 may detect movement within proximity to the entrance of an AOC 1002 (to detect entrance of persons into AOC 1002). This is termed an "entry event." Motion detector 1010 may also detect movement within AOC 1002 (to detect presence of persons moving within AOC 1002). If movement is detected, motion detector 1010 may perform one or more functions. For example, motion detector 1010 may send a "wake-up" signal to dispensers 1006. This wake-up signal may cause dispensers 1006 to enter an invitation mode, in which at least one dispenser 1006 activates one or more visual or audible indicators whose purpose is to remind the person entering the room of a hand hygiene opportunity. Motion detector 1010 may alternatively or in addition perform any additional functions attributed to motion detectors according to this disclosure.

In addition, motion detector 1010 may also communicate with the at least one compliance badge 1004. For example, when a movement is detected within the AOC, motion detector 1010 may transmit motion detector data for receipt by one or more of any compliance badges present in the AOC. Motion detector data may include, for example, battery status; motion detector id; motion detector type; physical location (e.g., hospital room number, or other defined area within the hospital, such as a standalone hand washing station, procedure room, lab, common area, operating room, therapy station, etc.); date of installation; maintenance records; detected person events, whether a person is wearing a compliance badge (HCW) or not (non-HCW); detected healthcare worker ids; date and time stamps (e.g., of an entry event); and other data associated with motion detector 1010.

Figure 45:
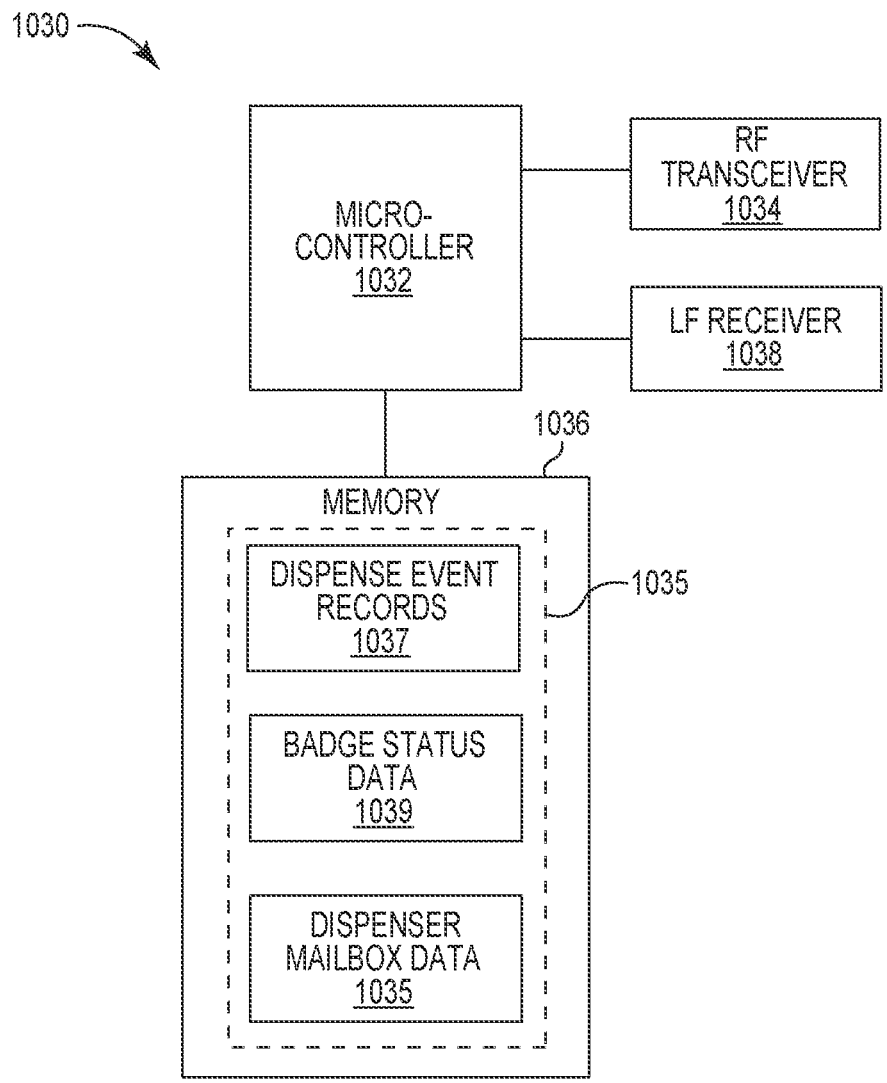
FIG. 45 is a block diagram of an example compliance badge.

FIG. 45 is a block diagram of an example compliance badge 1004. As discussed above, compliance badge 1004 receives, stores, and transmits various data to facilitate operation of hand hygiene system (such as system 1000A, 1000B, or any of the other hand hygiene compliance systems described herein). Compliance badge 1004 includes a microcontroller 1032, an RF transceiver 1034, and LF receiver 1038, and a memory 1036. RF transceiver 1034 communicates with dispensers 1006, a motion detector 1010 (if present), and data gathering stations 1020. In this example, an LF receiver receives LF (low frequency) wake-up signals broadcast by a dispenser upon detection of a dispense event and/or, in some examples, by a motion detector upon detection of an entry event. Microcontroller 1032 controls communication via RF transceiver 1034 and may also analyze various data including, for example, dispenser data and/or motion detector data, to monitor hand hygiene compliance or to log data concerning dispense events initiated by the HCW associated with the compliance badge. Memory 1036 stores software and data useful for the operation of badge 1030 such as, for example, dispense event records 1037, badge status data 1039, dispenser mailbox data 1035, and/or any other data generated or received by the badge 1004. Dispense event records 1037 may include, for example, a plurality of data records, each corresponding to a different dispense event initiated by the wearer of badge 1030. For example, each dispense event record stored in dispense event records 1037 may include a time and date of the dispense event, dispenser identification information, and/or any other appropriate dispense event data. Badge status data 1039 may include, for example, badge identification information, battery status, fault conditions, the time of last data download, data gauge level, and/or any other appropriate badge status information. Dispenser mailbox data 1035 may include, for example, a plurality of mailbox data records, each corresponding to the mailbox data associated with a different dispenser. Each mailbox data record may include, for example, dispenser status information such as battery status, the total number of dispense events, the number of badged dispense events, fault conditions, etc. for a different one of the dispensers in the hand hygiene system. In this way, the dispenser status information, badge status data, and/or dispense event records are physically carried to the data gathering station(s) as the wearer(s) of the compliance badge(s) move about the facility, where they are downloaded into the system for analysis and review.

Compliance badge 1004 may be implemented in a similar manner to some of the example compliance badges described herein. However, because example hand hygiene systems 1000A and 1000B do not include critical control point zone emitters described with respect to hand hygiene system 501, compliance badge 1004 need not include associated zone emitter hardware and software, e.g., ultrasonic receiver 616, ultrasonic receiver power conservation rules, and the like. Nevertheless, in some examples, a compliance badge that does include zone emitter functionality may be used in hand hygiene system 1000A and 1000B in addition to, or in lieu of, compliance badge 1004. That is, compliance badge 504 may be used in an environment where the full functionality of compliance badge is not enabled or perhaps is not used in every AOC.

With further reference to FIGS. 44A and 44B, hand hygiene systems 1000A and 1000B include one or more data gathering stations, such as data gathering station 1020. Data gathering station 1020 functions to retrieve data from compliance badge 1004 and, in some examples, transmit data to compliance badge 1004. The components and operation of data gathering station 1020 may be similar to the components and operation of data gathering station 550 described, for example, in FIGS. 23 and 34-37. For example, when HCW 2 leaves the AOC 1002 and comes within range of a data gathering station 1020, data gathering station 1020 compliance badge 1004 transmits its corresponding badge data for receipt by data gathering station 1020. In general, a healthcare or other facility may include a plurality of data gathering stations 1020 set up at various locations around the healthcare facility. Regardless, data gathering station 1020 may begin downloading badge data when compliance badge 1004 is within range of data gathering station 1020. In some examples, data gathering station 1020 includes a single download zone that is defined by where data gathering station 1020 begins downloading data. In other examples, data gathering station 1020 includes a plurality of different download zones. In the examples of FIGS. 44A and 44B, data gathering station 1020 includes a first download zone 1020 (e.g., a download initiation zone) and a second download zone 1024 (e.g., a maximum download zone).

Independent of the number or specific configuration of data gathering stations 1020, data gathering station 1020 may function to retrieve badge data from a plurality of compliance badges 1004. Badge data may then be used and/or distributed in a broader communication environment including, for example, a local hospital computer or other computer, a remote server computer, or to remote users, e.g., as described with respect to FIG. 1 and FIG. 37. Distribution to the communication environment may facilitate viewing, analysis and/or report generation based on badge data, thereby allowing hand hygiene compliance to be monitored or otherwise evaluated. In this manner, hand hygiene compliance systems 1000A and 1000B can function to monitor and evaluate hand hygiene compliance.

In at least some of the example hand hygiene compliance systems shown and/or described herein, conservation of power in one or more of the various system components may be addressed, if desired. For example, the battery life of the compliance badges and/or other components of the system (that is, those that may be battery powered) may impact the effectiveness of the system. Reasons for this may include the possibility that healthcare workers may be ill-inclined to use badges that require frequent battery replacement, or to replace them with a frequency sufficient to ensure continuous or near continuous operability of the badge. When badges or other system components are not operational, the opportunity to collect data relevant to hand hygiene compliance associated with those components is lost. In addition, if healthcare workers or other employees of a facility in which hand hygiene is to be monitored find the use of the compliance badge to be cumbersome due to shorter than desired battery life, this may lead to a tendency not to use the compliance badge or not to change the batteries as needed, further reducing opportunities to collect hand hygiene compliance data.

As discussed with respect to FIG. 16, for example, a dispenser module may spend at least some of its time in a low power "sleep mode." Operation of a dispenser in this way may serve to reduce power consumption and preserve battery life. A command to enter invitation mode, detection of an entry event, movement in proximity to the dispenser, or detection of a dispense event are various factors that may be used to "wake up" the dispenser.

An example communication protocol between a dispenser and a compliance badge for an example system such as that shown in FIG. 44A that attempts to minimize power usage in a compliance badge will now be described with respect to FIGS. 46 and 47.

Figure 46:
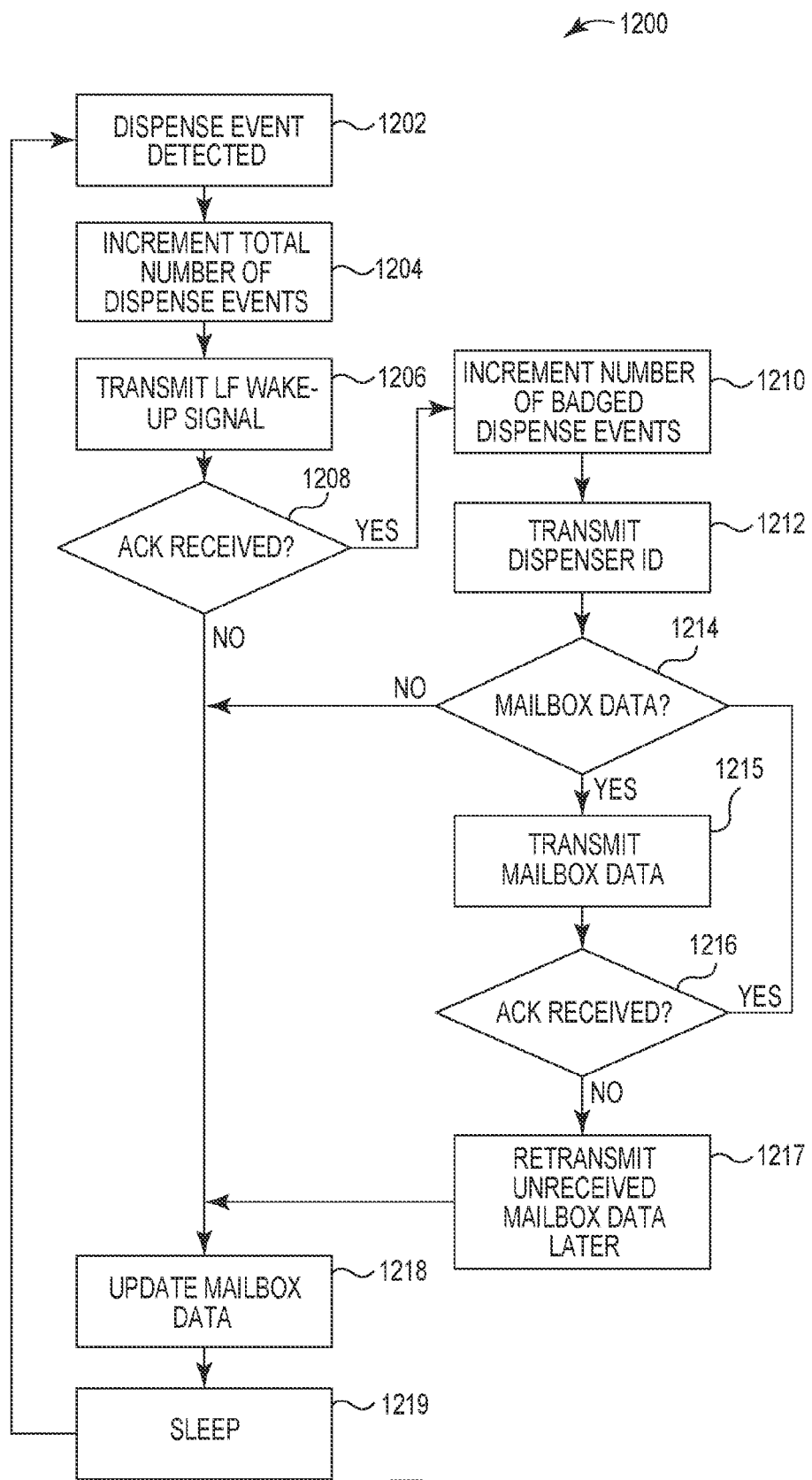
FIG. 46 is a flowchart illustrating an example process by which a dispenser communicates with a compliance badge
Figure 47:
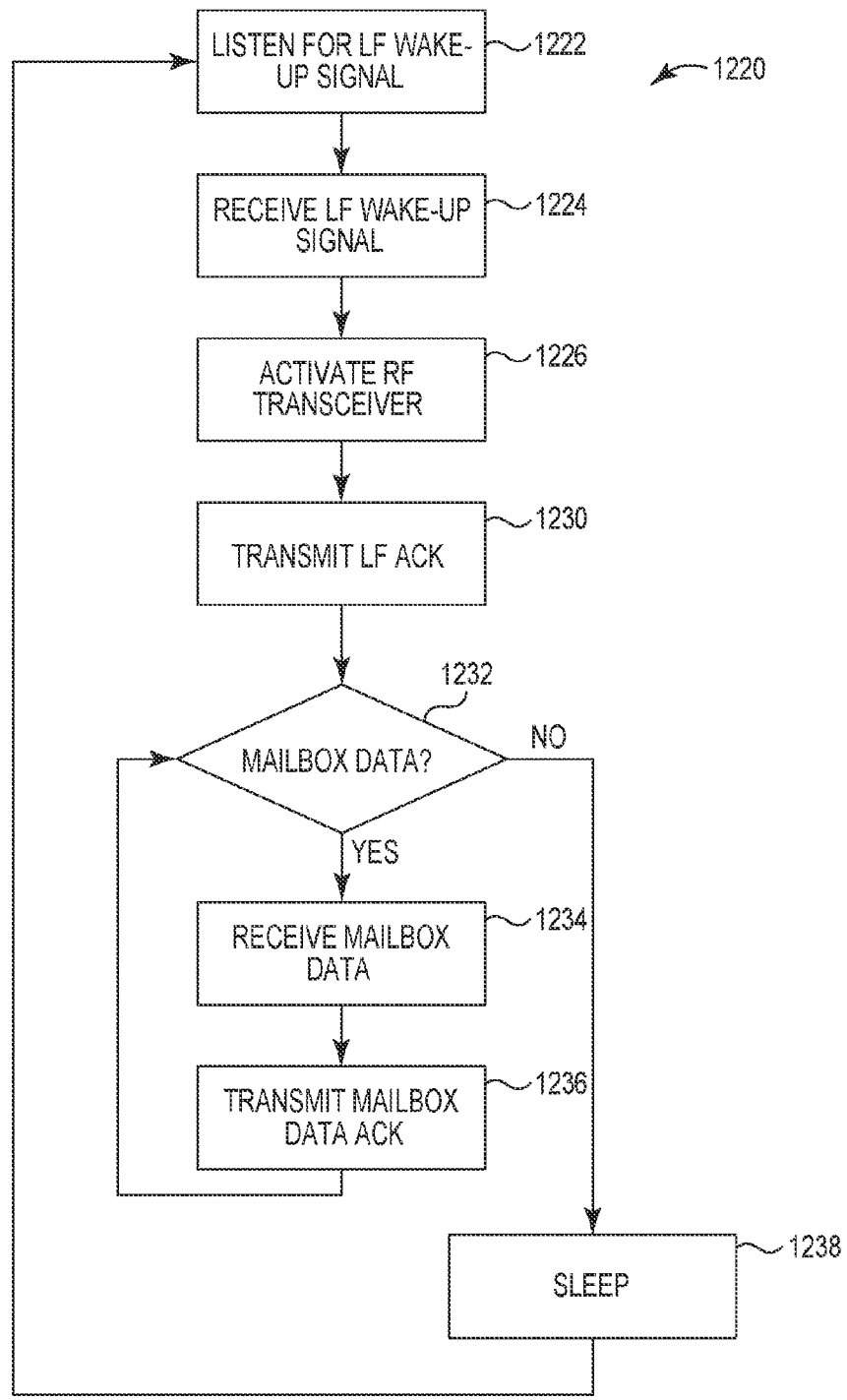
FIG. 47 illustrates and example process by which a compliance badge may communicate with a dispenser.

FIGS. 46 and 47 are flowcharts illustrating example processes (1200, 1250) executed by a dispenser and a compliance badge, respectively, during a communication session. For purposes of description, the process of FIG. 46 will be described with reference to a compliance badge operating in a system such as system 1000A in FIG. 44A. The disclosure is not limited in this respect, however, and other compliance badges and hand hygiene compliance systems as described herein may employ the process of FIG. 46.

Figure 48:
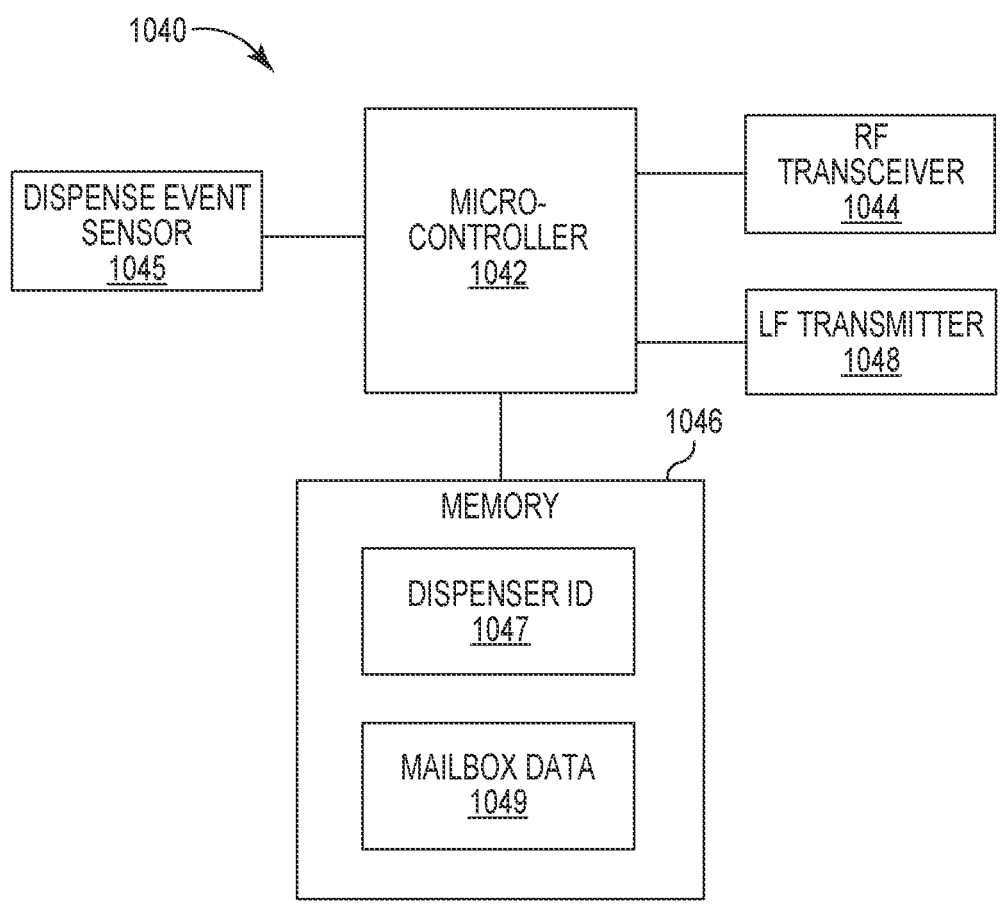
FIG. 48 is block diagram of an example dispenser.

In this example, the compliance badge (such as compliance badge 1030 shown in FIG. 45) includes an RF transceiver (such as RF transceiver 1036 as shown in FIG. 45) for communication with one or more dispensers and/or other system components (if present) and an LF receiver (such as LF receiver 1038 as shown in FIG. 45). The one or more dispensers (such as dispenser 1040 shown in FIG. 48) include an RF transceiver (such as RF transceiver 1044 as shown in FIG. 48) for communication with the compliance badges and an LF transmitter (such as LF transmitter 1048 as shown in FIG. 48). In this example, each dispenser may store dispenser identification information (such as dispenser id 1047 in FIG. 48) and mailbox data (such as mailbox data 1049 in FIG. 48). Dispenser id 1047 includes dispenser identification that uniquely identifies the dispenser. Mailbox data 1049 includes status data associated with the dispenser such as battery status, product status, product type, the total number of dispenses, the total number of badged dispenses, fault conditions, etc.

FIG. 46 shows the process (1200) by which a dispenser may communicate with a compliance badge. The dispenser detects the dispense event (1202). For example, dispense event sensor 1045 shown in FIG. 48 may detect activation of the dispenser by a user via a button or push bar, dispensation of chemical product, touch-free detection of a user's hands, etc. The dispenser increments the total number of dispense events (1204). The dispenser broadcasts a LF (low frequency) wake-up signal (1206). For example, when dispense event sensor 1046 detects a dispense event, microcontroller 1042 may instruct LF transmitter 1048 to broadcast a LF wake-up signal. In general, the term "LF" refers to radio frequencies in the range of 30 kHz-300 kHz. The LF transmitter 1048 may transmit a 134 kHz wake-up signal, for example. The LF wake-up signal is a relatively lower power, lower range signal as compared to those transmitted and received by the RF transceiver in either the compliance badge or the dispenser. The LF wake-up signal may include dispenser identification information. The LF wake-up signal may also specify an RF (900 MHz, for example) channel over which dispenser-badge communication will occur. Alternatively, the dispenser identification information may be sent via the RF channel specified in the LF wake-up signal.

Due to its proximity at the time of the dispense event, the compliance badge associated with the healthcare worker that initiated the dispense event is highly likely to receive the LF wake-up signal, although other badges present in the AOC may also receive the LF wake-up signal. When a compliance badge receives the LF wake-up signal, the compliance badge's microcontroller (e.g., microcontroller 1036 of FIG. 45) activates the RF transceiver (e.g., RF transceiver 1034) on the compliance badge so that the badge may communicate with the dispenser. In this example, the compliance badge may transmit and RF acknowledge signal (ACK) acknowledging that it received the LF wake-up signal and is ready to communicate with the dispenser.

After transmitting the LF wake-up signal (1206) the dispenser may determine whether the acknowledgement (ACK) is received from a compliance badge (1208). If no acknowledge of the LF wake-up signal is received (1208), then the dispense event was likely initiated by an unbadged person. The dispenser updates the mailbox data (1218) and returns to sleep mode (1219) to await detection of anther dispense event.

If an acknowledge of the LF wake-up signal is received (1208), then the dispense event was likely initiated by a person wearing a compliance badge. The dispenser may increment a badged dispense event counter (1210). This counter may be used to keep track of the number of badged dispenses experienced by the dispenser. The dispenser may also transmit the dispenser identification information (1212) uniquely identifying the dispenser. The badge associates the dispenser identification information with the dispense event, along with a time and date stamp, and stores this data in a dispense event record (such as dispense event records 1037 as shown in FIG. 45), as discussed below.

The dispenser determines whether mailbox data is to be sent (1214). Whether or not mailbox data is to be sent may depend, for example, on whether the dispenser has a predetermined amount of mailbox data stored. Mailbox data may also be sent according to a schedule, such as after every predetermined number of dispense events (e.g., after every 10 dispenses, after every 25 dispenses, or other appropriate number of dispenses, etc.), on a periodic schedule (e.g., every 3 hours, once per day, or other appropriate time period, etc).

If the dispenser is to transmit mailbox data (1214), the dispenser transmits the mailbox data (1215). In this example, a predetermined number of mailbox data records are sent. If a mailbox data acknowledgement from a compliance badge is not received (1216) the dispenser may assume that the transmission of the mailbox data failed and may retransmit the unreceived mailbox data at a later time (1217). If a mailbox data acknowledgement from a compliance badge is received (1216), the dispenser checks to see if there are additional mailbox data records to be sent (1214). For example, a predetermined number of mailbox data records may be sent, an ACK received, more records sent, etc., until all of the mailbox data is sent or until the badge is out of range. Once the dispenser does not receive a mailbox data acknowledgement (1216) (e.g., because the badge has gone out of range or because of an error) or the dispenser has sent all of its mailbox data (1214), the dispenser updates its mailbox data (1212) and returns to sleep mode (1213).

In this example, by not transmitting mailbox data at each dispense event, battery life on the compliance badge may be increased. However, it shall be understood that all mailbox data may be transmitted at each dispense event rather than saving mailbox data until some future time, and it shall be understood that the disclosure is not limited in these or other respects.

The badge may use a protocol to determine how any received mailbox data is to be stored. If the badge does not have enough room to store a new mailbox record, for example, it may drop its oldest record. As another example, if the badge already has a mailbox record for the dispenser, it may replace the older record with the new record. In addition, the dispenser may use the RSSI (receive signal strength indicator) information from the badge to determine which badge to communicate with in the event two or more badges are within range of the dispenser when a dispense event occurs.

FIG. 47 illustrates and example process (1220) by which a compliance badge may communicate with a dispenser. The LF receiver on the compliance badge listens for the LF wake-up signal (1222). When the LF wake-up signal is received (1224), the badge activates its RF transceiver (1226) and transmits an LF signal acknowledge (1230) via the RF channel indicated by the dispenser in the LF wake-up signal. If no mailbox data is to be sent (1232), the compliance badge may return to sleep mode (1236). In this example, the RF transceiver (both transmitting and receiving) are powered off when the badge is in sleep mode. In other examples, the RF transmitter may be powered up at periodic intervals (e.g., every few hundred milliseconds) to "ping" for a data gathering station as discussed herein below.

If mailbox data is to be sent (1232), the compliance badge receives the mailbox data (1234) transmitted by the dispenser. In this example, the mailbox data is received via the RF communication channel indicated in the LF wake-up signal. After the mailbox data is received, the dispenser transmits the mailbox data acknowledge (1236). The process (1232-1236) may repeat until the dispenser is finished sending mailbox data or the badge goes out of range of the dispenser. The compliance badge may then return to sleep mode (1236).

Figure 55:
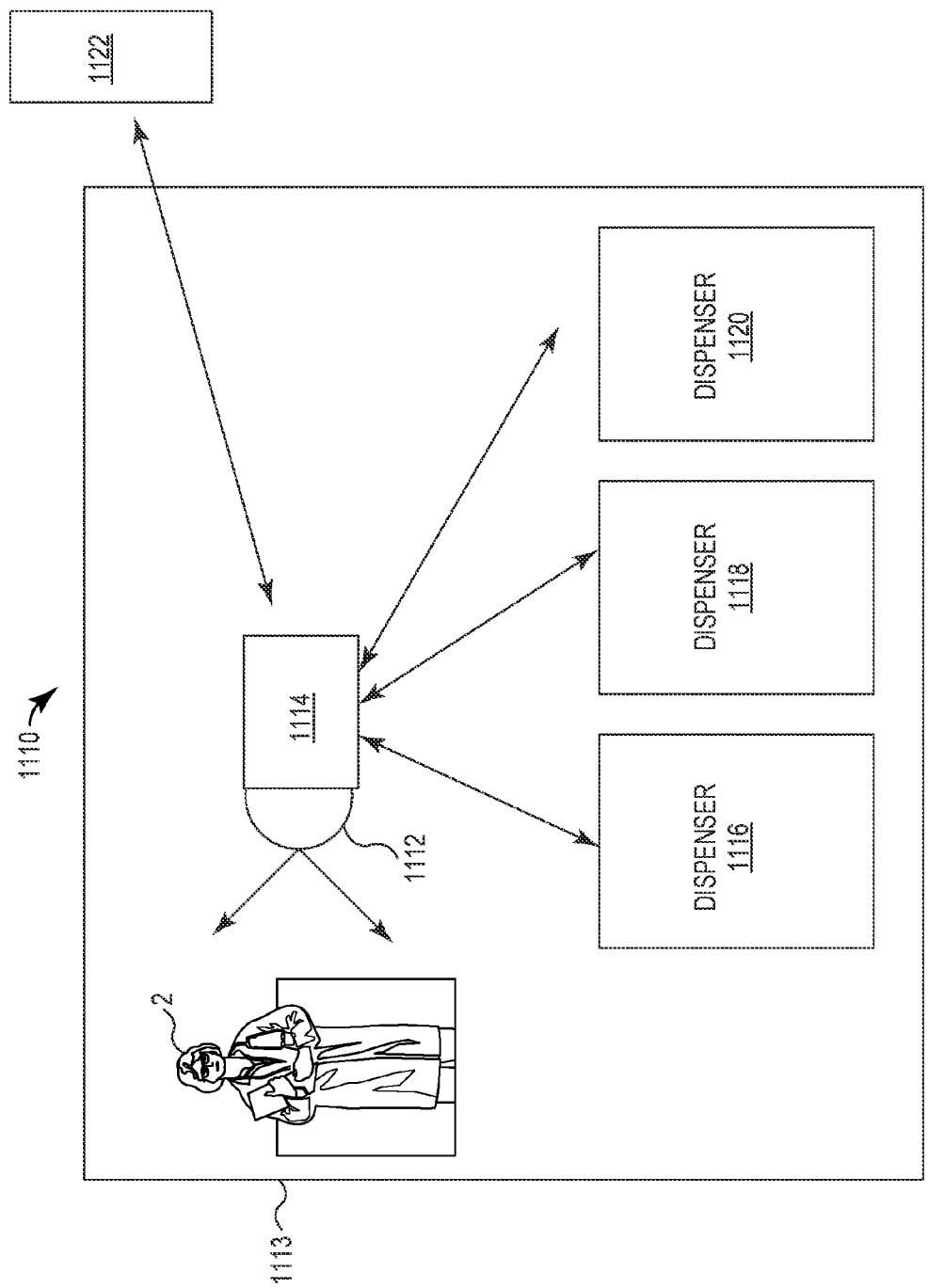
FIG. 55 is a block diagram illustrating another example hand hygiene compliance system.

Processes similar to those described with respect to FIGS. 46, 47 and 55 may also be used with example system 1000B as shown in FIG. 44B. In that example, the LF wake-up signal could be transmitted by the motion detector 1010 upon detection of an entry event. The LF wake-up signal may cause the compliance badge 1004 to activate its RF transceiver so that it may communicate with a dispenser at which the HCW initiates a dispense event. If no dispense event occurs within a predetermined period of time, the compliance badge may return to the sleep mode. Initiation of a dispense event by HCW 2 would trigger the processes described in FIGS. 46 and 47, causing the compliance badge to wake-up and communicate with the dispenser as described in FIGS. 46 and 47, for example.

Although the processes of FIGS. 46 and 47 have been described with respect to the systems of FIGS. 44A and 44B, it shall be understood that these or similar techniques could be implemented in any of the example hand hygiene compliance systems described herein. For example, an LF wake-up signal could be broadcast by a dispenser upon detection of an entry event to cause a compliance badge to activate its RF transceiver (or receiver) may be implemented in any of the systems described herein. Also, an LF wake-up signal could be broadcast by a motion detector upon detection of an entry event in those systems described herein or in other systems that include a motion detector that detects entry events into an AOC. Similarly, the process by which dispense event data and mailbox data is sent may also be implemented in any of the other hand hygiene systems described herein, or in other hand hygiene compliance systems.

As another example, in the system shown in FIGS. 44A and/or 44B, the dispenser/badge communication need not include a wake-up function. Also, the wake-up need not be implemented using LF, nor does the dispenser/badge communication need to be RF. It shall be understood that the specific implementation described is for purposes of example only, and that the disclosure is not limited in this respect.

In addition, although not shown with respect to FIG. 47, compliance badge may analyze some of all of the dispense event records to determine one or more compliance metrics associated with one or more dispense events. For example, the compliance badge may determine a total number of dispense events initiated by the associated HCW over a given period of time; may compare the total number of dispense events to a target; or determine other compliance metrics. Alternatively or in addition, some or all of the dispense event records, badge status data, and/or dispenser mailbox data may be analyzed at a computing device that receives the badge data at any point after it has been downloaded to a data gathering station.

Figure 49:
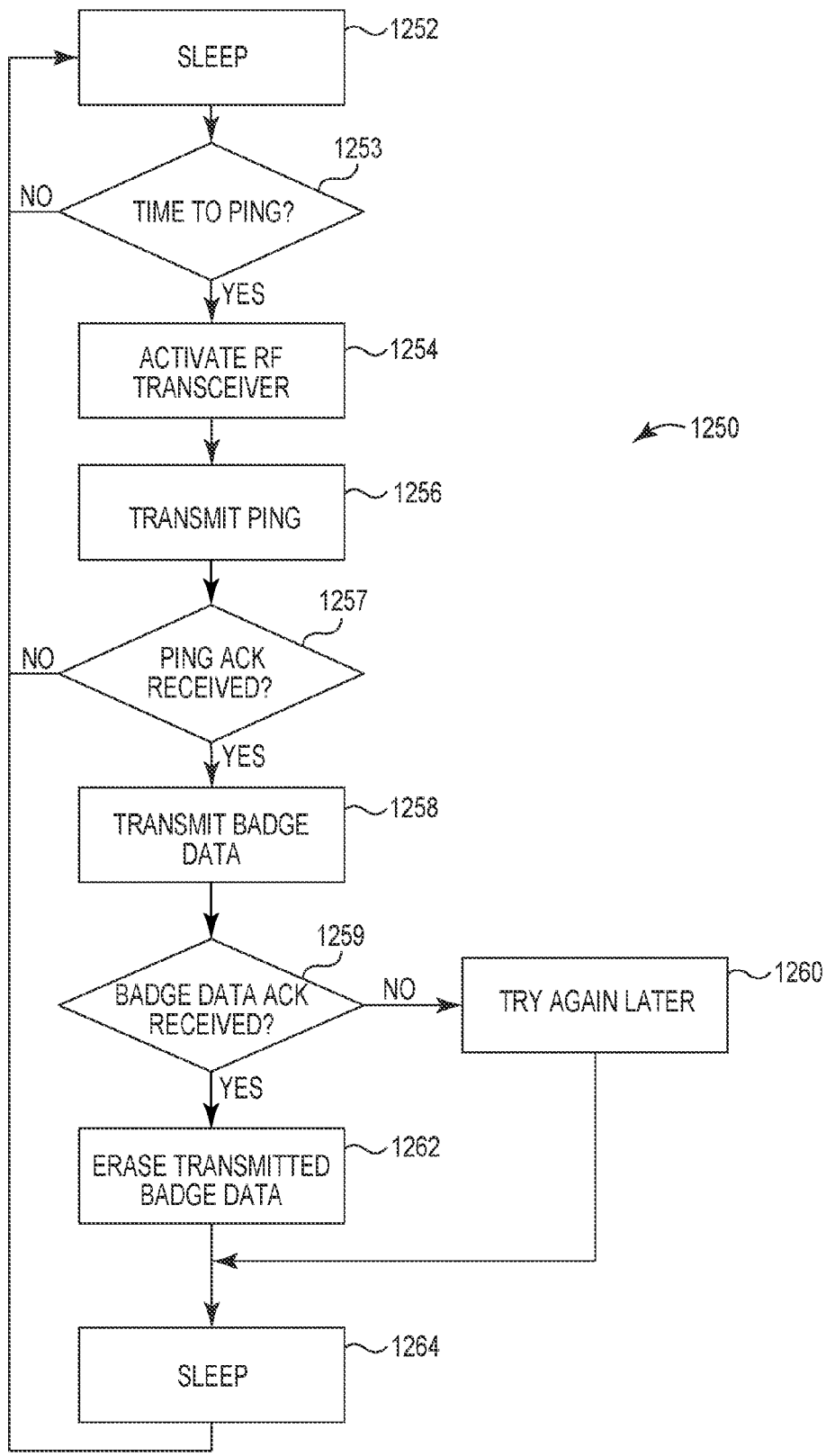
FIG. 49 is a flowchart illustrating an example process by which a compliance badge may communicate with a data gathering station.

FIG. 49 is a flowchart illustrating an example process (1250) by which a compliance badge may communicate with a data gathering station. Process (1250) may be implemented in any of the hand hygiene compliance systems described herein. In this example, a badge, from sleep mode (1252) may at periodic intervals determine whether it is time to send a "ping" for a data gathering station (1253). If not, the badge remains in sleep mode (1252) until it is time to send a ping. If it is time to ping, the badge may activate its RF transceiver (1254) and transmit a ping (1256). If a data gathering station is within range and transmits a ping acknowledge (ping ACK), and the ping ACK is received by the badge (1257), the badge may transmit some or all of its badge data (such as badge data 1035 in FIG. 45). If no ping acknowledge is received by the badge (1257), the badge continues to transmit pings at the predetermined periodic intervals (1252-1256) until ping ACK is received.

The determination as to whether it is time to ping (1253) may be determined in several ways. For example, whether or not a badge is "pinging" may depend on the amount of data the badge has stored. If a badge only has a few records stored it may not ping for a data gathering station, and may instead wait until it has a predetermined amount of badge data to transfer. This may help to save battery life on the compliance badge. In some examples a badge may ping on a periodic basis, such as every few seconds or some other appropriate time interval. In other examples, a combination of these methods may be used.

Once the compliance badge transmits the badge data (1258) it waits to receive a badge data acknowledge from the data gathering station (1259). If no badge data acknowledge is received within a predetermined period of time (e.g., several hundred microseconds), the badge may try sending the badge data again at a later time (1260). The badge may then return to sleep mode (1264). If a badge data acknowledge is received (1259), the badge may erase the transmitted badge data from its memory (1262). This provides memory space for the badge to receive and store additional data in the future. The badge may then return to sleep mode (1264). In the event that the badge does not transmit all of its badge data at once, the process (1258-1259) may repeat until all data is sent or until a badge data acknowledge is not received (for example, if the badge goes out of range).

FIG. 50 is a flowchart illustrating an example process (1270) by which a data gathering station may communicate with a compliance badge. Process (1270) may be implemented in any of the hand hygiene compliance systems described herein. When a data gathering station receives a ping (1272), the data gathering station transmits a ping acknowledge (1274) and establishes communication with the associated compliance badge. The data gathering station receives the badge data from the compliance badge that transmitted the ping (1276). After the badge data is received, the data gathering station transmits a badge data acknowledge (1278). If more badge data is to be sent, the process (1276-1278) may repeat until all of the transmitted badge data has been received or until the badge goes out of range. The data gathering station may then terminate the session (1279).

In a busy healthcare facility, it is likely that more than one compliance badge may attempt to transmit badge data to a particular data gathering station at any given time. In that case, the system may implement techniques to ensure that each compliance badge is given a chance to transfer badge data before their associate memory becomes full. For example, if more than one badge is attempting to or is transmitting badge data at one time, the data gathering station may permit each badge to send only a predetermined amount of data (e.g., a predetermined number of records or bytes), and may cycle between badges, receiving the predetermined amount of data from each, for as long as each badge remains in range. Alternatively, the data gathering station may determine a priority based on the amount of data stored on each badge, the length of time since each badge has downloaded badge data, some combination thereof, or by some other method of establishing priority.

As another alternative, the data gathering station may place each badge requesting to download in a "holding pattern" while communicating with the first badge. While in the "holding pattern," each badge may ping faster than the usual ping rate until the badge data is downloaded or the badge goes out of range.

Communication between the badge and a data gathering station may end as the badge passes out of range. At some point, once the badge is out of range, one of the acknowledgements will not be received and both the badge and the data gathering station may return to their initial operating states.

Once the badge data (such as badge data 1035) has been downloaded to the data gathering station, the badge data may be transmitted to a local or remote computing device for analysis or review. Dispense event data associated with a particular compliance badge can be compared to anticipated or expected dispense event data. For example, a computing device may analyze the badge data from one or more compliance badge to determine one or more compliance metrics associated with one or more dispense events. For example, a computing device may determine a total number of dispense events initiated by the wearer of a particular badge over a given period of time; may compare the number of dispense events to a target; or determine other compliance metrics. If the system server or other computing device includes the HCW identification information associated with each compliance badge, the hand hygiene data may in some examples be associated with a particular individual. Alternatively or in addition, the hand hygiene data may be associated with the individual's job function (e.g., nurse, physician, administrator, cleaning staff, etc.). Further, hand hygiene data associated with a particular hospital or grouping of hospitals or other facilities can be compared to hand hygiene data associated with different hospitals or groups as part of a communications environment.

FIG. 51 is a flowchart illustrating an example process (1280) by which multiple dispense events satisfying a debounce condition may be counted as a single dispense event. At times a user of a hand hygiene product dispenser will "pump" a dispenser multiple times in quick succession. Although the dispenser will detect each individual "pump" of the dispenser, multiple "pumps" in quick succession may usually be attributed to a single user and a single dispense event. a dispenser may "debounce" a sequence of dispenses satisfying a debounce condition. The debounce may be accomplished by the dispenser, in which case the dispenser would increment it's dispense event counter by a single count rather than the actual number of detected dispense events if the debounce condition is satisfied. Alternatively, the debounce may be accomplished at a local or remote computer after the data has been downloaded from the badge. In this example, the dispenser would detect and count each and every detected dispense event, and a local or remote computer would analyze the dispense event records for debounce conditions. As another example, the dispenser may debounce unbadged dispenses while badged dispenses may be debounced at a local and/or remote computer. It shall be understood, therefore, that there are several alternative examples of how, when and where debouncing of dispense events may occur, and that the disclosure is not limited in this respect.

Process (1280) of FIG. 51 begins when multiple dispense events are detected (1282). If one or more debounce conditions are satisfied (1282) the multiple detected dispense events satisfying the debounce condition may be counted as a single dispense event (1286). If the debounce condition(s) are not satisfied, the multiple dispense events are counted as separate dispense events.

To determine whether the debounce condition(s) are satisfied, a processor may compare the time between successive dispenses to a debounce threshold. If successive dispenses occur within the time frame established by the debounce threshold, the debounce condition is satisfied and the successive dispenses are counted as a single dispense. The debounce condition may include, for example, a debounce threshold of between 1-3 seconds between successive dispenses. The debounce condition may also indicate, for example, that all dispenses occurring within a 5 second time frame should be counted as a single dispense. Other debounce conditions and debounce threshold are also contemplated, and the disclosure is not limited in this respect.

It should again be noted that although in certain examples features and combinations of features are depicted as modules or units working together, in different examples, the modules or units do not need to be realized by separate hardware or software components. Further, although combinations of features are depicted in various examples, all the features depicted in a specific example do not necessarily need to be implemented together to produce a hand hygiene system according to the disclosure.

For example, FIG. 52 is a block diagram illustrating a comparatively simple hand hygiene compliance system 1070 that could be used at a hospital, healthcare facility, food service facility, institutional facility, or other facility where hand hygiene monitoring is desired. Hand hygiene compliance system 1070 includes at least one hand hygiene product dispenser which, in the illustrated example includes three dispensers 1072, 1074, and 1076. The dispensers may be associated with an AOC, such as AOC 1071. Each of the hand hygiene product dispensers 1072, 1074, and 1076 may communicate dispenser data to one or more computing devices, such as computing device 1078.

Figure 21C:
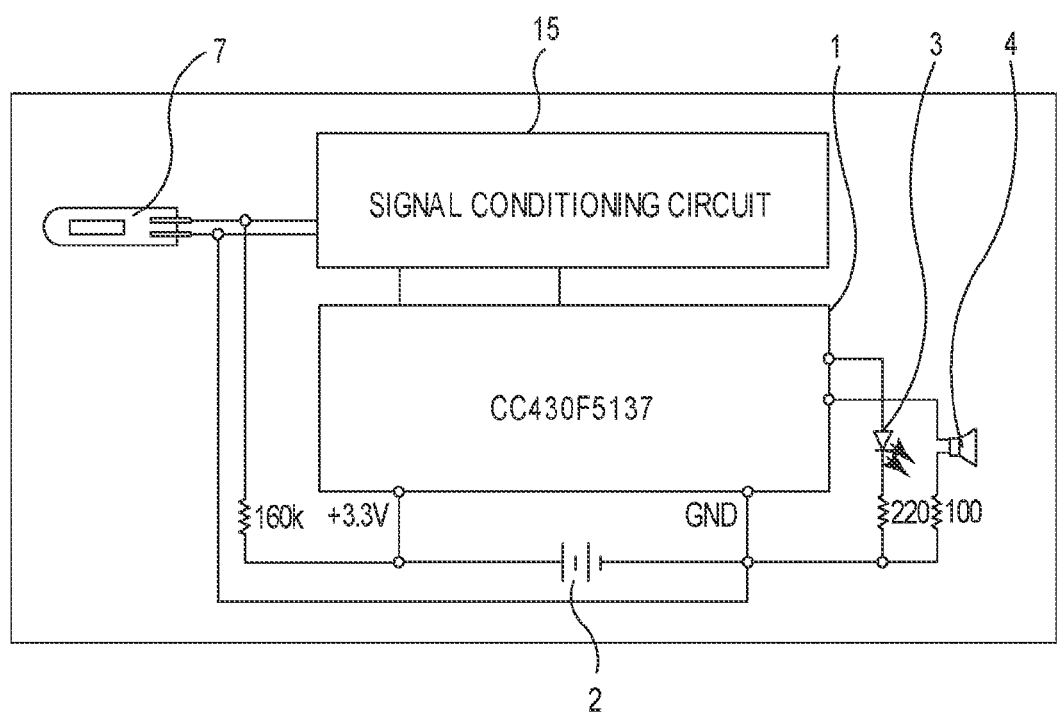
Figure 21D:
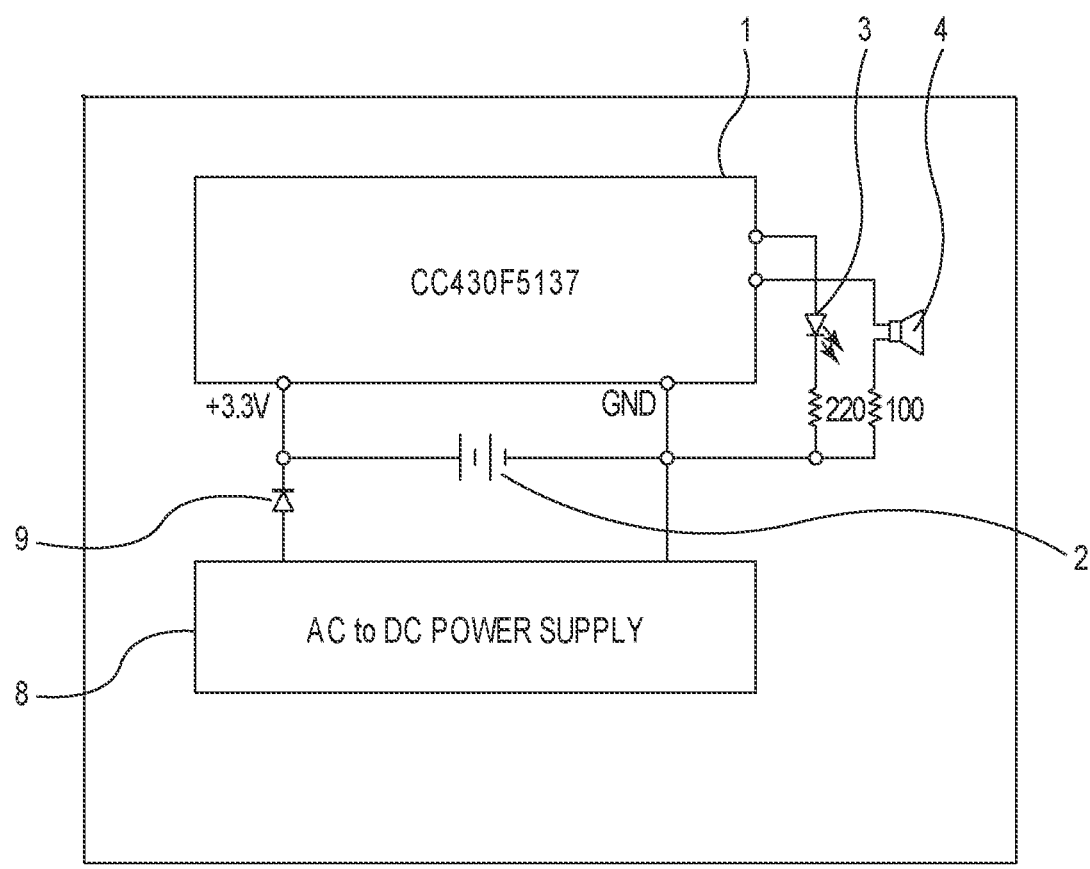

Hand hygiene product dispensers 1072, 1074, and 1076 may be similar to various hand hygiene product dispensers described above including, for example, dispenser 16 (FIGS. 1 and 8), the dispenser shown in FIG. 21C, dispenser 530 (FIG. 25), dispenser 1040 (FIG. 54), and/or any other dispenser shown or described herein. In this respect, each of hand hygiene product dispensers 1072, 1074, and 1076 includes an activation or event sensor to detect a dispense event. Upon detecting a dispense event, the dispenser may transmit at least some dispense event data, which may include any status information concerning the dispenser, to the one or more designated computing devices 1078, e.g., for analysis and storage. Alternatively, the dispenser may transmit dispense event data at periodic intervals or only when a certain amount of data is present on the dispenser. Alternatively, the dispenser may store the dispense event and/or status data for later retrieval by a service technician via a handheld device, laptop computer, cell phone, PDA, or other device that interfaces directly or indirectly with the dispenser, for example.

Each of hand hygiene product dispensers 1072, 1074, and 1076 may communicate with a computing device 1078 via wired or wireless communication, such as a wireless network, radio frequency transmission, wireless telephone network, or other wired or wireless means of communication. In other examples, hand hygiene product dispensers 1072, 1074, and 1076 may communicate with designated computing device 1078 using a USB cable, or using removable media, such as magnetic or optical disks, or memory cards or sticks. In any example, dispense event data may be transmitted to one or more computing devices, such as computing device 1078.

Computing device 1078 may analyze and/or present various hand hygiene data obtained by the dispensers. In this manner, hand hygiene compliance system 1070 may track and monitor hand hygiene product dispenser utilization. Computing device 1078 may determine various compliance metrics for each dispenser or dispensers, such as a total number of dispense events per unit time. The computer 1078 may also analyze and generate reports concerning the dispenser data in various groupings, such as by dispenser, by AOC, by facility, by groups of facilities, or by any other grouping or groupings that may be of interest.

While hand hygiene product dispensers 1072, 1074, and 1076 in the example of FIG. 53A are limited to detecting dispense events, one or more of hand hygiene product dispensers 1072, 1074, and 1076 may include additional functionality, such as a motion detector to detect movement proximate to the hand hygiene product dispenser. A motion detector may provide additional hand hygiene compliance data to determine, for example, how frequently users execute dispense events as compared to how frequently users come within the movement detection proximity of the hand hygiene product dispenser.

Figure 53:
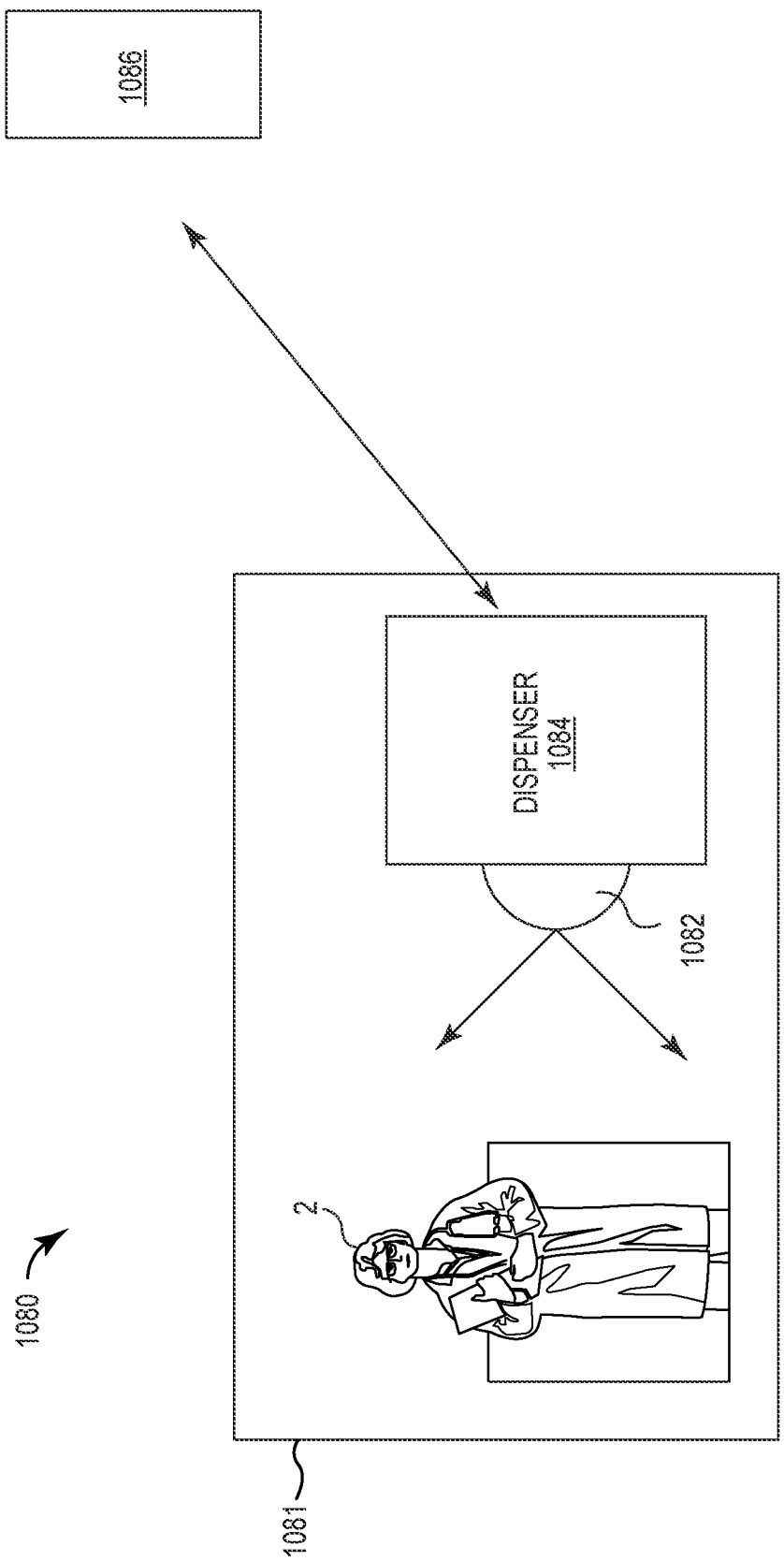
FIG. 53 is a block diagram illustrating another example hand hygiene compliance system.

FIG. 53 is a block diagram illustrating an example hand hygiene compliance system 1080, which includes a hand hygiene product dispenser 1084 and a motion detector 1082. In this example, motion detector 1082 is integrated with hand hygiene product dispenser 1084 and configured to movement within range of the motion detector 1082. Hand hygiene product dispenser 1084 communicates with designated computing device 1086 as described above with respect to FIG. 52.

In general, hand hygiene compliance system 1080, and in particular motion detector 1082, detects movement within the detection range of motion detector 1082. Motion detector 1082 detects movement within the AOC, and may transmit detected motion event data (for example the event time, battery voltage, signal strength, and any other related information) to a designated computing device 1086. Upon detecting a dispense event, hand hygiene product dispenser 1084 may transmit dispense event data and/or detected motion event data, to designated computing device 1086 as discussed above with respect to FIG. 53A.

In addition, to promote hand hygiene compliance, hand hygiene product dispenser 1084 may include visible and/or audible indicator(s) as described with respect to FIG. 12. In these examples, hand hygiene product dispenser 1084 can enter an invitation mode when motion detector 1082 detects movement, e.g., as described with respect to FIG. 19. Designated computing device 1086 and hand hygiene product dispenser 1084, working alone or in cooperation, may initiate a product dispenser invitation mode upon detecting a motion event data. The product dispenser can subsequently exit the invitation mode upon detecting a dispense event or upon the expiration of a target time window. By including invitation mode functionality, hand hygiene system 1080 may increase the likelihood that a person in close proximity to hand hygiene product dispenser 1084 executes a hand hygiene event.

Although the example hygiene compliance system of FIG. 53 only illustrates a single hand hygiene product dispenser 1084 and motion detector 1082, it shall be understood that any of the hand hygiene compliance systems described herein may include multiple hand hygiene product dispensers and/or multiple motion detectors.

Figure 54:
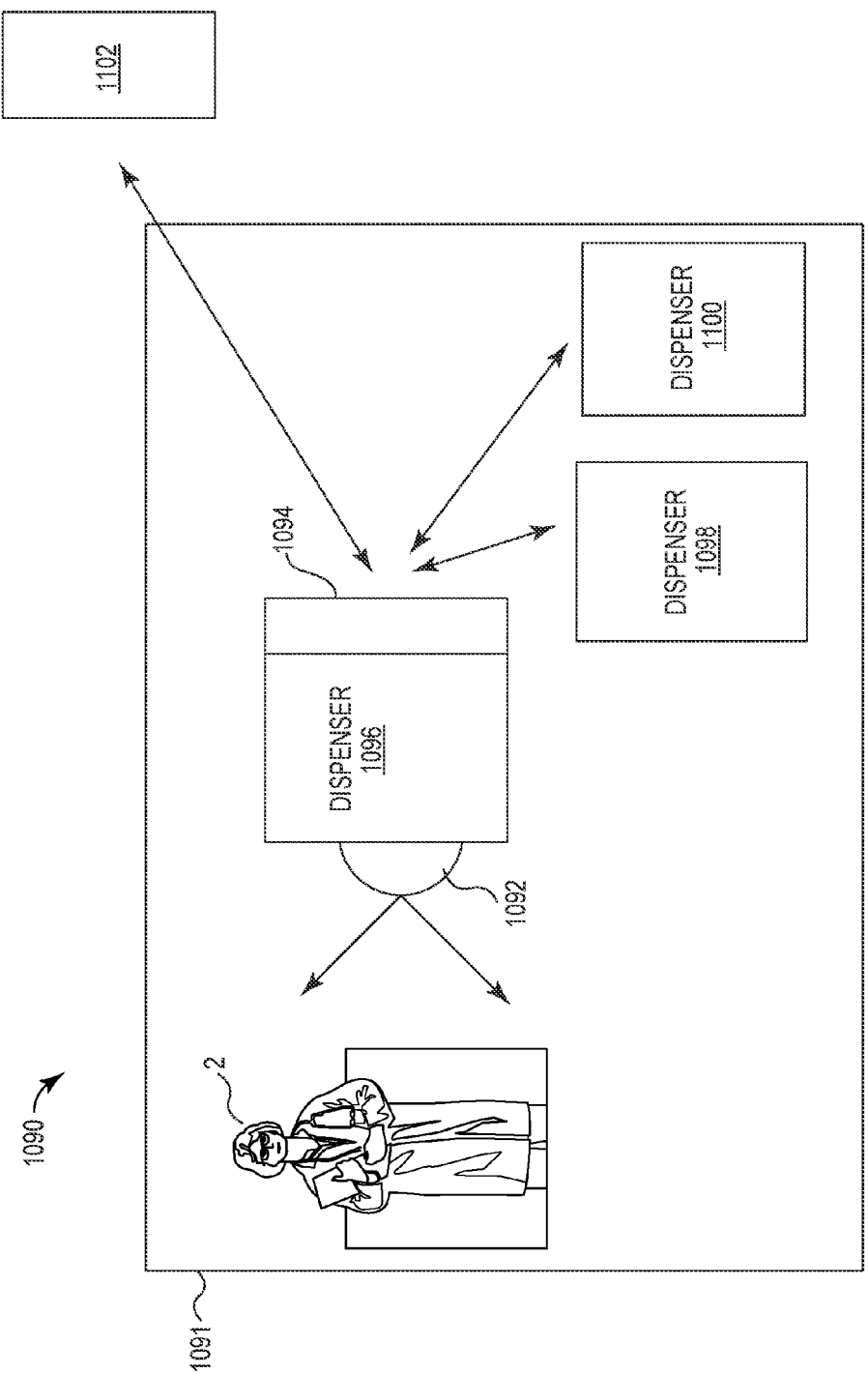
FIG. 54 is a block diagram illustrating an another example hand hygiene compliance system.

FIG. 54 is a block diagram illustrating another example hand hygiene compliance system 1090. Hand hygiene compliance system 1090 includes one or more AOCs, such as AOC 1081, each including a main dispenser 1096 and one or more secondary hand hygiene product dispensers, such as dispensers 1098 and 1100. Main dispenser 1096 includes a communication unit 1094 that communicates dispenser data from the AOC for receipt by one or more computing devices, such as computing device 1102. Main dispenser may also include an optional motion detector 1092 as described above with respect to FIG. 53B. In this example, optional motion detector 1092 and communication unit 1094 are integrated with main dispenser 1096. Secondary dispensers 1098 and 1100 communicate their respective dispenser data to the main dispenser 1096. Main dispenser 1096 in turn communicates with one or more computing devices, such as computing device 1102 via wired or wireless communication.

FIG. 55 is a block diagram illustrating another example hand hygiene compliance system 1110. One or more AOCs, such as AOC 1113, include a coordinator 1114, and at least one hand hygiene product dispenser, in this case dispensers 1116, 1118, and 1120. An optional motion detector 1112 and coordinator 1114 may be integrated into a single unit (as shown in FIG. 55) that in this example is separate from the hand hygiene product dispensers 1116, 1118, and 1120. Alternatively, the optional motion detector and the coordinator need not be integrated, and may instead be implemented separately (such as shown in FIG. 1, for example). Dispensers 1116, 11118, and 1120 (and motion detector 1112, if implemented) communicate their respective dispenser data to coordinator 1114. Coordinator 1114 in turn communicates the dispenser data associated with AOC 1113 to one or more computing devices, such as computing device 1122.

Various examples have been described. These and other examples are within the scope of the following claims.

The invention claimed is:

1. A system comprising:
one or more uniquely identified hand hygiene product dispensers, each associated with an area of concern (AOC) within a facility, that detects a dispense event and transmits a corresponding dispense event signal and dispenser identification information; and
one or more uniquely identified compliance badges, each of that receives the dispense event signal and the dispenser identification information and stores the dispenser identification information in a dispense event record that is associated with the detected dispense event.

2. The system of claim 1 wherein the dispenser increments a dispense event counter upon detection of a dispense event.

3. The system of claim 1 wherein the compliance badge stores a time and date stamp indicative of a time at which the dispense event occurred in the associated dispense event record.

4. The system of claim 3 wherein the dispenser further includes a low frequency transmitter that transmits a low frequency wake-up signal upon detection of a dispense event.

5. The system of claim 4 wherein the at least one compliance badge comprises a low frequency receiver that receives the low frequency wake-up signal and, upon receipt, activates a radio frequency transceiver.

6. The system of claim 1 further comprising one or more data gathering stations associated with the facility, each of which receives one or more of the dispense event records the one or more compliance badges.

7. The system of claim 6 further comprising a computing device that receives the dispense event records directly or indirectly from the one or more data gathering stations and analyzes the dispense event records to monitor hand hygiene events in the facility.

8. The system of claim 7 wherein the computing device generates reports concerning the hand hygiene events in the facility.

9. The system of claim 1 wherein the dispenser counts two or more successive dispense events as a single dispense event when the two or more successive dispense events satisfy a debounce condition.

10. The system of claim 1 wherein a local or a remote computer counts two or more successive dispense events as a single dispense event when the two or more successive dispense events satisfy a debounce condition.

11. The system of claim 1 wherein the dispenser further transmits dispenser status information, wherein the dispenser status information includes one or more of a battery status, a fault conditions, a time of last status data, a data gauge level, a total number of dispense events, and a total number of badged dispense events.

12. A system comprising:
- at least one hand hygiene product dispenser, positioned within an area of concern (AOC) in a facility in which hand hygiene events are to be monitored, that senses a dispense event initiated by a wearer of a compliance badge and transmits dispenser data concerning the dispense event; and
- a plurality of compliance badges, each having uniquely associated badge identification information and each of which is worn by a different one of a plurality of wearers, wherein each compliance badge receives the dispenser data associated with dispense events initiated by the wearer of the compliance badge, and stores dispense event records associated with each dispense event initiated by the wearer.

13. The system of claim 12 wherein each dispenser increments a dispense event counter upon detection of a dispense event.

14. The system of claim 12 wherein the compliance badge stores a time and date stamp indicative of a time at which the dispense event occurred.

15. The system of claim 12 further comprising one or more data gathering stations associated with the facility, each of which receives one or more of the dispense event records the one or more compliance badges.

16. The system of claim 15 further comprising a computing device that receives the dispense event records directly or indirectly from the one or more data gathering stations and analyzes the dispense event records to monitor hand hygiene events in the facility.

17. The system of claim 16 wherein the computing device generates reports concerning the hand hygiene events in the facility.

18. A system comprising:
- at least one hand hygiene product dispenser, positioned within an area of concern (AOC) in a facility in which hand hygiene events are to be monitored, that senses a dispense event and transmits a dispense event signal indicative that a dispense event occurred and that transmits dispenser identification information; and
- a compliance badge that receives the dispense event signal and the dispenser identification information associated with dispense events initiated by a wearer of the compliance badge, and stores dispense event records associated with each dispense event initiated by the wearer.

19. The system of claim 18 further comprising a plurality of compliance badges, each worn by a different one of a plurality of wearers.

20. The system of claim 19 further comprising:
- one or more data gathering stations associated with the facility, each of which receives one or more of the dispense event records from at least one of the plurality of compliance badges; and
- a computing device that receives the dispense event records directly or indirectly from the one or more data gathering stations and analyzes the dispense event records to monitor hand hygiene events in the facility.

* * * * *